(12) United States Patent
Bamba et al.

(10) Patent No.: US 8,507,505 B2
(45) Date of Patent: Aug. 13, 2013

(54) DIHYDROPYRAZOLOPYRIMIDINONE DERIVATIVE

(75) Inventors: Makoto Bamba, Ibaraki (JP); Hidetomo Furuyama, Kanagawa (JP); Toshihiro Sakamoto, Ibaraki (JP); Satoshi Sunami, Ibaraki (JP); Keiji Takahashi, Chiba (JP); Fuyuki Yamamoto, Ibaraki (JP); Takashi Yoshizumi, Ibaraki (JP)

(73) Assignee: MSD K.K., Chiyoda-Ku, Tokyo (JP)

( * ) Notice: Subject to any disclaimer, the term of this patent is extended or adjusted under 35 U.S.C. 154(b) by 44 days.

(21) Appl. No.: 13/133,673

(22) PCT Filed: Dec. 9, 2009

(86) PCT No.: PCT/JP2009/070930
§ 371 (c)(1),
(2), (4) Date: Jun. 9, 2011

(87) PCT Pub. No.: WO2010/067886
PCT Pub. Date: Jun. 17, 2010

(65) Prior Publication Data
US 2011/0243891 A1 Oct. 6, 2011

(30) Foreign Application Priority Data
Dec. 12, 2008 (JP) ................................ 2008-316430

(51) Int. Cl.
| | | |
|---|---|---|
| C07D 487/04 | (2006.01) | |
| C07D 519/00 | (2006.01) | |
| A61K 31/519 | (2006.01) | |
| A61K 31/5377 | (2006.01) | |
| A61P 35/00 | (2006.01) | |
| A61P 35/02 | (2006.01) | |

(52) U.S. Cl.
USPC ....................... 514/262.1; 544/256

(58) Field of Classification Search
USPC ....................... 544/256; 514/262.1
See application file for complete search history.

(56) References Cited

FOREIGN PATENT DOCUMENTS

| WO | 9961444 A2 | 12/1999 |
|---|---|---|
| WO | 2004011465 A1 | 2/2004 |
| WO | 2004041822 A1 | 5/2004 |
| WO | 2004041823 A1 | 5/2004 |
| WO | 2004089955 A1 | 10/2004 |
| WO | 2005011597 A2 | 2/2005 |
| WO | 2008153207 A1 | 12/2008 |
| WO | 2009151997 A1 | 12/2009 |

*Primary Examiner* — Bruck Kifle
(74) *Attorney, Agent, or Firm* — Joan E. Switzer; David A. Muthard

(57) ABSTRACT

The present invention relates to a compound of General Formula (I) below, among others. In the Formula, $Ar^1$ is an optionally substituted aryl or heteroaryl group; $R^1$ is a hydrogen atom, an optionally substituted C1-C6 alkyl group, or an optionally substituted aryl, aralkyl, or heteroaryl group; $R^2$ is an optionally substituted aryl, aralkyl, or heteroaryl group; and $R^3$ is a hydrogen atom or a C1-C6 alkyl group. A compound of the present invention has an excellent Wee1 kinase inhibiting effect, and is therefore useful in the filed of medicine, particularly in various types of cancer therapy.

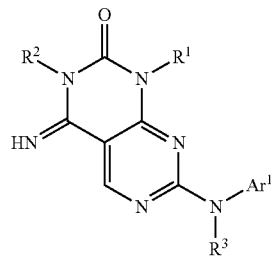

(I)

14 Claims, No Drawings

DIHYDROPYRAZOLOPYRIMIDINONE DERIVATIVE

TECHNICAL FIELD

The present invention is useful in the field of medicine. Specifically, a dihydropyrimidopyrimidine derivative of the present invention is useful as a kinase inhibitor, particularly a Wee1 kinase inhibitor, in the field of various types of cancer therapy.

BACKGROUND ART

Cells have a checkpoint mechanism by which the cell cycle is temporarily arrested in response to DNA damage to allow for DNA repair [*Cell Proliferation*, Vol. 33, pp. 261-274]. In about half of human cancers, the G1 checkpoint function is lost by the mutation or defect of the cancer suppressior gene p53. However, such cancer cells still have the G2 checkpoint function, and this is believed to be a factor causing a reduction in sensitivity to DNA-acting anticancer agents and radiations.

Wee1 kinase is a tyrosine kinase involved in the G2 checkpoint of the cell cycle. Wee1 temporarily arrests the cell cycle at the G2 phase by inactivating Cdc2 through the tyrosine 15 phosphorylation of Cdc2 (Cdk1) involved in the G2 to M phase transition of the cell cycle [*The EMBO Journal*, Vol. 12, pp. 75-85]. Therefore, in p53 defect cancer cells, the role of Wee1 in the G2 checkpoint function is considered to be important for the repair of DNA at the time of DNA damage to avoid cell death. There have been reports that the attenuation of Wee1 expression by RNA interference, or inhibition of Wee1 using compounds enhances sensitivity of cancer cells to adriamycin, X-rays, and γ-rays [*Cancer Biology & Therapy*, Vol. 3, pp. 305-313, and *Cancer Research*, Vol. 61, pp. 8211-8217]. It is therefore believed that Wee1 inhibitor, through inhibition of the G2 checkpoint function in p53 defect cancer cells, can improve sensitivity to DNA-acting anticancer agents or radiations.

Low molecular Wee1 kinase inhibitor compounds are known, as described in, for example, US Patent Application Publication US2005/0250836 (Patent Document 1), Pamphlet of International Publication 2003/091255 (Patent Document 2), *Cancer Research*, Vol. 61, pp. 8211-8217 (Non-Patent Document 1), and *Bioorg & Med. Chem. Lett.*, Vol. 15, pp. 1931-1935 (Non-Patent Document 2). However, the compounds described in these publications are completely different in structure from a compound of the present invention.

Pamphlet of International Publication 99/61444 (Patent Document 3) and Pamphlet of International Publication 2004/041823 (Patent Document 4) disclose compounds relatively similar to a compound of the present invention in part of the structure. However, these publications do not disclose or even suggest the compound as described in the present invention.

DISCLOSURE OF THE INVENTION

An object of the present invention is to provide a novel anticancer agent having a kinase inhibiting effect, particularly Wee1 kinase inhibiting effect, and a sensitizer for cancer chemotherapy or radiation therapy.

After intensive studies, the inventors of the present invention completed the present invention based on the finding that a compound of Formula (I) below has an excellent kinase inhibiting effect, particularly Wee1 kinase inhibiting effect.

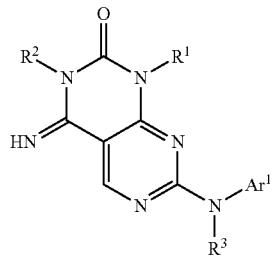

In the Formula, $Ar^1$ is an aryl or heteroaryl group which may have a substituent selected from the group consisting of a halogen atom, a C1-C6 alkyl group, a halo-C1-C6 alkyl group, a hydroxy-C1-C6 alkyl group, a C1-C6 alkoxy group, a C2-C7 alkanoyl group, a hydroxy-C1-C6 alkylamino group, a carbamoyl group, a hydroxy-C1-C6 alkylcarbamoyl group and a group represented by $-Q^1$-$R^{1a}$;

$Q^1$ is a single bond, or a C1-C6 alkylene group, in which one or two or more methylene groups constituting the C1-C6 alkylene group may be independently replaced with an oxygen atom, a sulfur atom, a carbonyl group, an imino group, a sulfinyl group or a sulfonyl group, and may be substituted with a halogen atom, a cyano group, a hydroxyl group, a C1-C6 alkyl group or a C1-C6 alkoxy group;

$R^{1a}$ is a hydrogen atom, a hydroxyl group, a formyl group, a C1-C6 alkyl group, a di-C1-C6 alkylamino group, a hydroxy-C1-C6 alkyl group or a carboxyphenyl group, or a heterocyclic group, including at least one nitrogen atom as a heteroatom in the heterocycle, and which may have a substituent selected from the group consisting of a halogen atom, a hydroxyl group, an oxo group, a C1-C6 alkyl group, a C1-C6 alkoxy group, a hydroxy-C1-C6 alkyl group, a C1-C6 alkoxy-C1-C6 alkyl group and a group represented by —$R^{1b}$;

$R^{1b}$ is a group represented by -$Q^2$-$A^1(R^{1c})R^{1d}$;

$Q^2$ is a single bond, or a C1-C6 alkylene group, in which one or two or more methylene groups constituting the C1-C6 alkylene group may be independently replaced with an oxygen atom, a sulfur atom, a carbonyl group, an imino group, a sulfinyl group or a sulfonyl group, and may be substituted with a halogen atom, a cyano group, a hydroxyl group, an imino group, a C1-C6 alkyl group or a C1-C6 alkoxy group;

$A^1$ is a nitrogen atom, or a methine group which may be substituted with a hydroxyl group, a C1-C6 alkyl group or a hydroxy-C1-C6 alkyl group;

$R^{1c}$ and $R^{1d}$ are independently a hydrogen atom, a carboxyl group, a C1-C6 alkyl group, or a hydroxy-C1-C6 alkyl group, or together represent a C1-C6 alkylene group, in which one or two or more methylene groups constituting the C1-C6 alkylene group may be independently replaced with an oxygen atom, a sulfur atom, a sulfinyl group, a sulfonyl group, a carbonyl group, a vinylene group or a group represented by —N($R^{1e}$)—, and may be substituted with a hydroxyl group, a C1-C6 alkyl group or a hydroxy-C1-C6 alkyl group;

$R^{1e}$ is a hydrogen atom, a formyl group, an acetyl group or a C1-C6 alkyl group;

$R^1$ is a hydrogen atom; a C1-C6 alkyl group which may have a substituent selected from the group consisting of a halogen atom, a hydroxyl group, a cyano group, a C1-C6 alkoxy group, a C3-C6 cycloalkyl group, a C2-C7 alkanoyl group and a C1-C6 alkylsulfonyl group, or an aryl, aralkyl or heteroaryl group which may have a substituent selected from the group consisting of a halogen atom, a hydroxyl group, a cyano group, an amino group, a C1-C6 alkyl group, a C1-C6 alkoxy group, a halo-C1-C6 alkyl group and a hydroxy-C1-C6 alkyl group;

$R^2$ is an aryl, aralkyl or heteroaryl group which may have a substituent selected from the group consisting of a halogen atom, a hydroxyl group, a cyano group, an amino group a nitro group, a carbamoyl group, a C1-C6 alkyl group, a C1-C6 alkoxy group, a C1-C6 alkylsulfonyl group, a halo-C1-C6 alkyl group, a hydroxy-C1-C6 alkyl group and a C1-C6 alkoxy-C1-C6 alkyl group; and $R^3$ is a hydrogen atom or a C1-C6 alkyl group.

With the kinase inhibiting effect, and particularly Wee1 kinase inhibiting effect, a compound (I) of the present invention is useful as a therapeutic agent for various types of cancer, for example, such as brain tumor, head and neck cancer, esophageal cancer, thyroid cancer, small cell cancer, non-small cell cancer, breast cancer, lung cancer, stomach cancer, gallbladder/bile duct cancer, liver cancer, pancreatic cancer, colon cancer, rectal cancer, ovarian cancer, chorioepitheliowa, endometrial cancer, cervical cancer, renal pelvic and ureteral cancer, bladder cancer, prostate cancer, penile cancer, testicular cancer, embryonal carcinoma, Wilms' tumor, skin cancer, malignant melanoma, neuroblastoma, osteosarcoma, Ewing's tumor, soft tissue sarcoma, acute leukemia, chronic lymphocytic leukemia, chronic myeloid leukemia, and Hodgkin's lymphoma. A compound (I) of the present invention is also useful as a sensitizer for the chemotherapy or radiation therapy of these and other cancers.

A compound (I) of the present invention is particularly useful as a therapeutic agent for, for example, breast cancer, lung cancer, pancreatic cancer, colon cancer, ovarian cancer, acute leukemia, chronic lymphocytic leukemia, chronic myeloid leukemia, and Hodgkin's lymphoma, and as a sensitizer for the chemotherapy or radiation therapy of these cancers.

The present invention concerns a compound represented by Formula (I), a pharmaceutically acceptable salt or N-oxide derivative thereof, and a producing method and use thereof.

The present invention is described below in more detail, beginning with the definitions of the terms used herein.

The "halogen atom" means a fluorine atom, a chlorine atom, a bromine atom, and an iodine atom.

The "C1-C6 alkyl group" means a straight-chain or branched alkyl group having 1 to 6 carbon atoms, for example, such as a methyl group, an ethyl group, a propyl group, an isopropyl group, a butyl group, an isobutyl group, a sec-butyl group, a tert-butyl group, a pentyl group, an isopentyl group, a hexyl group, and an isohexyl group.

The "C3-C6 cycloalkyl group" means a cycloalkyl group having 3 to 6 carbon atoms. Examples include a cyclopropyl group, a cyclobutyl group, a cyclopentyl group, and a cyclohexyl group.

The "halo-C1-C6 alkyl group" means the C1-C6 alkyl group as defined above, substituted with one or two or more, preferably 1 to 3 halogen atoms at arbitrary available substitution positions, the halogen atoms being the same or different and as defined above. Examples include a fluoromethyl group, a difluoromethyl group, a trifluoromethyl group, a 2-fluoroethyl group, a 1,2-difluoroethyl group, a chloromethyl group, a 2-chloroethyl group, a 1,2-dichloroethyl group, a bromomethyl group, and an iodomethyl group.

The "C1-C6 alkoxy group" means a straight-chain or branched alkoxy group having 1 to 6 carbon atoms, for example, such as a methoxy group, an ethoxy group, a propoxy group, an isopropoxy group, a butoxy group, a sec-butoxy group, an isobutoxy group, a tert-butoxy group, a pentyloxy group, an isopentyloxy group, a hexyloxy group, and an isohexyloxy group.

The "C1-C6 alkoxy group-C1-C6 alkyl group" means the C1-C6 alkyl group as defined above, substituted with one or two or more, preferably one C1-C6 alkoxy group as defined above at arbitrary available substitution positions. Examples include a methoxymethyl group, an ethoxymethyl group, and a 2-methoxyethyl group.

The "C2-C7 alkanoyl group" means an alkanoyl group having the C1-C6 alkyl group, specifically, an alkanoyl group having 2 to 7 carbon atoms. Examples include an acetyl group, a propionyl group, a butyryl group, an isobutyryl group, a valeryl group, an isovaleryl group, and a pivaloyl group.

Examples of the "aryl group" include a phenyl group, and a naphthyl group.

The "aralkyl group" means the C1-C6 alkyl group as defined above, substituted with one or two or more, preferably one aryl group as defined above at arbitrary available substitution positions. Examples include a benzyl group, a 1-phenylethyl group, a phenethyl group, a 1-naphthylmethyl group, and a 2-naphthylmethyl group.

The "heteroaryl group" means a five- or six-membered monocyclic heteroaryl group having one or two or more, preferably 1 to 3 heteroatoms, the same or different, selected from the group consisting of an oxygen atom, a nitrogen atom, and a sulfur atom, or a condensed-ring heteroaryl group formed by the condensation of the monocyclic heteroaryl group and the aryl group, or by the condensation of the monocyclic heteroaryl groups which may be the same or different. Examples include a pyrrolyl group, a furyl group, a thienyl group, an imidazolyl group, a pyrazolyl group, a thiazolyl group, an isothiazolyl group, an oxazolyl group, an isoxazolyl group, a triazolyl group, a tetrazolyl group, an oxadiazolyl group, a 1,2,3-thiadiazolyl group, a 1,2,4-thiadiazolyl group, a 1,3,4-thiadiazolyl group, a pyridyl group, a pyrazinyl group, a pyrimidinyl group, a pyridazinyl group, a 1,2,4-triazinyl group, a 1,3,5-triazinyl group, an indolyl group, a benzofuranyl group, a benzothienyl group, a benzimidazolyl group, a benzoxazolyl group, a benzisoxazolyl group, a benzothiazolyl group, a benzisothiazolyl group, an indazolyl group, a purinyl group, a quinolyl group, an isoquinolyl group, a phthalazinyl group, a naphthyridinyl group, a quinoxalinyl group, a quinazolinyl group, a cinnolinyl group, a pteridinyl group, and a pyrido[3,2-b]pyridyl group.

The "C1-C6 alkylsulfonyl group" means a straight-chain or branched alkylsulfonyl group having 1 to 6 carbon atoms, for example, such as a methylsulfonyl group, an ethylsulfonyl group, a propylsulfonyl group, an isopropylsulfonyl group, a butylsulfonyl group, a sec-butylsulfonyl group, an isobutylsulfonyl group, a tert-butylsulfonyl group, a pentylsulfonyl group, an isopentylsulfonyl group, a hexylsulfonyl group, and an isohexylsulfonyl group.

The "hydroxy-C1-C6 alkyl group" means the C1-C6 alkyl group as defined above, substituted with one or two or more, preferably 1 or 2 hydroxyl groups at arbitrary available substitution positions. Examples include a hydroxymethyl group, a 2-hydroxyethyl group, a 1-hydroxy-1-methylethyl group, a 1,2-dihydroxyethyl group, and a 3-hydroxypropyl group.

The "hydroxy-C1-C6 alkylamino group" means an amino group monosubstituted with the hydroxy-C1-C6 alkyl group. Examples include a hydroxymethylamino group, a 2-hydroxyethylamino group, a 1-hydroxy-1-methylethylamino group, a 1,2-dihydroxyethylamino group, and a 3-hydroxypropylamino group.

The "hydroxy-C1-C6 alkylcarbamoyl group" means a carbamoyl group monosubstituted with the hydroxy-C1-C6 alkyl group. Examples include a hydroxymethylcarbamoyl group, a 2-hydroxyethylcarbamoyl group, a 1-hydroxy-1-methylethylcarbamoyl group, a 1,2-dihydroxyethylcarbamoyl group, and a 3-hydroxypropylcarbamoyl group.

The "di-C1-C6 alkylamino group" means an amino group disubstituted with the same or different C1-C6 alkyl group defined above. Examples include a dimethylamino group, a diethylamino group, an ethylmethylamino group, and an isopropylmethylamino group.

The "heterocyclic group" (including at least one nitrogen atom as a heteroatom in the heterocycle) means a monocyclic or bicyclic heterocyclic group formed of 3 to 7 ring atoms in each ring, and containing at least one nitrogen atom, and additionally, one or two or more, preferably one heteroatom, the same or different, selected from the group consisting of an oxygen atom, a nitrogen atom, and a sulfur atom. The heterocyclic group may be aromatic or aliphatic. Further, the bicyclic heterocyclic group may have a Spiro structure sharing one heteroatom by two rings, or a bicyclo structure sharing two or more heteroatoms. Examples of the nitrogen-containing heterocyclic group include a pyrrolyl group, an imidazolyl group, a pyrazolyl group, a thiazolyl group, an isothiazolyl group, an oxazolyl group, an isoxazolyl group, a triazolyl group, a tetrazolyl group, an oxadiazolyl group, a 1,2,3-thiadiazolyl group, a 1,2,4-thiadiazolyl group, a 1,3,4-thiadiazolyl group, a pyridyl group, a pyrazinyl group, a pyrimidinyl group, a pyridazinyl group, a 1,2,4-triazinyl group, a 1,3,5-triazinyl group, an indolyl group, a benzimidazolyl group, a benzoxazolyl group, a benzisoxazolyl group, a benzothiazolyl group, a benzisothiazolyl group, an indazolyl group, a purinyl group, a quinolyl group, an isoquinolyl group, a phthalazinyl group, a naphthyridinyl group, a quinoxalinyl group, a quinazolinyl group, a cinnolinyl group, a pteridinyl group, a pyrido[3,2-b]pyridyl group, an azetidinyl group, a pyrrolidinyl group, a dihydro-1,2,4-triazolyl group, a dihydro-1,2,4-oxadiazolyl group, a dihydro-1,3,4-oxadiazolyl group, a dihydro-1,2,4-thiadiazolyl group, a dihydro-1,2,3,5-oxathiadiazolyl group, a piperidinyl group, a piperazinyl group, a dihydropyridyl group, a dihydropyridazinyl group, a morpholinyl group, a thiomorpholinyl group, a dihydropyrazolo[3,2-b]oxazolyl group, a 2,6-diazaspiro[3.5]nonyl group, a 2,7-diazaspiro[3.5]nonyl group, a 2,7-diazaspiro[4.5]decyl group, a 2,7-diazabicyclo[3.3.0]octyl group, a 3,6-diazabicyclo[3.3.0]octyl group, and a quinuclidyl group.

The "C1-C6 alkylene group" means an alkylene group having 1 to 6 carbon atoms. Examples include a methylene group, an ethylene group, a trimethylene group, a tetramethylene group, a pentamethylene group, and a hexamethylene group.

A "pharmaceutically acceptable salt" of a compound of the present invention means a medicinally acceptable salt commonly used. For example, when a carboxyl group or a hydroxyl group is employed, the salt may be a base addition salt formed at the carboxyl group or the hydroxyl group. When an amino group, or a basic nitrogen-containing heterocyclic group or other heterocyclic groups are employed, the salt may be an acid addition salt formed at the amino group or the basic nitrogen-containing heterocyclic group or other heterocyclic groups.

Examples of the base addition salt include: alkali metal salts such as sodium salt and potassium salt; alkali-earth metal salts such as calcium salt and magnesium salt; ammonium salts; and organic amine salts such as trimethylamine salt, triethylamine salt, dicyclohexylamine salt, ethanolamine salt, diethanolamine salt, triethanolamine salt, procaine salt, and N,N-dibenzylethylenediamine salt.

Example of the acid addition salt include: inorganic acid salts such as hydrochloride, sulfate, nitrate, phosphate, and perchlorate; organic acid salts such as maleate, fumarate, tartrate, citrate, ascorbate, and trifluoroacetate; and sulfonates such as methanesulfonate, isethionate, benzenesulfonate, and p-toluenesulfonate.

The "N-oxide derivative" of a compound of the present invention means a pharmaceutically acceptable compound that has formed an N-oxide by oxidation of one or two or more arbitrary nitrogen atoms present in a compound of the present invention and capable of forming N-oxide. An example is a compound formed by oxidation of the nitrogen atom present in the ring of the dihydropyrimido[4,5-d]pyrimidine structure of a compound of the present invention.

The following discloses a compound of the present invention in more detail based on specific preferable examples of various symbols used herein.

An means an aryl or heteroaryl group which may have a substituent selected from the group consisting of a halogen atom, a C1-C6 alkyl group, a halo-C1-C6 alkyl group, a hydroxy-C1-C6 alkyl group, a C1-C6 alkoxy group, a C2-C7 alkanoyl group, a hydroxy-C1-C6 alkylamino group, a carbamoyl group, a hydroxy-C1-C6 alkylcarbamoyl group, and a group represented by $-Q^1-R^{1a}$.

The "aryl or heteroaryl group which may have a substituent selected from the group consisting of a halogen atom, a C1-C6 alkyl group, a halo-C1-C6 alkyl group, a hydroxy-C1-C6 alkyl group, a C1-C6 alkoxy group, a C2-C7 alkanoyl group, a hydroxy-C1-C6 alkylamino group, a carbamoyl group, a hydroxy-C1-C6 alkylcarbamoyl group, and a group represented by $-Q^1-R^{1a}$" means the aryl or heteroaryl group as defined above, either unsubstituted or substituted at arbitrary available substitution positions. The substituent, selected from the group consisting of a halogen atom, a C1-C6 alkyl group, a halo-C1-C6 alkyl group, a hydroxy-C1-C6 alkyl group, a C1-C6 alkoxy group, a C2-C7 alkanoyl group, a hydroxy-C1-C6 alkylamino group, a carbamoyl group, a hydroxy-C1-C6 alkylcarbamoyl group, and a group represented by $-Q^1-R^{1a}$, may be the same or different, and one or two or more, preferably 1 or 2 substituents may be selected.

Preferable examples of the substituent halogen atom include a fluorine atom, and a chlorine atom.

Preferable examples of the substituent C1-C6 alkyl group include a methyl group, and an ethyl group.

Preferable examples of the substituent halo-C1-C6 alkyl group include a fluoromethyl group, difluoromethyl group, and a trifluoromethyl group.

Preferable examples of the substituent hydroxy-C1-C6 alkyl group include a hydroxymethyl group, and a 2-hydroxyethyl group.

Preferable examples of the substituent C1-C6 alkoxy group include a methoxy group, and an ethoxy group.

Preferable examples of the substituent C2-C7 alkanoyl group include an acetyl group.

Preferable examples of the substituent hydroxy-C1-C6 alkylamino group include a hydroxymethylamino group, and a 2-hydroxyethylamino group.

Preferable examples of the substituent hydroxy-C1-C6 alkylcarbamoyl group include a hydroxymethylcarbamoyl group, and a 2-hydroxyethylcarbamoyl group.

In the substituent group represented by $Q^1$ is a single bond, or a C1-C6 alkylene group, in which one or two or more methylene groups constituting the C1-C6 alkylene group may be independently replaced with an oxygen atom, a sulfur atom, a carbonyl group, an imino group, a sulfinyl group or a sulfonyl group, and may be substituted with a halogen atom, a cyano group, a hydroxyl group, a C1-C6 alkyl group or a C1-C6 alkoxy group. $R^{1a}$ is a hydrogen atom, a hydroxyl group, a formyl group, a C1-C6 alkyl group, a di-C1-C6 alkylamino group, a hydroxy-C1-C6 alkyl group or a carboxyphenyl group; or a heterocyclic group, including at least one nitrogen atom as a heteroatom in the heterocycle, and which may have a substituent selected from the group consisting of a halogen atom, a hydroxyl group, an oxo group, a C1-C6 alkyl group, a C1-C6 alkoxy group, a hydroxy-C1-C6 alkyl group, a C1-C6 alkoxy-C1-C6 alkyl group and a group represented by —$R^{1b}$.

Preferable examples of the "C1-C6 alkylene group" represented by $Q^1$ include a methylene group, an ethylene group, and a trimethylene group.

One or two or more methylene groups constituting the C1-C6 alkylene group represented by $Q^1$ may be independently replaced with an oxygen atom, a sulfur atom, a carbonyl group, an imino group, a sulfinyl group, or a sulfonyl group. Preferable examples of such replaced groups include those selected from the following Formulae (aa1'):

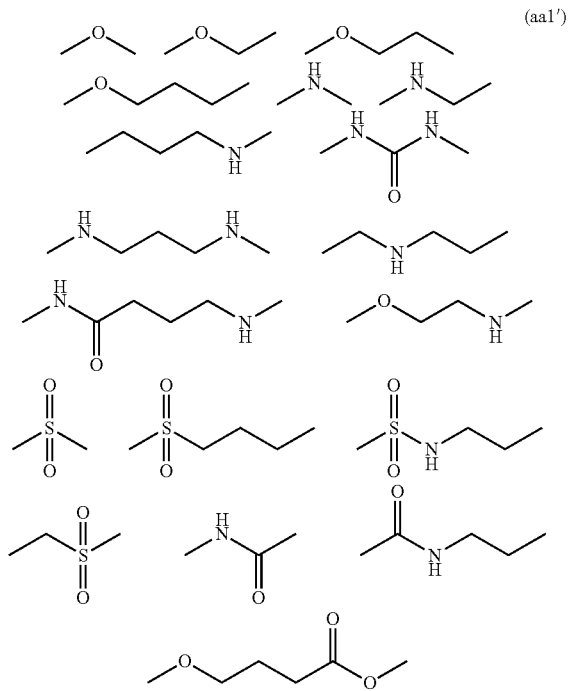

Groups selected from the following Formulae (aa1) are more preferable.

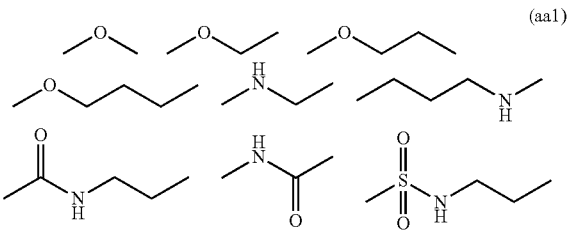

The C1-C6 alkylene group represented by $Q^1$, or the groups represented by Formulae (aa1') or (aa1) may be substituted with a halogen atom, a cyano group, a hydroxyl group, a C1-C6 alkyl group or a C1-C6 alkoxy group at arbitrary available substitution positions. Preferable examples of the "C1-C6 alkyl group" represented by $R^{1a}$ include a methyl group, and an ethyl group.

Preferable examples of the "di-C1-C6 alkylamino group" represented by $R^{1a}$ include a dimethylamino group, a diethylamino group, and an isopropylmethylamino group.

Preferable examples of the "hydroxy-C1-C6 alkyl group" represented by $R^{1a}$ include a hydroxymethyl group, and a hydroxyethyl group.

The "heterocyclic group, including at least one nitrogen atom as a heteroatom in the heterocycle, and which may have a substituent selected from the group consisting of a halogen atom, a hydroxyl group, an oxo group, a C1-C6 alkyl group, a C1-C6 alkoxy group, a hydroxy-C1-C6 alkyl group, a C1-C6 alkoxy-C1-C6 alkyl group and a group represented by —$R^{1b}$" for $R^{1a}$ means the heterocyclic group as defined above, either unsubstituted or substituted at arbitrary available substitution positions. The substituent, selected from the group consisting of a halogen atom, a hydroxyl group, an oxo group, a C1-C6 alkyl group, a C1-C6 alkoxy group, a hydroxy-C1-C6 alkyl group, a C1-C6 alkoxy-C1-C6 alkyl group and a group represented by —$R^{1b}$, may be the same or different, and one or two or more, preferably 1 or 2 substituents may be selected.

The "heterocyclic group" itself of the "heterocyclic group, including at least one nitrogen atom as a heteroatom in the heterocycle, and which may have a substituent selected from the group consisting of a halogen atom, a hydroxyl group, an oxo group, a C1-C6 alkyl group, a C1-C6 alkoxy group, a hydroxy-C1-C6 alkyl group, a C1-C6 alkoxy-C1-C6 alkyl group, and a group represented by —$R^{1b}$" for $R^{1a}$ may be, for example, an imidazolyl group, a pyrazolyl group, a thiazolyl group, an oxazolyl group, an oxadiazolyl group, a pyridyl group, a pyrazinyl group, a pyrimidinyl group, an azetidinyl group, a pyrrolidinyl group, a piperidinyl group, a piperazinyl group, a morpholinyl group, a dihydropyrazolo[3,2-b]oxazolyl group, a 2,6-diazaspiro[3.5]nonyl group, a 2,7-diazaspiro[3.5]nonyl group, a 2,9-diazaspiro[4.5]decyl group, or a quinuclidyl group.

Preferable examples of the substituent halogen atom include a fluorine atom, and a chlorine atom.

Preferable examples of the substituent C1-C6 alkyl group include a methyl group, and an ethyl group.

Preferable examples of the substituent hydroxy-C1-C6 alkyl group include a hydroxymethyl group.

Preferable examples of the substituent C1-C6 alkoxy-C1-C6 alkyl group include a methoxymethyl group.

The substituent group represented by —$R^{1b}$ means a group represented by -$Q^2$-$A^1(R^{1c})R^{1d}$.

In the group represented by -$Q^2$-$A^1(R^{1c})R^{1d}$, $Q^2$ is a single bond, or a C1-C6 alkylene group, in which one or two or more methylene groups constituting the C1-C6 alkylene group may be independently replaced with an oxygen atom, a sulfur atom, a carbonyl group, an imino group, a sulfinyl group or a sulfonyl group, and may be substituted with a halogen atom, a cyano group, a hydroxyl group, an imino group, a C1-C6 alkyl group or a C1-C6 alkoxy group; $A^1$ is a nitrogen atom, or a methine group which may be substituted with a hydroxyl group, a C1-C6 alkyl group or a hydroxy-C1-C6 alkyl group; $R^{1c}$ and $R^{1d}$ are independently a hydrogen atom, a carboxyl group, a C1-C6 alkyl group or a hydroxy-C1-C6 alkyl group, or together represent a C1-C6 alkylene group, in which one or two or more methylene groups constituting the C1-C6 alkylene group may be independently replaced with an oxygen atom, a sulfur atom, a sulfinyl group, a sulfonyl group, a carbonyl group, a vinylene group or a group represented by —N(R$^{1e}$)—, and may be substituted with a hydroxyl group, a C1-C6 alkyl group or a hydroxy-C1-C6 alkyl group; R$^{1e}$ is a hydrogen atom, a formyl group or a C1-C6 alkyl group.

The "methine group which may be substituted with a hydroxyl group, a C1-C6 alkyl group or a hydroxy-C1-C6 alkyl group" for A$^1$ means a methine group either unsubstituted or substituted with a substituent selected from the group consisting of a hydroxyl group, a C1-C6 alkyl group, and a hydroxy-C1-C6 alkyl group.

Preferable examples of the substituent C1-C6 alkyl group include a methyl group, and an ethyl group.

Preferable examples of the substituent hydroxy-C1-C6 alkyl group include a hydroxymethyl group, a 2-hydroxyethyl group, a 2-hydroxypropyl group, and a 2-methyl-2-hydroxypropyl group.

The substituent is preferably a hydroxyl group or a C1-C6 alkyl group, for example.

Preferable examples of the "C1-C6 alkylene group" represented by Q$^2$ include a methylene group, an ethylene group, and a trimethylene group.

One or two or more methylene groups constituting the C1-C6 alkylene group represented by Q$^2$ may be independently replaced with an oxygen atom, a sulfur atom, a carbonyl group, an imino group, a sulfinyl group or a sulfonyl group. Preferable examples of such replaced groups include those selected from the following Formulae (aa2):

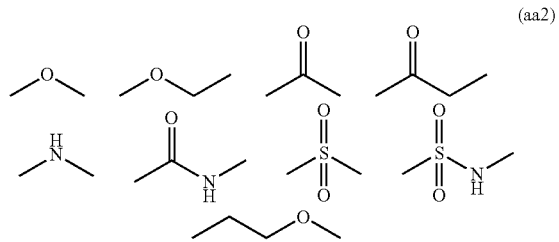

(aa2)

The C1-C6 alkylene group represented by Q$^2$, or the groups represented by Formulae (aa2) may be substituted with a halogen atom, a cyano group, a hydroxyl group, an imino group, a C1-C6 alkyl group, or a C1-C6 alkoxy group at arbitrary available substitution positions.

Preferable examples of the substituent C1-C6 alkyl group include a methyl group.

Preferable examples of the "C1-C6 alkyl group" represented by R$^{1c}$ or R$^{1d}$ include a methyl group, an ethyl group, a propyl group, and an isopropyl group.

Preferable examples of the "hydroxy-C1-C6 alkyl group" represented by R$^{1c}$ or R$^{1d}$ include a hydroxymethyl group, and a 2-hydroxyethyl group.

Preferable examples of the C1-C6 alkylene group formed together by R$^{1c}$ and R$^{1d}$ include a trimethylene group, a tetramethylene group, a pentamethylene group, and a hexamethylene group. When the binding "A$^1$" is a nitrogen atom, the C1-C6 alkylene group formed together by R$^{1c}$ and R$^{1d}$ means a 1-azetidinyl group, a 1-pyrrolidinyl group, or a piperidino group, including the nitrogen atom. When "A$^1$" is a methine group, the C1-C6 alkylene group formed together by R$^{1c}$ and R$^{1d}$ means a cyclobutyl group, a cyclopentyl group, a cyclohexyl group, or a cycloheptyl group including the methine group. Preferable are a cyclobutyl group, a 1-azetidinyl group, a 1-pyrrolidinyl group, and a piperidino group etc.

One or two or more methylene groups constituting the C1-C6 alkylene group may be independently replaced with an oxygen atom, a sulfur atom, a sulfinyl group, a sulfonyl group, a carbonyl group, a vinylene group or a group represented by —N(R$^{1e}$)—. Preferable examples of such a group include an azetidinyl group, a pyrrolidinyl group, a piperidino group, and a piperazino group. These groups may be substituted with a hydroxyl group, a C1-C6 alkyl group, or a hydroxy-C1-C6 alkoxy group at arbitrary available substitution positions.

In the group represented by —N(R$^{1e}$)—, R$^{1e}$ is a hydrogen atom, a formyl group, an acetyl group or a C1-C6 alkyl group.

Preferable examples of the "C1-C6 alkyl group" represented by R$^{1e}$ include a methyl group.

The preferable form of the group represented by -Q$^2$-A$^1$(R$^{1c}$)R$^{1d}$, for example, is when:

(i) Q$^2$ is a single bond, A$^1$ is a nitrogen atom, and R$^{1c}$ and R$^{1d}$ are independently a hydrogen atom or a C1-C6 alkyl group;

(ii) Q$^2$ is a single bond, or a C1-C6 alkylene group, in which one of the methylene groups constituting the C1-C6 alkylene group may be replaced with a carbonyl group, A$^1$ is a methine group, and R$^{1c}$ and R$^{1d}$ are hydrogen atoms;

(iii) Q$^2$ is a C1-C6 alkylene group, in which one of the methylene groups constituting the C1-C6 alkylene group may be replaced with an oxygen atom or a carbonyl group, and may be substituted with a C1-C6 alkyl group, A$^1$ is a nitrogen atom, and R$^{1c}$ and R$^{1d}$ are independently a C1-C6 alkyl group; or (iv) Q$^2$ is a single bond, A$^1$ is a methine group, and R$^{1c}$ and R$^{1d}$ together represent a C1-C6 alkylene group, in which one of the methylene groups constituting the C1-C6 alkylene group may be replaced with a group represented by —N(R$^{1e}$)—, where R$^{1e}$ is as defined in claim 1.

The foregoing condition (ii) is more preferable.

Specific examples of the group represented by -Q$^2$-A$^1$(R$^{1c}$)R$^{1d}$ include a methyl group, an ethyl group, a propyl group, an isopropyl group, a 1-hydroxy-1-methylethyl group, a cyclopropyl group, a cyclobutyl group, a cyclopropylmethyl group, a 1-acetyl-3-azetidinyl group, a 3-hydroxy-1-azetinyl group, a 2-methyl-2-azetinyl group, a 1-pyrrolidinyl group, a cyclopentyl group, a 2-hydroxycyclopentyl group, a hydroxymethyl group, a 2-hydroxyethyl group, a methylimino group, a methoxy group, a methoxymethyl group, a 2-methoxyethyl group, a 2-ethoxyethyl group, a 2-hydroxy-2-methylpropyl group, a 3-fluoro-2-hydroxypropyl group, a formyl group, an acetyl group, a propionyl group, a 2-methoxyacetyl group, a tert-butoxycarbonyl group, a methylsulfonyl group, a 2-(methylsulfonyl)ethyl group, a tert-butylamino group, a dimethylamino group, a dimethylaminomethyl group, a 2-(dimethylamino)ethyl group, a dimethylcarbamoyl group, a dimethylcarbamoylmethyl group, a 2-(dimethylamino)acetyl group, and a 2-dimethylamino-2-methyl-acetyl group. Preferable examples include a methyl group, a 1-acetyl-3-azetidinyl group, a 3-hydroxy-1-azetinyl group, a 2-methyl-2-azetinyl group, a 1-pyrrolidinyl group, a hydroxymethyl group, a 2-hydroxyethyl group, a methylimino group, a methoxy group, a methoxymethyl group, a 2-methoxyethyl group, a 2-hydroxy-2-methylpropyl group, a formyl group, a tert-butylamino group, a dimethylamino group, a dimethylaminomethyl group, a 2-(dimethylamino)ethyl group, a dimethylcarbamoyl group, a 2-(dimethylamino)acetyl group, and a 2-dimethylamino-2-methyl-acetyl group. More preferable examples include a methyl group, a hydroxymethyl group, a 2-hydroxyethyl group, a dimethylamino group, a dimethylaminomethyl group, and a 2-(dimethylamino)acetyl group.

Examples of the substituent of the optionally substituted heterocyclic group represented by R$^{1a}$ include a fluorine atom, a chlorine atom, a methyl group, an ethyl group, a hydroxymethyl group, a methoxymethyl group, a 1-acetyl-3-azetidinyl group, a 3-hydroxy-1-azetinyl group, a 2-methyl-2-azetinyl group, a 1-pyrrolidinyl group, a hydroxymethyl group, a 2-hydroxyethyl group, a methylimino group, a methoxy group, a methoxymethyl group, a 2-methoxyethyl group, a 2-hydroxy-2-methylpropyl group, a formyl group, a tert-butylamino group, a dimethylamino group, a dimethylaminomethyl group, a 2-(dimethylamino)ethyl group, a dimethylcarbamoyl group, a 2-(dimethylamino)acetyl group, and a 2-dimethylamino-2-methyl-acetyl group. Preferable examples include a methyl group, a hydroxymethyl group, a methoxymethyl group, a 2-hydroxyethyl group, a tert-butylamino group, a dimethylamino group, a dimethylaminomethyl group, and a 2-(dimethylamino)acetyl group. The methyl group is particularly preferable.

Examples of the preferable forms of the group represented by $-Q^1-R^{1a}$ include those selected from the following Formulae (a1):

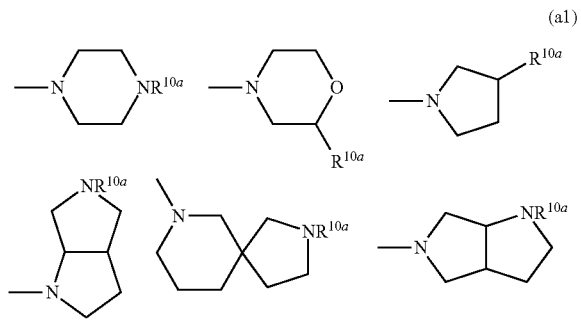

One or two or more methylene groups constituting the groups represented by Formulae (a1) may be independently substituted with a substituent selected from the group consisting of a halogen atom, a hydroxyl group, an oxo group, a C1-C6 alkyl group, a C1-C6 alkoxy group, a hydroxy-C1-C6 alkyl group, a C1-C6 alkoxy-C1-C6 alkyl group and a group represented by $—R^{1b}$, $R^{10a}$ is a hydrogen atom, a C1-C6 alkyl group, a hydroxy-C1-C6 alkyl group or a group represented by $—R^{1b}$, and $R^{1b}$ is as defined above.

Preferable examples of the "C1-C6 alkyl group" represented by $R^{10a}$ include a methyl group.

Preferable examples of the "hydroxy-C1-C6 alkyl group" represented by $R^{10a}$ include a hydroxymethyl group, and a 2-hydroxyethyl.

Specific examples of the group represented by $-Q^1-R^{1a}$ include a 1-piperazinyl group, a 4-methyl-1-piperazinyl group, a 4-ethyl-1-piperazinyl group, a 4-propyl-1-piperazinyl group, a 4-isopropyl-1-piperazinyl group, a 4-tert-butyl-1-piperazinyl group, a 4-hydroxymethyl-1-piperazinyl group, a 4-(1-hydroxy-1-methylethyl)-1-piperazinyl group, a 4-cyclopropyl-1-piperazinyl group, a 4-cyclobutyl-1-piperazinyl group, a 4-cyclopropylmethyl-1-piperazinyl group, a 4-(1-acetyl-3-azetidinyl)-1-piperazinyl group, a 4-cyclopentyl-1-piperazinyl group, a 4-(2-hydroxycyclopentyl)-1-piperazinyl group, a 4-(2-hydroxyethyl)-1-piperazinyl group, a 4-(2-methoxyethyl)-1-piperazinyl group, a 4-(2-ethoxyethyl)-1-piperazinyl group, a 4-(2-hydroxy-2-methylpropyl)-1-piperazinyl group, a 4-(3-fluoro-2-hydroxypropyl)-1-piperazinyl group, a 4-acetyl-1-piperazinyl group, 4-propionyl-1-piperazinyl group, a 4-methyl-2-methoxymethyl-1-piperazinyl group, a 4-(2-methoxyacetyl)-1-piperazinyl group, a 4-tert-butoxycarbonyl-1-piperazinyl group, a 4-methylsulfonyl-1-piperazinyl group, a 4-(2-(methylsulfonyl)ethyl)-1-piperazinyl group, a 4-(dimethylcarbamoyl) group, a 4-(dimethylcarbamoylmethyl)-1-piperazinyl group, a 4-(2-(dimethylamino)acetyl)-1-piperazinyl group, a 4-methyl-3-oxo-1-piperazinyl group, piperidino group, a 4-hydroxypiperidino group, morpholino group, a 3-(dimethylaminomethyl)-1-morpholino group, a 3-hydroxymethyl-1-morpholino group, thiomorpholino group, a 1,1-dioxidothiomorpholino group, perhydro-1H-azepin-1-yl group, a perhydro-1H-1,4-diazepin-1-yl group, a 4-methyl-perhydro-1H-1,4-diazepin-1-yl group, a 5-oxo-perhydro-1H-1,4-diazepin-1-yl group, a 4-methyl-5-oxo-perhydro-1H-1,4-diazepin-1-yl group, a 3-azetidinyl group, a 3-dimethylamino-1-pyrrolidinyl group, a 3-(tert-butylamino)-1-pyrrolidinyl group, a 4-piperidyl group, a 1-methyl-4-piperidyl group, a 1-ethyl-4-piperidyl group, a 1-(2-hydroxyethyl)-4-piperidyl group, a 1-(2-methylsulfonylethyl)-4-piperidyl group, a 4-hydroxy-4-piperidyl group, a 4-hydroxy-1-methyl-4-piperidyl group, a 1-tert-butoxycarbonyl-4-hydroxy-4-piperidyl group, a 2-pyridylmethyl-(methyl)-amino group, a 1,2,3,6-tetrahydro-4-pyridyl group, a 1-(2-(dimethylamino)-ethyl)-pyrazolyl group, a 3-azetidinyloxy group, a 1-methyl-3-azetidinyloxy group, a 1-ethyl-3-azetidinyloxy group, a 1-propyl-3-azetidinyloxy group, a 1-isopropyl-3-azetidinyloxy group, a 1-(2-hydroxyethyl)-3-azetidinyloxy group, a 4-piperidyloxy group, a 1-methyl-4-piperidyloxy group, a 1-ethyl-4-piperidyloxy group, a 1-cyclobutyl-4-piperidyloxy group, a 2-dimethylaminoethoxy group, a 3-(dimethylamino)-propyl group, a dimethylaminomethyl group, a diethylaminomethyl group, a methylpropylaminomethyl group, an isopropylmethylaminomethyl group, a 2-dimethylamino-1-methylethoxy group, a 2-dimethylamino-propoxy group, a 3-dimethylamino-propoxy group, a 7-methyl-2,7-diazabicyclo[3.3.0]oct-2-yl group, a 2-methyl-2,7-diazabicyclo[3.3.0]oct-7-yl group, a 2-methyl-2,7-diazaspiro[4,5]dec-7-yl group, and a 2-methyl-2,7-diazaspiro[3.5]non-7-yl group. Preferable examples include a 4-methyl-1-piperazinyl group, a 4-(1-acetyl-3-azetidinyl)-1-piperazinyl group, a 4-(2-hydroxyethyl)-1-piperazinyl group, a 4-acetyl-1-piperazinyl group, a 4-methyl-2-methoxymethyl-1-piperazinyl group, a 4-(2-(dimethylamino)acetyl)-1-piperazinyl group, a morpholino group, a 3-(dimethylaminomethyl)-1-morpholino group, a 3-hydroxymethyl-1-morpholino group, a 3-dimethylamino-1-pyrrolidinyl group, a 3-(tert-butylamino)-1-pyrrolidinyl group, a 2-pyridylmethyl-(methyl)-amino group, a 1-(2-(dimethylamino)-ethyl)-pyrazolyl group, a 3-(dimethylamino)-propyl group, dimethylaminomethyl group, a 2-dimethylamino-1-methyl-ethoxy group, a 2-dimethylamino-propoxy group, a 3-dimethylamino-propoxy group, a 7-methyl-2,7-diazabicyclo[3.3.0]oct-2-yl group, a 2-methyl-2,7-diazabicyclo[3.3.0]oct-7-yl group, a 2-methyl-2,7-diazaspiro[4,5]dec-7-yl group, and a 2-methyl-2,7-diazaspiro[3.5]non-7-yl group. More preferable examples include a 4-methyl-1-piperazinyl group, a 4-methyl-(2-hydroxyethyl)-1-piperazinyl group, a 4-(2-(dimethylamino)acetyl)-1-piperazinyl group, a 3-(dimethylaminomethyl)-1-morpholino group, a 3-hydroxymethyl-1-morpholino group, and a 3-dimethylamino-1-pyrrolidinyl group.

Preferable examples of the substituent of $Ar^1$ include a C1-C6 alkyl group, a hydroxy-C1-C6 alkyl group, a C1-C6 alkoxy group, a C2-C7 alkanoyl group, and a group represented by $-Q^1-R^{1a}$.

In the optionally substituted aryl group represented by $Ar^1$, the "aryl group" itself is preferably a phenyl group, for example. In the optionally substituted heteroaryl group represented by $Ar^1$, the "heteroaryl group" itself is preferably a pyrazolyl group, or a pyridyl group, for example.

That is, Ar¹ is preferably, for example, a phenyl, pyrazolyl or pyridyl group substituted with a group such as a C1-C6 alkyl group, a hydroxy-C1-C6 alkyl group, a C1-C6 alkoxy group, a C2-C7 alkanoyl group or a group represented by -Q¹-R¹ᵃ. More preferably, Ar¹ is a phenyl group substituted with one group represented by -Q¹-R¹ᵃ, or a phenyl group substituted with a C1-C6 alkyl group, a C1-C6 alkoxy group or a hydroxy-C1-C6 alkyl group, in addition to one group represented by -Q¹-R¹ᵃ, for example.

Specifically, preferable examples of Ar¹ include a phenyl group, a 4-hydroxymethyl-3-methylphenyl group, a 4-isopropyloxyphenyl group, a 4-acetylphenyl group, a 3,5-dimethyl-4-(2-dimethylaminoethoxy)phenyl group, a 4-(1-methyl-1H-pyrazol-4-yl)phenyl group, a 4-(1-piperazinyl)phenyl group, a 3-methyl-4-(1-piperazinyl)phenyl group, a 3-hydroxymethyl-4-(1-piperazinyl)phenyl group, a 4-(4-methyl-1-piperazinyl)phenyl group, a 3-methyl-4-(4-methyl-1-piperazinyl)phenyl group, a 3-hydroxymethyl-4-(4-methyl-1-piperazinyl)phenyl group, a 4-(4-ethyl-1-piperazinyl)phenyl group, a 4-(4-ethyl-1-piperazinyl)-3-hydroxymethylphenyl group, a 4-(4-isopropyl-1-piperazinyl)phenyl group, a 3-methyl-4-(4-isopropyl-1-piperazinyl)phenyl group, a 4-(4-tert-butyl-1-piperazinyl)phenyl group, a 4-(4-cyclopropyl-1-piperazinyl)phenyl group, a 4-(4-cyclopropyl-1-piperazinyl)-3-methylphenyl group, a 4-(4-cyclopropyl-1-piperazinyl)-3-hydroxymethylphenyl group, a 4-(4-cyclobutyl-1-piperazinyl)phenyl group, a 4-(4-cyclobutyl-1-piperazinyl)-3-methylphenyl group, a 4-(4-cyclopropylmethyl-1-piperazinyl)phenyl group, a 4-(4-cyclopropylmethyl-1-piperazinyl)-3-methylphenyl group, a 4-(4-(1-acetyl-3-azetidinyl)-1-piperazinyl)phenyl group, a 4-(4-(2-hydroxyethyl)-1-piperazinyl)phenyl group, a 4-(4-(2-hydroxyethyl)-1-piperazinyl)-3-methylphenyl group, a 4-(4-(2-methoxyethyl)-1-piperazinyl)phenyl group, a 3-methyl-4-(4-acetyl-1-piperazinyl)phenyl group, a 4-(4-(2-methoxyacetyl)-1-piperazinyl)phenyl group, a 3-hydroxymethyl-4-(4-(2-methoxyacetyl)-1-piperazinyl)phenyl group, a 4-(4-methyl-2-methoxymethyl-1-piperazinyl)phenyl group, a 4-(4-methylsulfonyl-1-piperazinyl)phenyl group, a 3-methyl-4-(4-methylsulfonyl-1-piperazinyl)phenyl group, a 4-(4-(2-(dimethylamino)acetyl)-1-piperazinyl)phenyl group, a 4-(4-methyl-3-oxo-1-piperazinyl)phenyl group, a 3-methyl-4-(4-methyl-3-oxo-1-piperazinyl)phenyl group, a 4-(4-hydroxypiperidino)phenyl group, a 4-(4-hydroxypiperidino)-3-methylphenyl group, a 4-(4-hydroxypiperidino)-3-hydroxymethylphenyl group, a 4-morpholinophenyl group, a 3-methyl-4-morpholinophenyl group, a 3-hydroxymethyl-4-morpholinophenyl group, a 4-(3-(dimethylaminomethyl)-1-morpholino)phenyl group, a 4-(3-hydroxymethyl-1-morpholino)phenyl group, a 4-(1,1-dioxidothiomorpholino)phenyl group, a 3-methyl-4-(1,1-dioxidothiomorpholino)phenyl group, a 4-(4-methyl-5-oxo-perhydro-1H-1,4-diazepin-1-yl)phenyl group, a 4-(3-hydroxymethyl-3-dimethylamino-1-pyrrolidinyl)phenyl group, a 4-(3-(tert-butylamino)-1-pyrrolidinyl)phenyl group, a 4-(4-piperidyl)phenyl group, a 4-(1-methyl-4-piperidyl)phenyl group, a 3-methyl-4-(4-piperidyl)phenyl group, a 4-(4-hydroxy-4-piperidyl)phenyl group, a 4-(4-hydroxy-1-methyl-4-piperidyl)phenyl group, a 4-(1-(2-hydroxyethyl)-4-piperidyl)phenyl group, a 4-(1-(2-hydroxyethyl)-4-piperidyl)-3-methylphenyl group, a 4-(1-tert-butoxycarbonyl-4-hydroxy-4-piperidyl)phenyl group, a 4-(2-pyridylmethyl-(methyl)-amino)phenyl group, a 4-(1,2,3,6-tetrahydro-4-pyridyl)phenyl group, a 3-methyl-4-(1,2,3,6-tetrahydro-4-pyridyl)phenyl group, a 4-(1-(2-(dimethylamino)-ethyl)-pyrazolyl)phenyl group, a 4-(3-azetidinyloxy)phenyl group, a 4-(3-azetidinyloxy)-3-methylphenyl group, a 4-(1-ethyl-3-azetidinyloxy)phenyl group, a 4-(1-ethyl-3-azetidinyloxy)-3-methylphenyl group, a 4-(1-isopropyl-3-azetidinyloxy)phenyl group, a 4-(1-isopropyl-3-azetidinyloxy)-3-methylphenyl group, a 4-(1-(2-hydroxyethyl)-3-azetidinyloxy)phenyl group, a 4-(1-(2-hydroxyethyl)-3-azetidinyloxy)-3-methylphenyl group, a 4-(3-(dimethylamino)-propyl)phenyl group, a 4-(dimethylaminomethyl)phenyl group, a 4-(2-dimethylamino-1-methyl-ethoxy)phenyl group, a 4-(2-dimethylamino-propoxy)phenyl group, a 3-(3-dimethylamino-propoxy)-4-methoxyphenyl group, a 4-(7-methyl-2,7-diazabicyclo[3.3.0]oct-2-yl)phenyl group, a 4-(2-methyl-2,7-diazabicyclo[3.3.0]oct-7-yl)phenyl group, a 4-(2-methyl-2,7-diazaspiro[4,5]dec-7-yl)phenyl group, and a 4-(2-methyl-2,7-diazaspiro[3.5]non-7-yl)phenyl group. More preferable examples include a 4-(4-methyl-1-piperazinyl)phenyl group, a 3-methyl-4-(4-methyl-1-piperazinyl)phenyl group, a 4-(4-(1-acetyl-3-azetidinyl)-1-piperazinyl)phenyl group, a 4-(4-(2-hydroxyethyl)-1-piperazinyl)phenyl group, a 3-methyl-4-(4-acetyl-1-piperazinyl)phenyl group, a 4-(4-methyl-2-methoxymethyl-1-piperazinyl)phenyl group, a 4-(4-(2-(dimethylamino)acetyl)-1-piperazinyl)phenyl group, a 4-morpholinophenyl group, a 3-methyl-4-morpholinophenyl group, a 3-hydroxymethyl-4-morpholinophenyl group, a 4-(3-(dimethylaminomethyl)-1-morpholino)phenyl group, a 4-(3-hydroxymethyl-1-morpholino)phenyl group, a 4-(3-hydroxymethyl-3-dimethylamino-1-pyrrolidinyl)phenyl group, a 4-(3-(tert-butylamino)-1-pyrrolidinyl)phenyl group, a 4-(2-pyridylmethyl-(methyl)-amino)phenyl group, a 4-(1-(2-(dimethylamino)-ethyl)-pyrazolyl)phenyl group, a 4-(3-(dimethylamino)-propyl)phenyl group, a 4-(dimethylaminomethyl)phenyl group, a 4-(2-dimethylamino-1-methyl-ethoxy)phenyl group, a 4-(2-dimethylamino-propoxy)phenyl group, a 3-(3-dimethylamino-propoxy)-4-methoxyphenyl group, a 4-(7-methyl-2,7-diazabicyclo[3.3.0]oct-2-yl)phenyl group, a 4-(2-methyl-2,7-diazabicyclo[3.3.0]oct-7-yl)phenyl group, a 4-(2-methyl-2,7-diazaspiro[4,5]dec-7-yl)phenyl group, and a 4-(2-methyl-2,7-diazaspiro[3.5]non-7-yl)phenyl group. Even more preferable examples include a 4-(4-methyl-1-piperazinyl)phenyl group, a 3-methyl-4-(4-methyl-1-piperazinyl)phenyl group, a 4-(4-(2-hydroxyethyl)-1-piperazinyl)phenyl group, a 4-(4-(2-(dimethylamino)acetyl)-1-piperazinyl)phenyl group, a 4-(3-(dimethylaminomethyl)-1-morpholino)phenyl group, a 4-(3-hydroxymethyl-1-morpholino)phenyl group, and a 4-(3-hydroxymethyl-3-dimethylamino-1-pyrrolidinyl)phenyl group.

R¹ is a hydrogen atom; a C1-C6 alkyl group which may have a substituent selected from the group consisting of a halogen atom, a hydroxyl group, a cyano group, a C1-C6 alkoxy group, a C3-C6 cycloalkyl group, a C2-C7 alkanoyl group and a C1-C6 alkylsulfonyl group; or an aryl, aralkyl or heteroaryl group which may have a substituent selected from the group consisting of a halogen atom, a hydroxyl group, a cyano group, an amino group, a C1-C6 alkyl group, a C1-C6 alkoxy group, a halo-C1-C6 alkyl group and a hydroxy-C1-C6 alkyl group.

The "C1-C6 alkyl group which may have a substituent selected from the group consisting of a halogen atom, a hydroxyl group, a cyano group, a C1-C6 alkoxy group, a C3-C6 cycloalkyl group, a C2-C7 alkanoyl group and a C1-C6 alkylsulfonyl group" for R¹ means the C1-C6 alkyl group as defined above, either unsubstituted or substituted with a substituent selected from the group consisting of a halogen atom, a hydroxyl group, a cyano group, a C1-C6 alkoxy group, a C3-C6 cycloalkyl group, a C2-C7 alkanoyl group and a C1-C6 alkylsulfonyl group. One or two or more, preferably 1 to 3 substituents may be the same or different and may substitute at arbitrary available substitution positions of each group.

Preferable examples of the substituent halogen atom include a fluorine atom, and a chlorine atom.

Preferable examples of the substituent C1-C6 alkyl group include a methyl group, and an ethyl group.

Preferable examples of the "C1-C6 alkyl group which may have a substituent selected from the group consisting of a halogen atom, a hydroxyl group, a cyano group, a C1-C6 alkoxy group, a C3-C6 cycloalkyl group, a C2-C7 alkanoyl group and a C1-C6 alkylsulfonyl group" for $R^1$ include a methyl group, an ethyl group, a propyl group, an isopropyl group, a 2,2-difluoroethyl group, and a 2,2,2-trifluoroethyl group.

The "aryl, aralkyl, or heteroaryl group which may have a substituent selected from the group consisting of a halogen atom, a hydroxyl group, a cyano group, an amino group, a C1-C6 alkyl group, a C1-C6 alkoxy group, a halo-C1-C6 alkyl group and a hydroxy-C1-C6 alkyl group" for $R^1$ means the aryl, aralkyl or heteroaryl group as defined above, either unsubstituted or substituted at arbitrary available substitution positions. The substituent, selected from the group consisting of a halogen atom, a hydroxyl group, a cyano group, an amino group, a C1-C6 alkyl group, a C1-C6 alkoxy group, a halo-C1-C6 alkyl group and a hydroxy-C1-C6 alkyl group, may be the same or different, and one or two or more, preferably 1 or 2 substituents may be selected.

Preferable examples of the substituent halogen atom include a fluorine atom, and a chlorine atom.

Preferable examples of the substituent C1-C6 alkyl group include a methyl group, and an ethyl group.

Preferable examples of the optionally substituted aryl group represented by $R^1$ include a phenyl group, a 1-naphthyl group, a 2-chlorophenyl group, a 2,6-dichlorophenyl group, a 2-cyanophenyl group, and a 2-chloro-6-cyanophenyl group.

Preferable examples of the optionally substituted heteroaryl group represented by $R^1$ include a 2-pyridyl group, and a 3-chloro-2-pyridyl group.

Preferable examples of the optionally substituted aralkyl group represented by $R^1$ include a benzyl group, and an α-methylbenzyl group.

The preferable form of $R^1$ is, for example, a hydrogen atom, or a C1-C6 alkyl group which may be substituted with a halogen atom or a hydroxyl group.

Specifically, preferable examples include a hydrogen atom, a methyl group, an ethyl group, and a 2-hydroxyethyl group. More preferable examples include a hydrogen atom, a methyl group, a 2-hydroxyethyl group. Even more preferable examples include a hydrogen atom, and a methyl group.

$R^2$ is an aryl, aralkyl or heteroaryl group which may have a substituent selected from the group consisting of a halogen atom, a hydroxyl group, a cyano group, an amino group, a nitro group, a carbamoyl group, a C1-C6 alkyl group, a C1-C6 alkoxy group, a C1-C6 alkylsulfonyl group, a halo-C1-C6 alkyl group, a hydroxy-C1-C6 alkyl group and a C1-C6 alkoxy-C1-C6 alkyl group.

The "aryl, aralkyl or heteroaryl group which have a substituent selected from the group consisting of a halogen atom, a hydroxyl group, a cyano group, an amino group, a nitro group, a carbamoyl group, a C1-C6 alkyl group, a C1-C6 alkoxy group, a C1-C6 alkylsulfonyl group, a halo-C1-C6 alkyl group, a hydroxy-C1-C6 alkyl group and a C1-C6 alkoxy-C1-C6 alkyl group" for $R^2$ means the aryl, aralkyl or heteroaryl group as defined above, either unsubstituted or substituted at arbitrary available substitution positions. The substituent, selected from the group consisting of a halogen atom, a hydroxyl group, a cyano group, an amino group, a nitro group, a carbamoyl group, a C1-C6 alkyl group, a C1-C6 alkoxy group, a C1-C6 alkylsulfonyl group, a halo-C1-C6 alkyl group, a hydroxy-C1-C6 alkyl group and a C1-C6 alkoxy-C1-C6 alkyl group, may be the same or different, and one or two or more, preferably 1 to 3 substituents may be selected.

Preferable examples of the substituent include: halogen atoms such as a chlorine atom and a fluorine atom; cyano groups; C1-C6 alkyl groups such as a methyl group; C1-C6 alkoxy groups such as a methoxy group and an ethoxy group; halo-C1-C6 alkyl groups such as a trifluoromethyl group; and hydroxy-C1-C6 alkyl groups such as a hydroxymethyl group. More preferable examples include halogen atoms such as a chlorine atom and a fluorine atom; and C1-C6 alkyl groups such as a methyl group.

In the optionally substituted aryl group represented by $R^2$, the "aryl group" itself is preferably a phenyl, for example.

In the optionally substituted aralkyl group represented by $R^2$, the "aralkyl group" itself is preferably a benzyl, for example.

In the optionally substituted heteroaryl group represented by $R^2$, the "heteroaryl group" itself is preferably a pyridyl, for example.

An example of the preferable form of $R^2$ is the group represented by the following Formula (a):

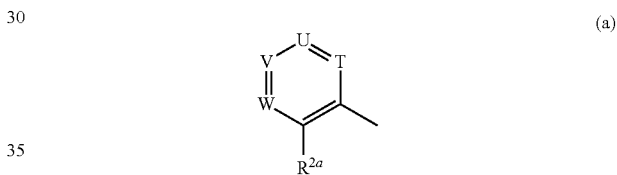

(a)

In the Formula, $R^{2a}$ is a halogen atom, a hydroxyl group, a cyano group, an amino group, a nitro group, a carbamoyl group, a C1-C6 alkyl group, a C1-C6 alkylsulfonyl group, a C1-C6 alkoxy group, a halo-C1-C6 alkyl group, a hydroxy-C1-C6 alkyl group and a C1-C6 alkoxy-C1-C6 alkyl group; T, U, V and W are a nitrogen atom, or a methine group which may be substituted with a halogen atom, a hydroxyl group, a cyano group, an amino group, a nitro group, a carbamoyl group, a C1-C6 alkyl group, a C1-C6 alkylsulfonyl group, a C1-C6 alkoxy group, a halo-C1-C6 alkyl group, a hydroxy-C1-C6 alkyl group or a C1-C6 alkoxy-C1-C6 alkyl group, wherein at least two of them are the methine groups. Preferably, $R^2$ is the group represented by Formula (a), $R^{2a}$ is a halogen atom, and T is a methine group substituted with a halogen atom or a C1-C6 alkyl group, for example.

Examples of the halogen atom represented by $R^{2a}$ include a fluorine atom, and a chlorine atom, preferably a chlorine atom.

Preferable examples of the C1-C6 alkyl group represented by $R^{2a}$ include a methyl group.

Preferable examples of the C1-C6 alkylsulfonyl group represented by $R^{2a}$ include a methylsulfonyl group.

Preferable examples of the C1-C6 alkoxy group represented by $R^{2a}$ include a methoxy group.

Preferable examples of the halo-C1-C6 alkyl group represented by $R^{2a}$ include a fluoromethyl group, and a trifluoromethyl.

Preferable examples of the hydroxy-C1-C6 alkyl group represented by $R^{2a}$ include a hydroxymethyl group.

Preferable examples of the C1-C6 alkoxy-C1-C6 alkyl group represented by $R^{2a}$ include a methoxymethyl group.

More preferably, $R^{2a}$ is a chlorine atom.

Preferable examples of T include: an unsubstituted methine group; a methine group substituted with a halogen atom such as a fluorine atom and a chlorine atom; a methine group substituted with a C1-C6 alkyl group such as a methyl group; and a methine group substituted with a halo-C1-C6 alkyl group such as a trifluoromethyl group. More preferably, T is a methine group substituted with a halogen atom such as a chlorine atom.

U, V and W are preferably unsubstituted methine groups.

Specifically, preferable examples of $R^2$ include a phenyl group, a 2-chlorophenyl group, a 2-fluorophenyl group, a 2,6-dichlorophenyl group, a 2-chloro-3-fluorophenyl group, a 2-chloro-4-fluorophenyl group, a 2-chloro-5-fluorophenyl group, a 2-chloro-6-fluorophenyl group, a 2,6-dichloro-4-fluorophenyl group, a 2-chloro-4,6-difluorophenyl group, a 2-chloro-4-methylphenyl group, a 2-chloro-6-methylphenyl group, a 2,6-dichloro-4-methylphenyl group, a 2-chloro-5-trifluoromethylphenyl group, a 2,6-dichloro-4-trifluoromethylphenyl group, a 2-cyanophenyl group, a 2-alkoxyphenyl group, a 2,6-dichloro-4-hydroxymethylphenyl group, and a 2,4-dichloro-3-pyridyl group. More preferable examples include a 2,6-dichlorophenyl group, a 2-chloro-6-fluorophenyl group, a 2,6-dichloro-4-fluorophenyl group, a 2-chloro-4,6-difluorophenyl group, a 2-chloro-6-methylphenyl group, and a 2,4-dichloro-3-pyridyl group. 2,6-Dichlorophenyl group is particularly preferable.

$R^3$ is a hydrogen atom or a C1-C6 alkyl group.

Preferable examples of the C1-C6 alkyl group represented by $R^3$ include a methyl group.

Preferably, $R^3$ is a hydrogen atom.

In one aspect, the present invention is preferably a compound represented by the following General Formula (I-1):

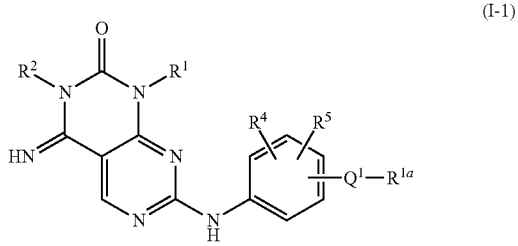

(I-1)

In the Formula, $Q^1$, $R^{1a}$, $R^1$ and $R^2$ are as defined above, and the preferable examples of $Q^1$, $R^{1a}$, $R^1$ and $R^2$ are as in Formula (I); $R^4$ and $R^5$ are independently a hydrogen atom, a halogen atom, a C1-C6 alkyl group, a halo-C1-C6 alkyl group, a hydroxy-C1-C6 alkyl group, a C1-C6 alkoxy group, a C2-C7 alkanoyl group, a hydroxy-C1-C6 alkylamino group, a carbamoyl group or a hydroxy-C1-C6 alkylcarbamoyl group.

Preferable examples of the halogen atom represented by $R^4$ or $R^5$ include a fluorine atom, and a chlorine atom.

Preferable examples of the C1-C6 alkyl group represented by $R^4$ or $R^5$ include a methyl group, and an ethyl group.

Preferable examples of the halo-C1-C6 alkyl group represented by $R^4$ or $R^5$ include a fluoromethyl group, a difluoromethyl group, and a trifluoromethyl group.

Preferable examples of the hydroxy-C1-C6 alkyl group represented by $R^4$ or $R^5$ include a hydroxymethyl group, and a 2-hydroxyethyl group.

Preferable examples of the C1-C6 alkoxy group represented by $R^4$ or $R^5$ include a methoxy group, and an ethoxy group.

Preferable examples of the C2-C7 alkanoyl group represented by $R^4$ or $R^5$ include an acetyl group.

Preferable examples of the hydroxy-C1-C6 alkylamino group represented by $R^4$ or $R^5$ include a hydroxymethylamino group, a 2-hydroxyethylamino group, a 1-hydroxy-1-methylethylamino group, a 1,2-dihydroxyethylamino group, and a 3-hydroxypropylamino group. More preferable examples include a hydroxymethylamino group, and a 2-hydroxyethylamino group.

Preferable examples of the hydroxy-C1-C6 alkylcarbamoyl group represented by $R^4$ or $R^5$ include a hydroxymethylcarbamoyl group, a 2-hydroxyethylcarbamoyl group, a 1-hydroxy-1-methylethylcarbamoyl group, a 1,2-dihydroxyethylcarbamoyl group, and a 3-hydroxypropylcarbamoyl group. More preferable examples include a hydroxymethylcarbamoyl group, and a 2-hydroxyethylcarbamoyl group.

Specific examples of $R^4$ or $R^5$ include a hydrogen atom, a fluorine atom, a chlorine atom, a methyl group, an ethyl group, a fluoromethyl group, a difluoromethyl group, a trifluoromethyl group, a hydroxymethyl group, a 2-hydroxyethyl group, a methoxy group, an ethoxy group, an acetyl group, a hydroxymethylamino group, a 2-hydroxyethylamino group, a 1-hydroxy-1-methylethylamino group, a 1,2-dihydroxyethylamino group, a 3-hydroxypropylamino group, a hydroxymethylcarbamoyl group, a 2-hydroxyethylcarbamoyl group, a 1-hydroxy-1-methylethylcarbamoyl group, a 1,2-dihydroxyethylcarbamoyl group, and a 3-hydroxypropylcarbamoyl group. More preferable examples include a hydrogen atom, a methyl group, a hydroxymethyl group, and a methoxy group. The hydrogen atom is particularly preferable.

When any variable (for example, $R^{1a}$) referring to a given member occurs more than once, its definition at each occurrence is meant to independently apply to all other occurrences. Further, a combination of substituents and variables is acceptable only when the combination leads to a stable compound. The line leading out from a substituent into a ring system means that the binding is possible with any of the cyclic atoms available for substitution.

The "arbitrary available substitution positions", as that term is used herein, refer to sites where a hydrogen atom available for substitution is present on carbon, nitrogen, oxygen and/or sulfur atoms, and at which substitution of the hydrogen atom is chemically acceptable and creates a stable compound.

In a compound of the present invention, the replacement of the methylene group constituting the C1-C6 alkylene group with, for example, oxygen, sulfur, sulfinyl, sulfonyl, carbonyl, vinylene, or substituted or unsubstituted imine is acceptable when the replacement is chemically acceptable and creates a stable compound.

A compound of the present invention, depending on the form of the substituent or its salt form, may exist as a stereoisomer, such as an optical isomer, a diastereomer, and a geometric isomer, or as a tautomer. A compound of the present invention is inclusive of all such stereoisomers, tautomers, and mixtures thereof.

The present invention is inclusive of various crystals, amorphous forms, salts, hydrates, and solvates of a compound of the present invention.

A prodrug of a compound of the present invention also falls within the scope of the present invention. Generally, such a prodrug is a functional derivative of a compound of the present invention, easily convertible into a compound required in the body. Accordingly, in the treatment of various diseases according to the present invention, the term "administration" encompasses not only the administration of a specific compound but the administration of a compound that converts into a specific compound in the body after being given to a patient. Conventional methods for the selection and production of a suitable prodrug derivative are described in, for example, *Design of Prodrugs*, ed. H. Bundgaard, Elsevier, 1985, the entire disclosure of which is hereby incorporated herein by reference. The metabolites of these compounds are inclusive of active compounds produced from a compound of the present invention in a biological environment, and such metabolites also fall within the scope of the present invention.

Specific examples of the compound represented by General Formula (I), and a salt or N-oxide derivative thereof include compounds described in Examples, and salts or N-oxide derivatives thereof. Preferable examples include:

(1) 3-(2,6-dichlorophenyl)-7-({4-[4-(2-hydroxyethyl)piperazin-1-yl]phenyl}amino)-4-imino-1-methyl-3,4-dihydropyrimido[4,5-d]pyrimidin-2(1H)-one;
(2) 3-(2,6-dichlorophenyl)-7-({4-[2-(hydroxymethyl)morpholin-4-yl]phenyl}amino)-4-imino-1-methyl-3,4-dihydropyrimido[4,5-d]pyrimidin-2(1H)-one;
(3) 3-(2,6-dichlorophenyl)-7-[(4-{4-[(dimethylamino)acetyl]piperazin-1-yl}phenyl)amino]-4-imino-1-methyl-3,4-dihydropyrimido[4,5-d]pyrimidin-2(1H)-one;
(4) 3-(2,6-dichlorophenyl)-7-[(4-{2-[(dimethylamino)methyl]morpholin-4-yl}phenyl)amino]-4-imino-1-methyl-3,4-dihydropyrimido[4,5-d]pyrimidin-2(1H)-one;
(5) 3-(2,6-dichlorophenyl)-4-imino-7-{[4-(4-methylpiperazin-1-yl)phenyl]amino}-3,4-dihydropyrimido[4,5-d]pyrimidin-2(1H)-one;
(6) 3-(2,6-dichlorophenyl)-4-imino-7-{[3-methyl-4-(4-methylpiperazin-1-yl)phenyl]amino}-3,4-dihydropyrimido[4,5-d]pyrimidin-2(1H)-one;
(7) 3-(2,6-dichlorophenyl)-4-imino-1-methyl-7-{[4-(4-methylpiperazin-1-yl)phenyl]amino}-3,4-dihydropyrimido[4,5-d]pyrimidin-2(1H)-one;
(8) 3-(2,6-dichlorophenyl)-7-({4-[(3R)-3-dimethylaminopyrrolidin-1-yl]phenyl}amino)-4-imino-3,4-dihydropyrimido[4,5-d]pyrimidin-2(1H)-one;
(9) 3-(2,6-dichlorophenyl)-4-imino-7-{[4-(5-methylhexahydropyrrolo[3,4-b]pyrrol-1(2H)-yl)phenyl]amino}-3,4-dihydropyrimido[4,5-d]pyrimidin-2(1H)-one;
(10) 3-(2,6-dichlorophenyl)-4-imino-7-{[4-(2-methyl-2,7-diazaspiro[4,5]dec-7-yl)phenyl]amino}-3,4-dihydropyrimido[4,5-d]pyrimidin-2(1H)-one;
(11) 3-(2,6-dichlorophenyl)-4-imino-7-[4-(1-methylhexahydropyrrolo[3,4-b]pyrrol-5(1H)-yl)phenyl]amino-3,4-dihydropyrimido[4,5-d]pyrimidin-2(1H)-one;
(12) 3-(2,6-dichlorophenyl)-4-imino-7-({4-[(2R)-2-(methoxymethyl)-4-methylpiperazin-1-yl]phenyl}amino)-3,4-dihydropyrimido[4,5-d]pyrimidin-2(1H)-one;
(13) 7-({4-[3-(tert-butylamino)pyrrolidin-1-yl]phenyl}amino)-3-(2,6-dichlorophenyl)-4-imino-3,4-dihydropyrimido[4,5-d]pyrimidin-2(1H)-one;
(14) 3-(2,6-dichlorophenyl)-7-({4-[(3S)-3-(dimethylamino)pyrrolidin-1-yl]phenyl}amino)-4-imino-3,4-dihydropyrimido[4,5-d]pyrimidin-2(1H)-one;
(15) 7-{[4-(4-acetylpiperazin-1-yl)-3-methylphenyl]amino}-3-(2,6-dichlorophenyl)-4-imino-3,4-dihydropyrimido[4,5-d]pyrimidin-2(1H)-one;
(16) 3-(2,6-dichlorophenyl)-4-imino-7-{[4-(2-methyl-2,7-diazaspiro[3,5]non-7-yl)phenyl]amino}-3,4-dihydropyrimido[4,5-d]pyrimidin-2(1H)-one;
(17) 7-({-4-[4-(1-acetylazetidin-3-yl)piperazin-1-yl]phenyl}amino)-3-(2,6-dichlorophenyl)-4-imino-1-methyl-3,4-dihydropyrimido[4,5-d]pyrimidin-2(1H)-one;
(18) 3-(2,6-dichlorophenyl)-4-imino-7-{[4-(morpholin-4-yl)phenyl]amino}-3,4-dihydropyrimido[4,5-d]pyrimidin-2(1H)-one;
(19) 3-(2,6-dichlorophenyl)-7-({4-[2-(dimethylamino)-1-methylethoxy]phenyl}amino)-4-imino-3,4-dihydropyrimido[4,5-d]pyrimidin-2(1H)-one;
(20) 3-(2,6-dichlorophenyl)-4-imino-7-({4-[methyl(pyridin-2-ylmethyl)amino]phenyl}amino)-3,4-dihydropyrimido[4,5-d]pyrimidin-2(1H)-one;
(21) 3-(2,6-dichlorophenyl)-7-({4-[4-(2-hydroxyethyl)piperazin-1-yl]phenyl}amino)-4-imino-3,4-dihydropyrimido[4,5-d]pyrimidin-2(1H)-one;
(22) 3-(2,6-dichlorophenyl)-7-({4-[2-(dimethylamino)propoxy]phenyl}amino)-4-imino-3,4-dihydropyrimido[4,5-d]pyrimidin-2(1H)-one;
(23) 3-(2,6-dichlorophenyl)-7-[(4-{2-[(dimethylamino)methyl]morpholin-4-yl}phenyl)amino]-4-imino-3,4-dihydropyrimido[4,5-d]pyrimidin-2(1H)-one;
(24) 3-(2,6-dichlorophenyl)-7-({3-[3-(dimethylamino)propoxy]-4-methoxyphenyl}amino)-4-imino-3,4-dihydropyrimido[4,5-d]pyrimidin-2(1H)-one;
(25) 3-(2,6-dichlorophenyl)-7-({4-[(dimethylamino)methyl]phenyl}amino)-4-imino-3,4-dihydropyrimido[4,5-d]pyrimidin-2(1H)-one;
(26) 3-(2,6-dichlorophenyl)-7-({4-[3-(dimethylamino)-3-(hydroxymethyl)pyrrolidin-1-yl]phenyl}amino)-4-imino-3,4-dihydropyrimido[4,5-d]pyrimidin-2(1H)-one;
(27) 3-(2,6-dichlorophenyl)-7-[(4-{1-[2-(dimethylamino)ethyl]-1H-pyrazol-4-yl}phenyl)amino]-4-imino-3,4-dihydropyrimido[4,5-d]pyrimidin-2(1H)-one; and
(28) 3-(2,6-dichlorophenyl)-1-(2-hydroxyethyl)-4-imino-7-{[4-(4-methylpiperazin-1-yl)phenyl]amino}-3,4-dihydropyrimido[4,5-d]pyrimidin-2(1H)-one.

More preferable examples include:

(1) 3-(2,6-dichlorophenyl)-7-({4-[4-(2-hydroxyethyl)piperazin-1-yl]phenyl}amino)-4-imino-1-methyl-3,4-dihydropyrimido[4,5-d]pyrimidin-2(1H)-one;
(2) 3-(2,6-dichlorophenyl)-7-({4-[2-(hydroxymethyl)morpholin-4-yl]phenyl}amino)-4-imino-1-methyl-3,4-dihydropyrimido[4,5-d]pyrimidin-2(1H)-one;
(3) 3-(2,6-dichlorophenyl)-7-[(4-{4-[(dimethylamino)acetyl]piperazin-1-yl}phenyl)amino]-4-imino-1-methyl-3,4-dihydropyrimido[4,5-d]pyrimidin-2(1H)-one;
(4) 3-(2,6-dichlorophenyl)-7-[(4-{2-[(dimethylamino)methyl]morpholin-4-yl}phenyl)amino]-4-imino-1-methyl-3,4-dihydropyrimido[4,5-d]pyrimidin-2(1H)-one;
(5) 3-(2,6-dichlorophenyl)-4-imino-7-{[4-(4-methylpiperazin-1-yl)phenyl]amino}-3,4-dihydropyrimido[4,5-d]pyrimidin-2(1H)-one;
(6) 3-(2,6-dichlorophenyl)-4-imino-7-{[3-methyl-4-(4-methylpiperazin-1-yl)phenyl]amino}-3,4-dihydropyrimido[4,5-d]pyrimidin-2(1H)-one;
(7) 3-(2,6-dichlorophenyl)-4-imino-1-methyl-7-{[4-(4-methylpiperazin-1-yl)phenyl]amino}-3,4-dihydropyrimido[4,5-d]pyrimidin-2(1H)-one; and
(8) 3-(2,6-dichlorophenyl)-7-({4-[(3R)-3-dimethylaminopyrrolidin-1-yl]phenyl}amino)-4-imino-3,4-dihydropyrimido[4,5-d]pyrimidin-2(1H)-one.

A producing method of a compound according to the present invention is described below.

A compound (I) of the present invention can be produced, for example, by producing methods described below, and by methods described in Examples and Production Examples. It should be noted, however, that a producing method of a compound (I) of the present invention is not limited to the reaction examples below.

Producing Method 1

The compound represented by General Formula (I), or an N-oxide derivative thereof can be produced by causing a reaction between a compound of General Formula (II) and a compound or a salt thereof represented by General Formula (III), so as to obtain a compound represented by General Formula (IV):

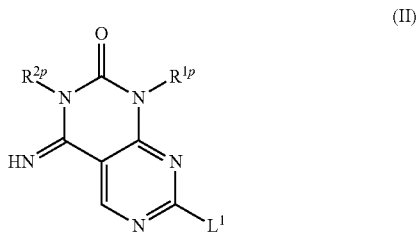

(II)

In the Formula, $R^{1p}$ is a hydrogen atom; a C1-C6 alkyl group which may have a substituent selected from the group consisting of a halogen atom, a protected or unprotected hydroxyl group, a cyano group, a C1-C6 alkoxy group, a C3-C6 cycloalkyl group, a C2-C7 alkanoyl group and a C1-C6 alkylsulfonyl group; or an aryl, aralkyl or heteroaryl group which may have a substituent selected from the group consisting of a halogen atom, a protected or unprotected hydroxyl group, a cyano group, an protected or unprotected amino group, a C1-C6 alkyl group, a C1-C6 alkoxy group, a halo-C1-C6 alkyl group and a protected or unprotected hydroxy-C1-C6 alkyl group;

$R^{2p}$ is an aryl, aralkyl or heteroaryl group which may have a substituent selected from the group consisting of a halogen atom, a protected or unprotected hydroxyl group, a cyano group, a protected or unprotected amino group, a nitro group, a carbamoyl group, a C1-C6 alkyl group, a C1-C6 alkoxy group, a C1-C6 alkylsulfonyl group, a halo-C1-C6 alkyl group, a protected or unprotected hydroxy-C1-C6 alkyl group and a C1-C6 alkoxy-C1-C6 alkyl group; and $L^1$ is an elimination group.

(III)

In the Formula, $Ar^{1p}$ is an aryl or heteroaryl group which may have a substituent selected from the group consisting of a halogen atom, a C1-C6 alkyl group, a halo-C1-C6 alkyl group, a protected or unprotected hydroxy-C1-C6 alkyl group, a C1-C6 alkoxy group, a C2-C7 alkanoyl group, a protected or unprotected hydroxy-C1-C6 alkylamino group, a carbamoyl group, a protected or unprotected hydroxy-C1-C6 alkylcarbamoyl group and a group represented by -$Q^{1p}$-$R^{1ap}$;

$Q^{1p}$ is a single bond, or a C1-C6 alkylene group, in which one or two or more methylene groups constituting the C1-C6 alkylene group may be independently replaced with an oxygen atom, a sulfur atom, a protected or unprotected carbonyl group, a protected or unprotected imino group, a sulfinyl group or a sulfonyl group, and may be substituted with a halogen atom, a cyano group, a protected or unprotected hydroxyl group, a C1-C6 alkyl group or an C1-C6 alkoxy group;

$R^{1a}$ is a hydrogen atom, a protected or unprotected hydroxyl group, a formyl group, a C1-C6 alkyl group, a di-C1-C6 alkylamino group, a protected or unprotected hydroxy-C1-C6 alkyl group or a carboxyphenyl group, or a heterocyclic group, including at least one nitrogen atom as a heteroatom in the heterocycle, and which may have a substituent selected from the group consisting of a halogen atom, a protected or unprotected hydroxyl group, an oxo group, a C1-C6 alkyl group, a C1-C6 alkoxy group, a protected or unprotected hydroxy-C1-C6 alkyl group, a C1-C6 alkoxy-C1-C6 alkyl group and a group represented by —$R^{1bp}$;

$R^{1bp}$ is a group represented by -$Q^{2p}$-$A^{1p}$($R^{1cp}$)$R^{1dp}$;

$Q^{2p}$ is a single bond, or a C1-C6 alkylene group, in which one or two or more methylene groups constituting the C1-C6 alkylene group may be independently replaced with an oxygen atom, a sulfur atom, a protected or unprotected carbonyl group, a protected or unprotected imino group, a sulfinyl group or a sulfonyl group, and may be substituted with a halogen atom, a cyano group, a protected or unprotected hydroxyl group, a protected or unprotected imino group, a C1-C6 alkyl group or a C1-C6 alkoxy group;

$A^{1p}$ is a nitrogen atom, or a methine group which may be substituted with a protected or unprotected hydroxyl group, a C1-C6 alkyl group, or a protected or unprotected hydroxy-C1-C6 alkyl group;

$R^{1cp}$ and $R^{1dp}$ are independently a hydrogen atom, a protected or unprotected carboxyl group, a C1-C6 alkyl group, or a protected or unprotected hydroxy-C1-C6 alkyl group, or together represent a C1-C6 alkylene group, in which one or two or more methylene groups constituting the C1-C6 alkylene group may be independently replaced with an oxygen atom, a sulfur atom, a sulfinyl group, a sulfonyl group, a protected or unprotected carbonyl group, a vinylene group or a group represented by —N($R^{1ep}$)—, and may be substituted with a protected or unprotected hydroxyl group, a C1-C6 alkyl group, or a protected or unprotected hydroxy-C1-C6 alkyl group;

$R^{1ep}$ is a protective group of the imino group, or a hydrogen atom, a formyl group, an acetyl group or a C1-C6 alkyl group; and $R^3$ is a hydrogen atom or a C1-C6 alkyl group.

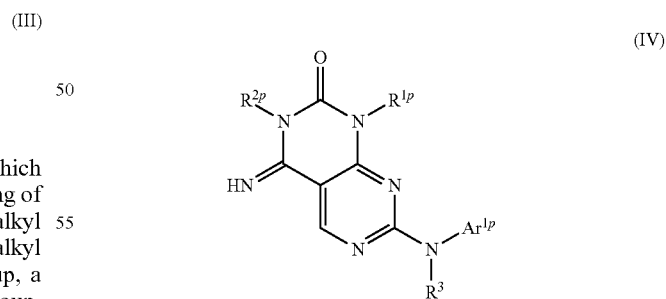

(IV)

In the Formula, $Ar^{1p}$, $R^{1p}$, $R^{2p}$ and $R^3$ are as defined above. When the compound (IV) includes a protective group of the amino group, imino group, hydroxyl group or carbonyl group, the method includes suitably selecting and performing the step of:

(1) removing the protective group; or (2) oxidizing the nitrogen atom of the compound, when the target compound is an N-oxide derivative.

When the compound of General Formula (IV) does not include a protective group of the amino group, imino group, hydroxyl group and carbonyl group, compound (IV) represents the compound of General Formula (I).

Examples of the elimination group represented by $L^1$ include halogen atoms such as a fluorine atom, a chlorine atom, a bromine atom and an iodine atom; organic sulfonyl groups such as a methylsulfinyl group, a methylsulfonyl group, an ethylsulfonyl group and a phenylsulfonyl group; and organic sulfonyloxy groups such as a methylsulfonyloxy group, a trifluoromethylsulfonyloxy group and a p-tolylsulfonyloxy group. Preferable examples include a chlorine atom, a methylsulfinyl group and a methylsulfonyl group.

The producing method is a general producing method of a compound represented by General Formula (I).

When the reactants of the reaction include groups, such as an amino group, an imino group, a hydroxyl group and a carbonyl group, not involved in the reaction, the reaction may be performed after appropriately protecting such an amino group, imino group, hydroxyl group and carbonyl group with the protective group of the amino group or the imino group, the protective group of the hydroxyl group or the protective group of the carbonyl group. The protective group may be removed after the reaction.

The protective group of the amino group or the imino group is not particularly limited, as long as it functions as intended. Examples include aralkyl groups such as a benzyl group, a p-methoxybenzyl group, a 3,4-dimethoxybenzyl group, an o-nitrobenzyl group, a p-nitrobenzyl group, a benzhydryl group, and a trityl group; lower alkanoyl groups such as a formyl group, an acetyl group, a propionyl group, a butyryl group, and a pivaloyl group; benzoyl groups; arylalkanoyl groups such as a phenylacetyl group, and a phenoxyacetyl group; lower alkoxycarbonyl groups such as a methoxycarbonyl group, an ethoxycarbonyl group, a propyloxycarbonyl group, and a tert-butoxycarbonyl group; aralkyloxycarbonyl groups such as a benzyloxycarbonyl group, a p-nitrobenzyloxycarbonyl group, and a phenethyloxycarbonyl group; lower alkylsilyl groups such as a trimethylsilyl group, and a tert-butyldimethylsilyl group; tetrahydropyranyl groups; trimethylsilylethoxymethyl groups; lower alkylsulfonyl groups such as a methylsulfonyl group, and an ethylsulfonyl group; and arylsulfonyl groups such as a benzenesulfonyl group, and a toluenesulfonyl group. Preferable examples include an acetyl group, a benzoyl group, a tert-butoxycarbonyl group, a trimethylsilylethoxymethyl group, and a methylsulfonyl group.

The protective group of the hydroxyl group is not particularly limited, as long as it functions as intended. Examples include lower alkyl groups such as a methyl group, an ethyl group, a propyl group, an isopropyl group, and a tert-butyl group; lower alkylsilyl groups such as a trimethylsilyl group, and a tert-butyldimethylsilyl group; lower alkoxymethyl groups such as a methoxymethyl group, and a 2-methoxyethoxymethyl group; tetrahydropyranyl groups; trimethylsilylethoxymethyl groups; aralkyl groups such as a benzyl group, a p-methoxybenzyl group, a 2,3-dimethoxybenzyl group, an o-nitrobenzyl group, a p-nitrobenzyl group, and a trityl group; and acyl groups such as a formyl group, and an acetyl group. Preferable examples include a methyl group, a methoxymethyl group, a tetrahydropyranyl group, a trityl group, a trimethylsilylethoxymethyl group, a tert-butyldimethylsilyl group, and an acetyl group.

The protective group of the carbonyl group is not particularly limited, as long as it functions as intended. Examples include acetals and ketals, such as ethylene ketal, trimethylene ketal, and dimethyl ketal.

The reaction between the compound of General Formula (II) and the compound of General Formula (III) is generally performed using an equal to excess moles, preferably an equal to 1.5 moles of compound (III) with respect to 1 mole of compound (II).

The reaction is generally performed in an inert solvent not detrimental to the reaction. Examples of the inert solvent include: nonpolar solvents of aromatic hydrocarbons such as toluene, benzene, and xylene; polar solvents such as methylene chloride, chloroform, tetrahydrofuran, dioxane, dimethylformamide, N-methylpyrrolidone, and dimethyl sulfoxide; alcoholic polar solvents such as methanol, ethanol, butanol, and isopropanol; and mixed solvents of these.

Preferably, the reaction is performed in the presence of a base or an acid.

Examples of the acid usable in the invention include: inorganic acids such as hydrochloric acid, sulfuric acid, nitric acid, phosphoric acid, and perchloric acid; organic acids such as maleic acid, fumaric acid, tartaric acid, citric acid, ascorbic acid, and trifluoroacetic acid; sulfonic acids such as methanesulfonic acid, isethionic acid, benzenesulfonic acid, and p-toluenesulfonic acid; and Lewis acids such as hafnium trifluoromethanesulfonate, ytterbium trifluoromethanesulfonate, and scandium trifluoromethanesulfonate. Preferable examples include p-toluenesulfonic acid, and hafnium trifluoromethanesulfonate.

The amount of acid used is generally 0.01 to excess moles, preferably 0.02 to 1.5 moles with respect to 1 mole of the compound represented by General Formula (II).

Examples of the base usable in the invention include: organic bases such as triethylamine, diisopropylethylamine, pyridine, and 4-dimethylaminopyridine; and inorganic bases such as sodium bicarbonate, sodium carbonate, potassium carbonate, cesium carbonate, sodium hydroxide, and potassium hydroxide.

The amount of base used is generally an equal to excess moles, preferably 1 to 3 moles with respect to 1 mole of the compound represented by General Formula (II).

The reaction temperature is generally from 0° C. to 200° C., preferably 20° C. to 150° C.

The reaction time is generally from 5 minutes to 7 days, preferably 30 minutes to 24 hours.

A crude product of the compound represented by General Formula (N) can be obtained following a common process performed after the reaction. The compound of General Formula (I) or an N-oxide derivative thereof can then be produced from the compound of General Formula (N) so obtained, after purification using an ordinary method, or without purification. When the compound (N) has a protective group of the amino group, imino group, hydroxyl group or carbonyl group, this is followed by suitably selecting and performing the step of:

(1) removing the protective group; or
(2) oxidizing the nitrogen atom of the compound, when the target compound is an N-oxide derivative.

The method of removing the protective group, though it depends on the type of the protective group and the stability and other properties of the target compound (I), can be performed by appropriately combining the removal reactions of the protective groups of the amino group, hydroxyl group, and carbonyl group. For example, the protective group may be removed by solvolysis using an acid or a base, according to methods described in literature [see, for example, *Protective Groups in Organic Synthesis,* 3rd Ed., T. W. Greene, John Wiley & Sons, 1999], or similar methods; specifically, a method employing 0.01 moles to a large excess of an acid, preferably such as trifluoroacetic acid, formic acid, or hydrochloric acid, or an equimolar amount to a large excess of a base, preferably such as potassium hydroxide or calcium hydroxide. As another example, the method of removal may employ chemical reduction using compounds such as a hydrogenated metal complex, or catalytic reduction using catalysts such as palladium-carbon catalyst, and Raney nickel catalyst.

The step of oxidizing the nitrogen atom to produce an N-oxide derivative is performed using oxidizing agents, for example, such as m-chloroperbenzoic acid, dioxirane, sodium periodate, and hydrogen peroxide.

The amount of oxidizing agent used is generally 0.5 moles to excess moles, preferably 1 to 5 moles with respect to 1 mole of the compound represented by General Formula (N).

The reaction is generally performed in a solvent appropriately selected according to the oxidizing agent used for the reaction. For example, when the oxidizing agent is m-chloroperbenzoic acid, solvents such as methylene chloride and chloroform are preferable. When using dioxirane as the oxidizing agent, solvents such as acetone and water are preferably used.

The reaction temperature is generally from −50° C. to 100° C., preferably −20° C. to 50° C.

The reaction time is generally from 15 minutes to 7 days, preferably 30 minutes to 24 hours.

The compound of General Formula (I) or an N-oxide derivative thereof can easily be isolated and purified using common separation means, for example, such as solvent extraction, recrystallization, column chromatography, and preparative thin-layer chromatography.

The compound can be turned into a pharmaceutically acceptable salt using an ordinary method. The conversion from the salt to a free compound can also be performed according to an ordinary method.

As the term is used herein, the "salt" of the compound represented by General Formula (III) means a common salt used in the field of organic chemistry. When an amino group or a basic heterocyclic group is employed, the salt may be, for example, an acid addition salt formed at the amino group or the basic heterocyclic group.

Examples of the acid addition salt include: inorganic acid salts such as hydrochloride, sulfate, nitrate, phosphate, and perchlorate; organic acid salts such as maleate, fumarate, tartrate, citrate, ascorbate, and trifluoroacetate; and sulfonates such as methanesulfonate, isethionate, benzenesulfonate, and p-toluenesulfonate.

The compound represented by General Formula (II) or (III) may be obtained from, for example, commercially available products, or may be produced according to methods described in literature [see, for example, a pamphlet of International Publication 2007/067506, a pamphlet of International Publication 2004/104007, and *Journal of Medicinal Chemistry*, Vol. 48, pp. 2371-2387], or similar methods, or, as required, by appropriately combining the methods described below and in Examples and Production Examples.

Producing Method A

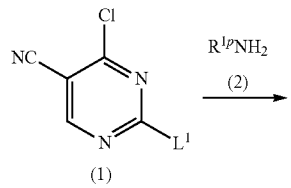

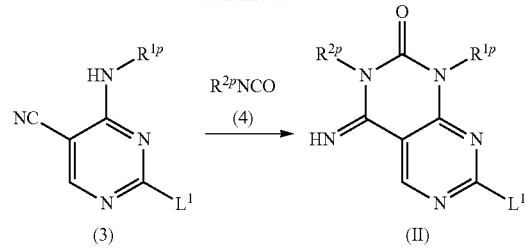

In the Formula, $R^{1p}$, $R^{2p}$ and $L^1$ are as defined above.

The producing method is a producing method of the compound represented by General Formula (II).

According to the producing method, the compound of General Formula (II) can be produced by the reaction of Compound (3), obtained by the reaction of Compound (1) and the amine represented by Formula (2), with the isocyanate represented by Formula (4).

The step in which Compound (1) reacts with the amine represented by Formula (2) to produce Compound (3) is generally performed using 0.5 moles to excess moles, preferably an equimolar amount to 3.0 moles of amine (2) with respect to 1 mole of Compound (I).

The reaction is generally performed in an inert solvent, for which, for example, methylene chloride, chloroform, tetrahydrofuran, ethylether, benzene, toluene, dimethylformamide, or a mixed solvent thereof is preferable.

Preferably, the reaction is performed in the presence of a base. Examples of the usable base include: organic bases such as triethylamine, diisopropylethylamine, pyridine, and 4-dimethylaminopyridine; and inorganic bases such as sodium hydroxide, potassium hydroxide, sodium carbonate, potassium carbonate, and sodium bicarbonate.

Generally, an equal to excess moles of the base is preferably used with respect to 1 mole of Compound (1). When the base is a liquid, the base can also serve as a solvent.

The reaction temperature is generally from −78° C. to 100° C., preferably 20° C. to 80° C.

The reaction time is generally from 5 minutes to 7 days, preferably 30 minutes to 24 hours.

The step in which Compound (3) reacts with the isocyanate of Formula (4) to produce the compound of General Formula (II) is generally performed using 0.5 moles to excess moles, preferably an equimolar amount to 3.0 moles of isocyanate (4) with respect to 1 mole of Compound (3).

The reaction is generally performed in an inert solvent, for which, for example, methylene chloride, chloroform, tetrahydrofuran, ethylether, benzene, toluene, dimethylformamide, or a mixed solvent thereof is preferably used. More preferable examples include dimethylformamide.

The reaction is generally performed in the presence of a base. Examples of the usable base include: organic bases such as triethylamine, diisopropylethylamine, pyridine, and 4-dimethylaminopyridine; and inorganic bases such as sodium hydride, potassium tert-butoxide, and sodium tert-butoxide.

Generally, an equal to excess moles of the base is preferably used with respect to 1 mole of Compound (3). When the base is a liquid, the base can also serve as a solvent.

The reaction temperature is generally from −78° C. to 100° C., preferably 20° C. to 80° C.

The reaction time is generally from 5 minutes to 7 days, preferably 30 minutes to 24 hours.

The compounds represented by General Formulae (1), (2), and (4) may be obtained from commercially available products, or may be produced using known methods, or, as required, by appropriately combining the methods described in Examples or similar methods.

(Alternative Method)

The compound represented by General Formula (I) or an N-oxide derivative thereof can be produced by first producing a compound of General Formula (V-1) by a reaction between the compound represented by Formula (3) and the compound of General Formula (III) or a salt thereof:

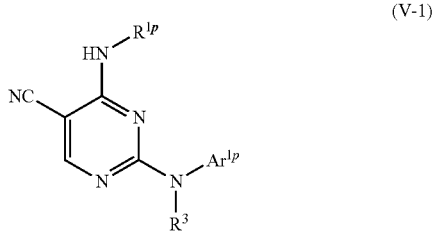

(V-1)

In the Formula, $Ar^{1p}$, $R^{1p}$ and $R^3$ are as defined above.

Compound (V-1) is then allowed to react with the isocyanate represented by Formula (4) to obtain a compound of General Formula (IV):

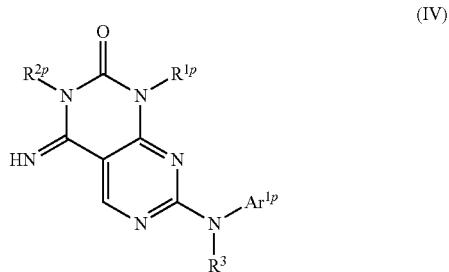

(IV)

In the Formula, $Ar^{1p}$, $R^{1p}$, $R^{2p}$ and $R^3$ are as defined above.

When the compound includes a protective group of the amino group, imino group, hydroxyl group or carbonyl group, this is followed by suitably selecting and performing the step of:

(1) removing the protective group; or
(2) oxidizing the nitrogen atom of the compound, when the target compound is an N-oxide derivative.

The step in which the compound of Formula (3) reacts with the compound of General Formula (III) or a salt thereof to produce the compound of General Formula (V-1) can be performed as in the foregoing step of Producing Method 1 in which the compound of Formula (II) reacts with the compound of Formula (III) or a salt thereof to produce a compound of Formula (IV).

The salt of the compound represented by Formula (III) usable in this step may be those exemplified as the salt of the compound of Formula (III) in Producing Method 1.

The step in which Compound (V-1) reacts with the isocyanate of Formula (4) to produce the compound of General Formula (IV) can be performed as in the step of Producing Method A in which Compound (3) reacts with the isocyanate of Formula (4) to produce the compound of General Formula (II).

The optional steps of removing the protective group and/or producing an N-oxide derivative can be performed according to the methods described in Producing Method 1.

The following describes exemplary pharmacological tests of a compound of the present invention. Pharmacological Test 1 (Wee1 kinase inhibitory effect)

(1) Purification of Wee1 kinase

A cDNA of Wee1 kinase with glutathione-S-transferase (GST) fused at the amino terminal thereof was inserted into a baculovirus expression vector to construct a recombinant baculovirus, with which cells of an insect cell line Sf9 were infected to overexpress the target protein. The infected cells were collected and lysed, and then the GST-tagged Wee1 kinase protein was adsorbed to a glutathione column and eluted from the column with glutathione, and the active fraction was desalted in a desalting column to give a purified enzyme.

(2) Measurement of Wee1 kinase activity

In measurement of the Wee1 kinase activity, a synthetic peptide, Poly(Lys, Tyr) hydrobromide (Lys:Tyr (4:1)) purchased from Sigma was used as the substrate.

The amount of the reaction mixture was 21.1 µL; and the composition of the reaction buffer was 50 mM Tris-HCl buffer (pH 7.4)/10 mM magnesium chloride/1 mM dithiothreitol. The purified Wee1 kinase, 2.5 µg of the substrate peptide, 10 µM of non-labeled adenosine triphosphate (ATP) and 1 µCi of [$\gamma$-$^{33}$P]-labeled ATP (2500 Ci/mmol or more) were added to the reaction buffer, and the resulting mixture was incubated at 30° C. for 30 minutes. Thereafter, 10 µL of 350 mM phosphate buffer was added to the reaction system to stop the reaction. The substrate peptide was adsorbed on a P81 paper filter 96-well plate and the plate was washed several times with 130 mM phosphate buffer, and the radioactivity thereof was counted using a liquid scintillation counter. The [$\gamma$-$^{33}$P]-labeled ATP was purchased from Amersham Bioscience, Ltd.

The addition of a test compound to the reaction system was carried out by preparing a series of dilutions of the compound with dimethyl sulfoxide (DMSO) and adding 1.1 µL of each dilution to the reaction system. As a control, 1.1 µL of DMSO was added to the reaction system.

As shown in Table 1, the compounds according to the invention exhibit an excellent Wee1 inhibitory effect.

TABLE 1

| Example | Wee1 Inhibition Activity ($IC_{50}$, nM) |
|---------|------------------------------------------|
| 1       | 4                                        |
| 2       | 2                                        |
| 3       | 12                                       |
| 4       | 10                                       |
| 5       | 17                                       |
| 6       | 8                                        |
| 7       | 6                                        |
| 8       | 17                                       |
| 9       | 16                                       |
| 10      | 18                                       |

Subsequently, an inhibitory effect of the compound of the general formula (I) according to the invention on Cdc2 tyrosine-15 phosphorylation in cells will be described below.

Pharmacological Test 2 (Method for determining drug effect using cells (inhibitory effect on Cdc2 (Cdk1) tyrosine-15 phosphorylation))

a) Reagents

Fetal bovine serum (FBS) was purchased from Morgate, Inc.; an RPMI-1640 medium and a DMEM medium were purchased from Invitrogen, Inc.; camptothecin was purchased from Sigma Co.; gemcitabine was purchased from Eli Lilly Japan K.K.; nocodazole and protease inhibitor cocktail were purchased from Sigma Co.; a rabbit anti-Cdc2 antibody and a mouse anti-Cdc2 antibody were purchased from Santa Cruz Biotechnology, Inc.; a rabbit anti-tyrosine-15-phosphorylated Cdc2 antibody and a horseradish peroxidase-labeled anti-mouse IgG antibody were purchased from Cell Signaling Technology, Inc.; and Sure Blue Reserve TMB peroxidase substrate was purchased from Kirkegaard & Perry Laboratories, Inc.

b) Cells

A human non-small cell lung cancer cell line (NCI-H1299) and a human colon cancer cell line (WiDr) can be obtained from American Type Culture Collection (ATCC).

c) Method for determining effect

In the method using NCI-H1299 cells, the cells were suspended in an RPMI-1640 medium supplemented with 10% FBS, and 100 µL of the resulting cell suspension was dispensed in a Nunclon Delta treated 96-well plastic plate purchased from Nunc, Inc. at a density of 2000 cells per well, and the plate was incubated overnight at 37° C. under an atmosphere of 5% $CO_2$ and 95% air. Camptothecin was dissolved in dimethyl sulfoxide (DMSO) and further the resulting solution was diluted with an RPMI-1640 medium supplemented with 10% FBS. Then, 50 µL of the diluted solution was added to each well of the plate in which the cells were seeded in advance such that the final concentration of camptothecin was 200 nM, and the plate was incubated at 37° C. under an atmosphere of 5% $CO_2$ and 95% air for 16 hours. A test compound was serially diluted with DMSO, and further diluted with an RPMI-1640 medium supplemented with 10% FBS containing 4000 nM nocodazole. Then, 50 µL of the test compound solution was added to each well of the plate in which the cells treated with camptothecin were seeded, and the plate was incubated at 37° C. under an atmosphere of 5% $CO_2$ and 95% air for 8 hours. Then, the culture medium was removed from each well and 1004 of a cell lysis buffer was added to each well, and the plate was shaken at 4° C. for 2 hours, and thereafter the liquid in the plate was frozen at −80° C. and then thawed, which was used as a lysed cell solution. Cdc2 and tyrosine-15-phosphorylated Cdc2 in this lysed cell solution were measured by an enzyme-linked immunosorbent assay (ELISA method), and a ratio of tyrosine-15-phosphorylated Cdc2 to Cdc2 was calculated to determine a 50% effective concentration ($EC_{50}$, nM) of the test compound for inhibition of phosphorylation in cells. The cell lysis buffer as used herein is an aqueous solution 50 mM containing 20 mM HEPES (pH 7.5), 150 mM sodium chloride, 1 mM disodium ethylenediamine tetraacetate, 0.1% polyoxyethylene (10) octylphenyl ether, 1% protease inhibitor cocktail, 1 mM dithiothreitol, 2 mM sodium orthovanadate, 10 mM sodium fluoride and 10 mM glycerol diphosphate. The measurement of Cdc2 by the ELISA method was carried out as follows. 50 µL of a solution of a rabbit anti-Cdc2 antibody obtained by diluting the antibody to 200 times with 50 mM carbonate-bicarbonate buffer (pH 9.6) was dispensed into each well of a 96-well Maxisorb immunoplate purchased from Nunc, Inc., and the immunoplate was let stand overnight at 4° C. to immobilize the antibody thereto. Subsequently, each well was washed three times with phosphate buffered saline (PBS), and 300 µL of PBS containing 5% bovine serum albumin (5% BSA/PBS) was added to each well, and then, the immunoplate was let stand at room temperature for 2 hours. Thereafter, each well was washed again three times with PBS, and 50 µL of a solution of a mouse anti-Cdc2 antibody obtained by diluting the antibody to 100 times with Tris-HCl buffered saline containing 0.05% polyoxyethylene sorbitan monolaurate and 1% BSA (1% BSA/TBS-T) was added to each well and also 5 µL of the lysed cell solution was added thereto, and then, the immunoplate was let stand overnight at 4° C. Subsequently, each well was washed three times with Tris-HCl buffered saline containing 0.05% polyoxyethylene sorbitan monolaurate and 0.1% BSA (0.1% BSA/TBS-T), and 70 µL of a solution of a horseradish peroxidase-labeled anti-mouse IgG antibody obtained by diluting the antibody to 2000 times with 1% BSA/TBS-T was added to each well, and then, the immunoplate was let stand at room temperature for 3 hours. Finally, each well was washed five times with 0.1% BSA/TBS-T, and 100 µL of Sure Blue Reserve TMB peroxidase substrate was added to each well, and a chromogenic reaction was allowed to proceed for 15 minutes in a dark place at room temperature. Thereafter, 100 µL of 1 M hydrochloric acid was added to each well to stop the reaction, and measurement was carried out by the colorimetric method. The measurement of tyrosine-15-phosphorylated Cdc2 by the ELISA method was carried out as follows. 50 µL of a solution of a rabbit anti-tyrosine-15-phosphorylated Cdc2 antibody obtained by diluting the antibody to 100 times with 50 mM carbonate-bicarbonate buffer (pH 9.6) was dispensed into each well of a 96-well Maxisorb immunoplate, and the immunoplate was let stand overnight at 4° C. to immobilize the antibody thereto. Subsequently, each well was washed three times with PBS, and 300 µL of 5% BSA/PBS was added to each well, and then, the immunoplate was let stand at room temperature for 2 hours. Thereafter, each well was washed again three times with PBS, and 50 µL of a solution of a mouse anti-Cdc2 antibody obtained by diluting the antibody to 100 times with 1% BSA/TBS-T was added to each well and also 5 µL of the lysed cell solution was added thereto, and then, the immunoplate was let stand overnight at 4° C. Subsequently, each well was washed three times with 0.1% BSA/TBS-T, and 70 µL of a solution of a horseradish peroxidase-labeled anti-mouse IgG antibody obtained by diluting the antibody to 2000 times with 1% BSA/TBS-T was added to each well, and then, the immunoplate was let stand at room temperature for 3 hours. Finally, each well was washed five times with 0.1% BSA/TBS-T, and 100 µL of Sure Blue Reserve TMB peroxidase substrate was added to each well, and a chromogenic reaction was allowed to proceed for 5 minutes in a dark place at room temperature. Thereafter, 100 µL of 1 M hydrochloric acid was added to each well to stop the reaction, and measurement was carried out by the colorimetric method. The results are shown in Table 2.

In the method using WiDr cells, the cells are suspended in a DMEM medium supplemented with 10% FBS, and 100 µL of the resulting cell suspension is dispensed in a Nunclon Delta treated 96-well plastic plate at a density of 2000 cells per well, and the plate is incubated overnight at 37° C. under an atmosphere of 5% $CO_2$ and 95% air. Gemcitabine is dissolved in PBS and further the resulting solution is diluted with a DMEM medium supplemented with 10% FBS. Then, 50 µL of the diluted solution is added to each well of the plate in which the cells have been seeded in advance such that the final concentration of gemcitabine is 100 nM, and the plate is incubated at 37° C. under an atmosphere of 5% $CO_2$ and 95% air for 24 hours. A test compound is serially diluted with DMSO, and further diluted with a DMEM medium supplemented with 10% FBS containing 1200 nM nocodazole. Then, 50 µL of the test compound solution is added to each well of the plate in which the cells treated with gemcitabine have been seeded, and the plate is incubated at 37° C. under an atmosphere of 5% $CO_2$ and 95% air for 8 hours. Then, the culture medium is removed from each well and 100 µL of a cell lysis buffer is added to each well, and the plate is shaken at 4° C. for 2 hours, and thereafter the liquid in the plate is frozen at −80° C. and then thawed, which is used as a lysed cell solution. Cdc2 and tyrosine-15-phosphorylated Cdc2 in this lysed cell solution are measured by the ELISA method, and a ratio of tyrosine-15-phosphorylated Cdc2 to Cdc2 is calculated to determine a 50% effective concentration ($EC_{50}$, nM) of the test compound for inhibition of phosphorylation in cells. The measurement of Cdc2 by the ELISA method is carried out as follows. 50 μL of a solution of a rabbit anti-Cdc2 antibody obtained by diluting the antibody to 200 times with 50 mM carbonate-bicarbonate buffer (pH 9.6) is dispensed into each well of a 96-well Maxisorb plastic plate, and the plate is let stand overnight at 4° C. to immobilize the antibody thereto. Thereafter, each well is washed three times with PBS, and 300 μL of 5% BSA/PBS is added to each well, and then, the plate is let stand at room temperature for 2 hours. Thereafter, each well is washed again three times with PBS, and 50 μL of a solution of a mouse anti-Cdc2 antibody obtained by diluting the antibody to 100 times with 1% BSA/TBS-T is added to each well and also 10 μL of the lysed cell solution is added thereto, and then, the plate is let stand overnight at 4° C. Subsequently, each well is washed three times with 0.1% BSA/TBS-T, and 70 μL of a solution of a horseradish peroxidase-labeled anti-mouse IgG antibody obtained by diluting the antibody to 2000 times with 1% BSA/TBS-T is added to each well, and then, the plate is let stand at room temperature for 3 hours. Finally, each well is washed five times with 0.1% BSA/TBS-T, and 100 μL of Sure Blue Reserve TMB peroxidase substrate is added to each well, and a chromogenic reaction is allowed to proceed for 15 minutes in a dark place at room temperature. Thereafter, 100 μL of 1 M hydrochloric acid is added to each well to stop the reaction, and measurement is carried out by the colorimetric method. The measurement of tyrosine-15-phosphorylated Cdc2 by the ELISA method is carried out as follows. 50 μL of a solution of a rabbit anti-tyrosine-15-phosphorylated Cdc2 antibody obtained by diluting the antibody to 100 times with 50 mM carbonate-bicarbonate buffer (pH 9.6) is dispensed into each well of a 96-well Maxisorb plastic plate, and the plate is let stand overnight at 4° C. to immobilize the antibody thereto. Thereafter, each well is washed three times with PBS, and 300 μL of 5% BSA/PBS is added to each well, and then, the plate is let stand at room temperature for 2 hours. Thereafter, each well is washed again three times with PBS, and 50 μL of a solution of a mouse anti-Cdc2 antibody obtained by diluting the antibody to 100 times with 1% BSA/TBS-T is added to each well and also 10 μL of the lysed cell solution is added thereto, and then, the plate is let stand overnight at 4° C. Subsequently, each well is washed three times with 0.1% BSA/TBS-T, and 70 μL of a solution of a horseradish peroxidase-labeled anti-mouse IgG antibody obtained by diluting the antibody to 2000 times with 1% BSA/TBS-T is added to each well, and then, the plate is let stand at room temperature for 3 hours. Finally, each well is washed five times with 0.1% BSA/TBS-T, and 100 μL of Sure Blue Reserve TMB peroxidase substrate is added to each well, and a chromogenic reaction is allowed to proceed for 10 minutes in a dark place at room temperature. Thereafter, 100 μL of 1 M hydrochloric acid is added to each well to stop the reaction, and measurement is carried out by the colorimetric method.

As shown in Table 2, the compounds according to the invention exhibit an excellent inhibitory effect on Cdc2 tyrosine-15 phosphorylation against human-derived cancer cell lines.

TABLE 2

| Example | Cdc2-Tyrosine 15 Phosphorylation Inhibiting Effect (nM) |
|---|---|
| 1 | 71 |
| 2 | 86 |
| 3 | 45 |
| 4 | 34 |
| 5 | 66 |
| 6 | 25 |
| 8 | 75 |
| 9 | 110 |
| 10 | 110 |

Subsequently, a checkpoint abrogating effect of the compound of the general formula (I) according to the invention on cells will be described below.

Pharmacological Test 3 (Method for Determining Drug Effect Using Cells (Checkpoint Abrogating Effect))

a) Reagents

Fetal bovine serum (FBS) can be obtained from Morgate, Inc.; a DMEM medium can be obtained from Invitrogen, Inc.; gemcitabine can be obtained from Eli Lilly Japan K.K.; nocodazole and 4',6-diamidino-2-phenylindole can be obtained from Sigma Co.; a rabbit anti-phosphorylated histone H3 antibody can be obtained from Upstate, Inc.; and an anti-rabbit IgG antibody fluorescently labeled with Alexa Fluor 488 can be obtained from Molecular Probe, Inc.

b) Cells

A human colon cancer cell line (WiDr) can be obtained from American Type Culture Collection (ATCC).

c) Method for Determining Effect

The cells are suspended in a DMEM medium supplemented with 10% FBS, and 100 μL of the resulting cell suspension is dispensed in a poly-D-lysine coated 96-well plastic plate purchased from Becton, Dickinson and Company at a density of 2000 cells per well, and the plate is incubated overnight at 37° C. under an atmosphere of 5% $CO_2$ and 95% air. Gemcitabine is dissolved in phosphate buffered saline (PBS) and further the resulting solution is diluted with a DMEM medium supplemented with 10% FBS. Then, 50 μL of the diluted solution is added to each well of the plate in which the cells have been seeded in advance such that the final concentration of gemcitabine is 100 nM, and the plate is incubated at 37° C. under an atmosphere of 5% $CO_2$ and 95% air for 24 hours. A test compound is serially diluted with dimethyl sulfoxide, and further diluted with a DMEM medium supplemented with 10% FBS containing 1200 nM nocodazole. Then, 50 μL of the test compound solution is added to each well of the plate in which the cells treated with gemcitabine have been seeded, and the plate is incubated at 37° C. under an atmosphere of 5% $CO_2$ and 95% air for 8 hours. Then, the culture medium is removed from each well and 100 μL of methanol previously chilled to −20° C. is added to each well, and the plate is let stand overnight at −20° C. to fix the cells. Thereafter, the cells fixed with methanol are washed PBS, and 50 μL of PBS containing 1% bovine serum albumin (1% BSA/PBS) is added to each well, and then, the plate is let stand at room temperature for 30 minutes. Thereafter, 50 μL of a solution of a rabbit anti-phosphorylated histone H3 antibody obtained by diluting the antibody to 250 times with 1% BSA/PBS is added to each well, and then, the plate is let stand at room temperature for 90 minutes. Then, after the cells are washed with PBS, 50 μL of a solution containing 4',6-diamidino-2-phenylindole diluted to 10 μg/mL with 1% BSA/PBS and an anti-rabbit IgG antibody fluorescently labeled with Alexa Fluor 488 diluted to 250 times with 1% BSA/PBS is added to each well and a reaction is allowed to proceed for 60 minutes in a dark place at room temperature. Finally, after the cells are washed with PBS, the fluorescence intensity is measured. Then, a ratio of phosphorylated histone H3 positive cells (cells which proceed to cell division phase by abrogating checkpoint) is calculated to determine a 50% effective concentration ($EC_{50}$, nM) of the test compound for checkpoint abrogation in cells.

As described above, an excellent checkpoint abrogating effect of the compound according to the invention on human-derived cancer cells (WiDr) can be determined.

Pharmacological Test 4 (Inhibitory Effect on Tumor Growth)

A human colon cancer cell line WiDr (obtained from ATCC) is implanted into the subcutaneous area of the back of F344/N Jcl-rnu nude rats. 12 days after the implantation, gemcitabine (Gemzar injection, Eli Lilly and Company) is intravenously administered to the rats at a dose of 5 mg/kg. At 24 hours thereafter, a test compound is suspended in a solvent (0.5% methyl cellulose) and orally administered to the rats. This procedure is repeated once a week for 3 weeks. A tumor volume (0.5×(major diameter)×(minor diameter)$^2$) is measured on days 0, 3, 6, 10, 13, 17, 20, 24 and 27. Day 0 means the day on which gemcitabine is first administered. A relative tumor volume is calculated based on the tumor volume on day 0 the value of which is taken as 1. Further, a tumor growth ratio (% T/C) is calculated from the following equation.

In the case where a change in tumor volume from day 0 in the test compound administration group is more than 0 (>0):

% T/C=[(a change in tumor volume in each test compound group on day 3, 6, 10, 13, 17, 20, 24 or 27)/(a change in tumor volume in the control group on day 3, 6, 10, 13, 17, 20, 24 or 27)]×100.

In the case where a change in tumor volume from day 0 in the test compound administration group is less than 0 (<0):

% T/C=[(a change in tumor volume in each test compound group on day 3, 6, 10, 13, 17, 20, 24 or 27)/(tumor volume in each test compound group on day 0)]×100.

As described above, it can be determined that the compound of the invention potentiates the effect of any other anticancer agents by using the compound of the invention in combination with the anticancer agent.

Pharmacological Test 5 (Method for Determining Drug Effect Using Cells (Radiation (X-Ray) Sensitizing Effect))

a) Reagents

Fetal bovine serum (FBS) can be obtained from Morgate, Inc.; an RPMI 1640 medium and 0.25% trypsin EDTA can be obtained from Invitrogen, Inc.; a cycle test plus DNA reagent kit can be obtained from Becton, Dickinson and Company; and a nylon net filter can be obtained from Millipore, Inc.

b) Cells

A human non-small cell lung cancer cell line (NCI-H1299) can be obtained from ATCC.

c) Method for Determining Effect

NCI-H1299 cells are suspended in an RPMI-1640 medium supplemented with 10% FBS, and 2 mL of the resulting cell suspension is dispensed in a Nunclon Delta treated E-well plastic plate purchased from Nunc, Inc. at a density of 100000 cells per well, and the plate is incubated overnight at 37° C. under an atmosphere of 5% $CO_2$ and 95% air. The cells are irradiated with 5000 R X-ray using M-150 WE available from Softex, and then, the plate is further incubated for 16 hours at 37° C. under an atmosphere of 5% $CO_2$ and 95% air. A test compound is serially diluted with DMSO and 2 μL of the test compound solution is added to each well of the plate in which the cells treated with X-rays have been seeded in advance. Then, after the plate is incubated for 8 hours at 37° C. under an atmosphere of 5% $CO_2$ and 95% air, the culture medium is taken out and kept as a part of each sample, and the cells remaining in the plate is suspended by adding 600 μL of 0.25% trypsin to each well and letting the suspension stand at room temperature to prepare a single cell suspension. The thus obtained single cell suspension and the previously taken culture medium are mixed for each sample, and then, the resulting mixture is centrifuged and the supernatant is removed. Sampling is thus completed. The thus obtained sample is suspended in 1 mL of a buffer in a cycle test plus DNA reagent kit and the resulting suspension is cryopreserved at −80° C. The cryopreserved sample is thawed on the test date and centrifuged and the supernatant is removed. Then, the residue is suspended in 250 μL of a solution in the cycle test plus and the resulting suspension is let stand at room temperature for 10 minutes, and then 150 μL of B solution is added thereto, and the resulting mixture is further let stand at room temperature for 10 minutes. Subsequently, 150 μL of C solution is added thereto, and the resulting mixture is let stand at 4° C. for 10 minutes, and then filtered through a nylon net filter thereby completing staining of DNA. The DNA amount in each cell is quantitatively determined by the FACS method using FACS Calibur available from Becton, Dickinson and Company, and a ratio of cells having caused DNA fragmentation is determined As described above, an excellent DNA fragmentation inducing effect of the compound of the invention on a human-derived cancer cell line (NCI-H1299) can be determined and the X-ray sensitizing effect of the compound of the invention can be determined.

The compound represented by the general formula (I) can be administered orally or parenterally, and by formulating the compound into a preparation suitable for such an administration route, the compound can be used as a pharmaceutical composition or an anticancer agent.

The term "cancer" as used herein includes various sarcomas and carcinomas and includes solid cancers and hematopoietic cancers. Here, the solid cancers include, for example, brain tumor, head and neck cancer, esophageal cancer, thyroid cancer, small cell cancer, non-small cell cancer, breast cancer, lung cancer, stomach cancer, gallbladder and bile duct cancer, liver cancer, pancreatic cancer, colon cancer, rectal cancer, ovarian cancer, chorioepithelioma, endometrial cancer, cervical cancer, renal pelvic and ureteral cancer, bladder cancer, prostate cancer, penile cancer, testicular cancer, embryonal carcinoma, Wilms' tumor, skin cancer, malignant melanoma, neuroblastoma, osteosarcoma, Ewing's tumor, soft tissue sarcoma and the like. On the other hand, the hematopoietic cancers include, for example, acute leukemia, chronic lymphocytic leukemia, chronic myeloid leukemia, polycythemia vera, malignant lymphoma, multiple myeloma, Hodgkin's lymphoma, non-Hodgkin's lymphoma and the like.

The term "treatment of cancer" as used herein means that an anticancer agent is administered to a cancer patient so as to inhibit the growth of the cancer cells. Preferably, the treatment enables the regression of cancer growth, i.e., the reduction of the size of detectable cancer. More preferably, the treatment eradicates cancer completely.

Preferred examples of the cancer on which the therapeutic effect of the compound according to the invention is expected include human solid cancers. Examples of the human solid cancers include brain tumor, head and neck cancer, esophageal cancer, thyroid cancer, small cell cancer, non-small cell cancer, breast cancer, lung cancer, stomach cancer, gallbladder and bile duct cancer, liver cancer, pancreatic cancer, colon cancer, rectal cancer, ovarian cancer, chorioepithelioma, endometrial cancer, cervical cancer, renal pelvic and ureteral cancer, bladder cancer, prostate cancer, penile cancer, testicular cancer, embryonal carcinoma, Wilms' tumor, skin cancer, malignant melanoma, neuroblastoma, osteosarcoma, Ewing's tumor, soft tissue sarcoma, acute leukemia, chronic lymphocytic leukemia, chronic myeloid leukemia and Hodgkin's lymphoma.

The pharmaceutical composition or anticancer agent according to the invention may contain a pharmaceutically acceptable carrier or diluent. Here, the "pharmaceutically acceptable carrier or diluent" means an excipient (for example, a fat, beeswax, a semi-solid or liquid polyol, a natural or hydrogenated oil, etc.); water (for example, distilled water, particularly distilled water for injection, etc.), physiological saline, an alcohol (for example, ethanol), glycerol, a polyol, an aqueous glucose solution, mannitol, a vegetable oil, etc.; an additive (for example, an expander, a disintegrant, a binder, a lubricant, a wetting agent, a stabilizer, an emulsifier, a dispersant, a preservative, a sweetener, a colorant, a seasoning agent or a flavor, a thickening agent, a diluent, a buffer substance, a solvent or a solubilizing agent, a chemical for providing a storage effect, a salt for changing osmotic pressure, a coating agent or an antioxidant) or the like.

The preparation related to the pharmaceutical composition or anticancer agent of the invention can have any of various dosage forms, and examples thereof include oral preparations such as tablets, capsules, powders, granules and liquids, sterilized liquid parenteral preparations such as solutions and suspensions, suppositories and ointments.

A solid preparation can be prepared in the form of a tablet, a capsule, a granule or a powder as such, or can be prepared using an appropriate carrier (additive). Examples of such carrier (additive) include saccharides such as lactose and glucose; starches of corn, wheat and rice; fatty acids such as stearic acid; inorganic salts such as magnesium metasilicate aluminate and anhydrous calcium phosphate; synthetic polymers such as polyvinylpyrrolidone and polyalkylene glycol; fatty acid salts such as calcium stearate and magnesium stearate; alcohols such as stearyl alcohol and benzyl alcohol; synthetic cellulose derivatives such as methyl cellulose, carboxymethyl cellulose, ethyl cellulose and hydroxypropyl methyl cellulose; and other conventionally used additives such as gelatin, talc, vegetable oils and gum arabic.

These solid preparations such as tablets, capsules, granules and powders may generally contain, as an active ingredient, for example, 0.1 to 100% by weight, preferably 5 to 98% by weight of the compound represented by the above-mentioned formula (I) based on the total weight of the preparation.

A liquid preparation is produced in the form of a suspension, a syrup, an injection or a drip infusion (intravenous infusion) using an appropriate additive which is conventionally used in a liquid preparation such as water, an alcohol or a plant-derived oil such as soybean oil, peanut oil or sesame oil.

In particular, as an appropriate solvent or diluent when the preparation is administered parenterally in the form of an intramuscular injection, an intravenous injection or a subcutaneous injection, distilled water for injection, an aqueous solution of lidocaine hydrochloride (for intramuscular injection), physiological saline, an aqueous glucose solution, ethanol, polyethylene glycol, propylene glycol, a liquid for intravenous injection (for example, an aqueous solution of citric acid, sodium citrate or the like) or an electrolytic solution (for intravenous drip infusion or intravenous injection), or a mixed solution thereof can be exemplified.

Such an injection may be also in the form of a preliminarily dissolved solution, or in the form of a powder per se or a powder with the addition of a suitable carrier (additive) which is dissolved at the time of use. The injection liquid can contain, for example, 0.1 to 10% by weight of an active ingredient based on the total weight of the preparation.

The liquid preparation such as a suspension or a syrup for oral administration can contain, for example, 0.1 to 10% by weight of an active ingredient based on the total weight of the preparation.

Such a preparation can be easily produced by a person skilled in the art according to a common procedure or a conventional technique. For example, in the case of an oral preparation, it can be produced by, for example, mixing an appropriate amount of the compound of the invention with an appropriate amount of lactose and filling this mixture into a hard gelatin capsule suitable for oral administration. On the other hand, in the case where the preparation containing the compound of the invention is an injection, it can be produced by, for example, mixing an appropriate amount of the compound of the invention with an appropriate amount of 0.9% physiological saline and filling this mixture in a vial for injection.

The compound of the invention can be used by combining it with any other agent useful for treatment of various cancers or with radiotherapy. The individual ingredients in the case of such a combination can be administered at different times or at the same time as divided preparations or a single preparation during the period of treatment. Accordingly, the invention should be so interpreted that it includes all modes of administration at the same time or at different times, and the administration in the invention should be interpreted so. The scope of the combination of the compound of the invention with any other agent useful for the treatment of the above-mentioned diseases should include, in principle, every combination thereof with every pharmaceutical preparation useful for the treatment of the above-mentioned diseases.

The radiation therapy itself means an ordinary method in the field of treatment of cancer. In the radiation therapy, any of various radiations such as an X-ray, a γ-ray, a neutron ray, an electron beam and a proton beam, and radiation sources is used. The most common radiation therapy is one which is carried out by external radiation using a linear accelerator, and in which a γ-ray is irradiated.

The compound of the invention can potentiate the therapeutic effect of the radiation therapy by combining the compound of the invention with the radiation therapy and therefore can be useful as a radiation sensitizer in the field of treatment of cancer.

Another aspect of the compound of the invention is that the compound of the invention is also useful as a sensitizer for any other anticancer agents in the field of treatment of cancer.

The compound of the invention can be used by combining it with radiation therapy and/or any other anticancer agents described below.

The "sensitizer" of radiation or for an anticancer agent as used herein means a medicinal agent which, when it is used by combining it with radiation therapy and/or chemotherapy using an anticancer agent, additively or synergistically potentiates the therapeutic effect of the radiation therapy and/or chemotherapy in the field of treatment of cancer.

The respective preparations in the combined preparation according to the invention can have any form, and they can be produced in the same manner as that for the above-mentioned preparation. A drug combination containing the compound of the invention and any other anticancer agents can also be easily produced by a person skilled in the art according to a common procedure or a conventional technique.

The above-mentioned combination includes a combination of the composition of the invention not only with one other active substance but also with two or more other active substances. There are a lot of examples of the combination of the composition of the invention with one or two or more active substances selected from the therapeutic agents for the above-mentioned diseases.

The agents to be combined with the compositions include, for example, an anticancer agent selected from the group consisting of anticancer alkylating agents, anticancer antimetabolites, anticancer antibiotics, plant-derived anticancer agents, anticancer platinum coordination compounds, anticancer camptothecin derivatives, anticancer tyrosine kinase inhibitors, monoclonal antibodies, interferons, biological response modifiers and other anticancer agents as well as pharmaceutically acceptable salt(s) or ester(s) thereof.

The term "anticancer alkylating agent" as used in the present specification refers to an alkylating agent having anticancer activity, and the term "alkylating agent" herein generally refers to an agent giving an alkyl group in the alkylation reaction in which a hydrogen atom of an organic compound is substituted with an alkyl group. The term "anticancer alkylating agent" may be exemplified by nitrogen mustard N-oxide, cyclophosphamide, ifosfamide, melphalan, busulfan, mitobronitol, carboquone, thiotepa, ranimustine, nimustine, temozolomide or carmustine.

The term "anticancer antimetabolite" as used in the specification refers to an antimetabolite having anticancer activity, and the term "antimetabolite" herein includes, in a broad sense, substances which disturb normal metabolism and substances which inhibit the electron transfer system to prevent the production of energy-rich intermediates, due to their structural or functional similarities to metabolites that are important for living organisms (such as vitamins, coenzymes, amino acids and saccharides). The term "anticancer antimetabolites" may be exemplified methotrexate, 6-mercaptopurine riboside, mercaptopurine, 5-fluorouracil, tegafur, doxifluridine, carmofur, cytarabine, cytarabine ocfosfate, enocitabine, S-1, gemcitabine, fludarabine or pemetrexed disodium, and preferred are cytarabine, gemcitabine and the like.

The term "anticancer antibiotic" as used in the specification refers to an antibiotic having anticancer activity, and the "antibiotic" herein includes substances that are produced by microorganisms and inhibit cell growth and other functions of microorganisms and of other living organisms. The term "anticancer antibiotic" may be exemplified by actinomycin D, doxorubicin, daunorubicin, neocarzinostatin, bleomycin, peplomycin, mitomycin C, aclarubicin, pirarubicin, epirubicin, zinostatin stimalamer, idarubicin, sirolimus or valrubicin, and preferred are doxorubicin, mitomycin C and the like.

The term "plant-derived anticancer agent" as used in the specification includes compounds having anticancer activities which originate from plants, or compounds prepared by applying chemical modification to the foregoing compounds. The term "plant-derived anticancer agent" may be exemplified by vincristine, vinblastine, vindesine, etoposide, sobuzoxane, docetaxel, paclitaxel and vinorelbine, and preferred are etoposide and the like.

The term "anticancer camptothecin derivative" as used in the specification refers to compounds that are structurally related to camptothecin and inhibit cancer cell growth, including camptothecin per se. The term "anticancer camptothecin derivative" is not particularly limited to, but may be exemplified by, camptothecin, 10-hydroxycamptothecin, topotecan, irinotecan or 9-aminocamptothecin, with camptothecin being preferred. Further, irinotecan is metabolized in vivo and exhibits anticancer effect as SN-38. The action mechanism and the activity of the camptothecin derivatives are believed to be virtually the same as those of camptothecin (e.g., Nitta, et al., Gan to Kagaku Ryoho, 14, 850-857 (1987)).

The term "anticancer platinum coordination compound" as used in the specification refers to a platinum coordination compound having anticancer activity, and the term "platinum coordination compound" herein refers to a platinum coordination compound which provides platinum in ion form. Preferred platinum compounds include cisplatin; cis-diamminediaquoplatinum (II)-ion; chloro(diethylenetriamine)-platinum (II) chloride; dichloro(ethylenediamine)-platinum (II); diammine(1,1-cyclobutanedicarboxylato) platinum (II) (carboplatin); spiroplatin; iproplatin; diammine(2-ethylmalonato)platinum (II); ethylenediaminemalonatoplatinum (II); aqua(1,2-diaminodicyclohexane)sulfatoplatinum (II); aqua (1,2-diaminodicyclohexane)malonatoplatinum (II); (1,2-diaminocyclohexane)malonatoplatinum (II); (4-carboxyphthalato)(1,2-diaminocyclohexane) platinum (II); (1,2-diaminocyclohexane)-(isocitrato)platinum (II); (1,2-diaminocyclohexane)oxalatoplatinum (II); ormaplatin; tetraplatin; carboplatin, nedaplatin and oxaliplatin, and preferred is carboplatin or cisplatin. Further, other anticancer platinum coordination compounds mentioned in the specification are known and are commercially available and/or producible by a person having ordinary skill in the art by conventional techniques.

The term "anticancer tyrosine kinase inhibitor" as used in the specification refers to a tyrosine kinase inhibitor having anticancer activity, and the term "tyrosine kinase inhibitor" herein refers to a chemical substance inhibiting "tyrosine kinase" which transfers a γ-phosphate group of ATP to a hydroxyl group of a specific tyrosine in protein. The term "anticancer tyrosine kinase inhibitor" may be exemplified by gefitinib, imatinib or erlotinib.

The term "monoclonal antibody" as used in the specification, which is also known as single clonal antibody, refers to an antibody produced by a monoclonal antibody-producing cell, and examples thereof include cetuximab, bevacizumab, rituximab, alemtuzumab and trastuzumab.

The term "interferon" as used in the specification refers to an interferon having anticancer activity, and it is a glycoprotein having a molecular weight of about 20,000 which is produced and secreted by most animal cells upon viral infection. It has not only the effect of inhibiting viral growth but also various immune effector mechanisms including inhibition of growth of cells (in particular, tumor cells) and enhancement of the natural killer cell activity, thus being designated as one type of cytokine. Examples of "interferon" include interferon α, interferon α-2a, interferon α-2b, interferon β, interferon γ-1a and interferon γ-n1.

The term "biological response modifier" as used in the specification is the so-called biological response modifier or BRM and is generally the generic term for substances or drugs for modifying the defense mechanisms of living organisms or biological responses such as survival, growth or differentiation of tissue cells in order to direct them to be useful for an individual against tumor, infection or other diseases. Examples of the "biological response modifier" include krestin, lentinan, sizofuran, picibanil and ubenimex.

The term "other anticancer agent" as used in the specification refers to an anticancer agent which does not belong to any of the above-described agents having anticancer activities. Examples of the "other anticancer agent" include mitoxantrone, L-asparaginase, procarbazine, dacarbazine, hydroxycarbamide, pentostatin, tretinoin, alefacept, darbepoetin alfa, anastrozole, exemestane, bicalutamide, leuprorelin, flutamide, fulvestrant, pegaptanib octasodium, denileukin diftitox, aldesleukin, thyrotropin alfa, arsenic trioxide, bortezomib, capecitabine, and goserelin.

The above-described terms "anticancer alkylating agent", "anticancer antimetabolite", "anticancer antibiotic", "plant-derived anticancer agent", "anticancer platinum coordination compound", "anticancer camptothecin derivative", "anticancer tyrosine kinase inhibitor", "monoclonal antibody", "interferon", "biological response modifier" and "other anticancer agent" are all known and are either commercially available or producible by a person skilled in the art by methods known per se or by well-known or conventional methods. The process for preparation of gefitinib is described, for example, in U.S. Pat. No. 5,770,599; the process for preparation of cetuximab is described, for example, in WO 96/40210; the process for preparation of bevacizumab is described, for example, in WO 94/10202; the process for preparation of oxaliplatin is described, for example, in U.S. Pat. Nos. 5,420,319 and 5,959,133; the process for preparation of gemcitabine is described, for example, in U.S. Pat. Nos. 5,434,254 and 5,223,608; and the process for preparation of camptothecin is described in U.S. Pat. Nos. 5,162,532, 5,247,089, 5,191,082, 5,200,524, 5,243,050 and 5,321,140; the process for preparation of irinotecan is described, for example, in U.S. Pat. No. 4,604,463; the process for preparation of topotecan is described, for example, in U.S. Pat. No. 5,734,056; the process for preparation of temozolomide is described, for example, in JP-B No. 4-5029; and the process for preparation of rituximab is described, for example, in JP-W No. 2-503143.

The above-mentioned anticancer alkylating agents are commercially available, as exemplified by the following: nitrogen mustard N-oxide from Mitsubishi Pharma Corp. as Nitromin (tradename); cyclophosphamide from Shionogi & Co., Ltd. as Endoxan (tradename); ifosfamide from Shionogi & Co., Ltd. as Ifomide (tradename); melphalan from GlaxoSmithKline Corp. as Alkeran (tradename); busulfan from Takeda Pharmaceutical Co., Ltd. as Mablin (tradename); mitobronitol from Kyorin Pharmaceutical Co., Ltd. as Myebrol (tradename); carboquone from Sankyo Co., Ltd. as Esquinon (tradename); thiotepa from Sumitomo Pharmaceutical Co., Ltd. as Tespamin (tradename); ranimustine from Mitsubishi Pharma Corp. as Cymerin (tradename); nimustine from Sankyo Co., Ltd. as Nidran (tradename); temozolomide from Schering Corp. as Temodar (tradename); and carmustine from Guilford Pharmaceuticals Inc. as Gliadel Wafer (tradename).

The above-mentioned anticancer antimetabolites are commercially available, as exemplified by the following: methotrexate from Takeda Pharmaceutical Co., Ltd. as Methotrexate (tradename); 6-mercaptopurine riboside from Aventis Corp. as Thioinosine (tradename); mercaptopurine from Takeda Pharmaceutical Co., Ltd. as Leukerin (tradename); 5-fluorouracil from Kyowa Hakko Kogyo Co., Ltd. as 5-FU (tradename); tegafur from Taiho Pharmaceutical Co., Ltd. as Futraful (tradename); doxyfluridine from Nippon Roche Co., Ltd. as Furutulon (tradename); carmofur from Yamanouchi Pharmaceutical Co., Ltd. as Yamafur (tradename); cytarabine from Nippon Shinyaku Co., Ltd. as Cylocide (tradename); cytarabine ocfosfate from Nippon Kayaku Co., Ltd. as Strasid (tradename); enocitabine from Asahi Kasei Corp. as Sanrabin (tradename); S-1 from Taiho Pharmaceutical Co., Ltd. as TS-1 (tradename); gemcitabine from Eli Lilly & Co. as Gemzar (tradename); fludarabine from Nippon Schering Co., Ltd. as Fludara (tradename); and pemetrexed disodium from Eli Lilly & Co. as Alimta (tradename).

The above-mentioned anticancer antibiotics are commercially available, as exemplified by the following: actinomycin D from Banyu Pharmaceutical Co., Ltd. as Cosmegen (tradename); doxorubicin from Kyowa Hakko Kogyo Co., Ltd. as Adriacin (tradename); daunorubicin from Meiji Seika Kaisha Ltd. as Daunomycin; neocarzinostatin from Yamanouchi Pharmaceutical Co., Ltd. as Neocarzinostatin (tradename); bleomycin from Nippon Kayaku Co., Ltd. as Bleo (tradename); pepromycin from Nippon Kayaku Co, Ltd. as Pepro (tradename); mitomycin C from Kyowa Hakko Kogyo Co., Ltd. as Mitomycin (tradename); aclarubicin from Yamanouchi Pharmaceutical Co., Ltd. as Aclacinon (tradename); pirarubicin from Nippon Kayaku Co., Ltd. as Pinorubicin (tradename); epirubicin from Pharmacia Corp. as Pharmorubicin (tradename); zinostatin stimalamer from Yamanouchi Pharmaceutical Co., Ltd. as Smancs (tradename); idarubicin from Pharmacia Corp. as Idamycin (tradename); sirolimus from Wyeth Corp. as Rapamune (tradename); and valrubicin from Anthra Pharmaceuticals Inc. as Valstar (tradename).

The above-mentioned plant-derived anticancer agents are commercially available, as exemplified by the following: vincristine from Shionogi & Co., Ltd. as Oncovin (tradename); vinblastine from Kyorin Pharmaceutical Co., Ltd. as Vinblastine (tradename); vindesine from Shionogi & Co., Ltd. as Fildesin (tradename); etoposide from Nippon Kayaku Co., Ltd. as Lastet (tradename); sobuzoxane from Zenyaku Kogyo Co., Ltd. as Perazolin (tradename); docetaxel from Aventis Corp. as Taxsotere (tradename); paclitaxel from Bristol-Myers Squibb Co. as Taxol (tradename); and vinorelbine from Kyowa Hakko Kogyo Co., Ltd. as Navelbine (tradename).

The above-mentioned anticancer platinum coordination compounds are commercially available, as exemplified by the following: cisplatin from Nippon Kayaku Co., Ltd. as Randa (tradename); carboplatin from Bristol-Myers Squibb Co. as Paraplatin (tradename); nedaplatin from Shionogi & Co., Ltd. as Aqupla (tradename); and oxaliplatin from Sanofi-Synthelabo Co. as Eloxatin (tradename).

The above-mentioned anticancer camptothecin derivatives are commercially available, as exemplified by the following: irinotecan from Yakult Honsha Co., Ltd. as Campto (tradename); topotecan from GlaxoSmithKline Corp. as Hycamtin (tradename); and camptothecin from Aldrich Chemical Co., Inc., U.S.A.

The above-mentioned anticancer tyrosine kinase inhibitors are commercially available, as exemplified by the following: gefitinib from AstraZeneca Corp. as Iressa (tradename); imatinib from Novartis AG as Gleevec (tradename); and erlotinib from OSI Pharmaceuticals Inc. as Tarceva (tradename).

The above-mentioned monoclonal antibodies are commercially available, as exemplified by the following: cetuximab from Bristol-Myers Squibb Co. as Erbitux (tradename); bevacizumab from Genentech, Inc. as Avastin (tradename); rituximab from Biogen Idec Inc. as Rituxan (tradename); alemtuzumab from Berlex Inc. as Campath (tradename); and trastuzumab from Chugai Pharmaceutical Co., Ltd. as Herceptin (tradename).

The above-mentioned interferons are commercially available, as exemplified by the following: interferon α from Sumitomo Pharmaceutical Co., Ltd. as Sumiferon (tradename); interferon α-2a from Takeda Pharmaceutical Co., Ltd. as Canferon-A (tradename); interferon α-2b from Schering-Plough Corp. as Intron A (tradename); interferon β from Mochida Pharmaceutical Co., Ltd. as IFNβ (tradename); interferon γ-1a from Shionogi & Co., Ltd. as Immunomax-γ (tradename); and interferon γ-n1 from Otsuka Pharmaceutical Co., Ltd. as Ogamma (tradename).

The above-mentioned biological response modifiers are commercially available, as exemplified by the following: krestin from Sankyo Co., Ltd. as Krestin (tradename); lentinan from Aventis Corp. as Lentinan (tradename); sizofuran from Kaken Seiyaku Co., Ltd. as Sonifuran (tradename); picibanil from Chugai Pharmaceutical Co., Ltd. as Picibanil (tradename); and ubenimex from Nippon Kayaku Co., Ltd. as Bestatin (tradename).

The above-mentioned other anticancer agents are commercially available, as exemplified by the following: mitoxantrone from Wyeth Lederle Japan, Ltd. as Novantrone (tradename); L-asparaginase from Kyowa Hakko Kogyo Co., Ltd. as Leunase (tradename); procarbazine from Nippon Roche Co., Ltd. as Natulan (tradename); dacarbazine from Kyowa Hakko Kogyo Co., Ltd. as Dacarbazine (tradename); hydroxycarbamide from Bristol-Myers Squibb Co. as Hydrea (tradename); pentostatin from Kagaku Oyobi Kessei Ryoho Kenkyusho as Coforin (tradename); tretinoin from Nippon Roche Co., Ltd. As Vesanoid (tradename); alefacept from Biogen Idec Inc. as Amevive (tradename); darbepoetin alfa from Amgen Inc. as Aranesp (tradename); anastrozole from AstraZeneca Corp. as Arimidex (tradename); exemestane from Pfizer Inc. as Aromasin (tradename); bicalutamide from AstraZeneca Corp. as Casodex (tradename); leuprorelin from Takeda Pharmaceutical Co., Ltd. as Leuplin (tradename); flutamide from Schering-Plough Corp. as Eulexin (tradename); fulvestrant from AstraZeneca Corp. as Faslodex (tradename); pegaptanib octasodium from Gilead Sciences, Inc. as Macugen (tradename); denileukin diftitox from Ligand Pharmaceuticals Inc. as Ontak (tradename); aldesleukin from Chiron Corp. as Proleukin (tradename); thyrotropin alfa from Genzyme Corp. as Thyrogen (tradename); arsenic trioxide from Cell Therapeutics, Inc. as Trisenox (tradename); bortezomib from Millennium Pharmaceuticals, Inc. as Velcade (tradename); capecitabine from Hoffmann-La Roche, Ltd. as Xeloda (tradename); and goserelin from AstraZeneca Corp. as Zoladex (tradename).

The invention also relates to a method for the treatment of cancer, which comprises administering to a subject in need thereof a therapeutically-effective amount of the compound of the invention or a pharmaceutically acceptable salt or ester thereof.

In the process according to the invention, preferred therapeutic unit may vary in accordance with, for example, the administration route of the compound of the invention, the type of the compound of the invention used, and the dosage form of the compound of the invention used; the type, administration route and dosage form of the other anticancer agent used in combination; and the type of cells to be treated, the condition of patient, and the like. The optimal treatment under the given conditions can be determined by a person skilled in the art, based on the set conventional therapeutic unit and/or based on the content of the present specification.

In the process according to the invention, the therapeutic unit for the compound of the invention may vary in accordance with, specifically, the type of compound used, the type of compounded composition, application frequency and the specific site to be treated, seriousness of the disease, age of the patient, doctor's diagnosis, the type of cancer, or the like. However, as an exemplary reference, the daily dose for an adult may be within a range of, for example, 1 to 1,000 mg in the case of oral administration. In the case of parenteral administration, preferably intravenous administration, and more preferably intravenous drip infusion, the daily dose may be within a range of, for example, 1 to 100 mg/m$^2$ (body surface area). Here, in the case of intravenous drip infusion, administration may be continuously carried out for, for example, 1 to 48 hours. Moreover, the administration frequency may vary depending on the administering method and symptoms, but it is, for example, once to five times a day. Alternatively, periodically intermittent administration such as administration every other day, administration every two days or the like may be employed as well in the administering method. The period of withdraw from medication in the case of parenteral administration is, for example, 1 to 6 weeks.

Although the therapeutic unit for the other anticancer agent used in combination with the compound of the invention is not particularly limited, it can be determined, if needed, by those skilled in the art according to known literatures. Examples may be as follows.

The therapeutic unit of 5-fluorouracil (5-FU) is such that, in the case of oral administration, for example, 200 to 300 mg per day is administered in once to three times consecutively, and in the case of injection, for example, 5 to 15 mg/kg per day is administered once a day for the first 5 consecutive days by intravenous injection or intravenous drip infusion, and then 5 to 7.5 mg/kg is administered once a day every other day by intravenous injection or intravenous drip infusion (the dose may be appropriately increased or decreased).

The therapeutic unit of S-1 (Tegafur, Gimestat and Ostat potassium) is such that, for example, the initial dose (singe dose) is set to the following standard amount in accordance with the body surface area, and it is orally administered twice a day, after breakfast and after dinner, for 28 consecutive days, followed by withdrawal from medication for 14 days. This is set as one course of administration, which is repeated. The initial standard amount per unit body surface area (Tegafur equivalent) is 40 mg in one administration for an area less than 1.25 m$^2$; 50 mg in one administration for an area of 1.25 m$^2$ to less than 1.5 m$^2$; 60 mg in one administration for an area of 1.5 m$^2$ or more. This dose is appropriately increased or decreased depending on the condition of the patient.

The therapeutic unit for gemcitabine is, for example, 1 g as gemcitabine/m$^2$ in one administration, which is administered by intravenous drip infusion over a period of 30 minutes, and one administration per week is continued for 3 weeks, followed by withdrawal from medication on the fourth week. This is set as one course of administration, which is repeated. The dose is appropriately decreased in accordance with age, symptom or development of side-effects.

The therapeutic unit for doxorubicin (e.g., doxorubicin hydrochloride) is such that, for example, in the case of intravenous injection, 10 mg (0.2 mg/kg) (titer) is administered once a day by intravenous one-shot administration for 4 to 6 consecutive days, followed by withdrawal from medication for 7 to 10 days. This is set as one course of administration, which is repeated two or three times. Here, the total dose is preferably 500 mg (titer)/m$^2$ (body surface area) or less, and it may be appropriately increased or decreased within the range.

The therapeutic unit for etoposide is such that, for example, in the case of intravenous injection, 60 to 100 mg/m$^2$ (body surface area) per day is administered for 5 consecutive days, followed by withdrawal from medication for three weeks (the dose may be appropriately increased or decreased). This is set as one course of administration, which is repeated. Meanwhile, in the case of oral administration, for example, 175 to 200 mg per day is administered for 5 consecutive days, followed by withdrawal from medication for three weeks (the dose may be appropriately increased or decreased). This is set as one course of administration, which is repeated.

The therapeutic unit for docetaxel (docetaxel hydrate) is such that, for example, 60 mg as docetaxel/m$^2$ (body surface area) is administered once a day by intravenous drip infusion over a period of 1 hour or longer at an interval of 3 to 4 weeks (the dose may be appropriately increased or decreased).

The therapeutic unit of paclitaxel is such that, for example, 210 mg/m$^2$ (body surface area) is administered once a day by intravenous drip infusion over a period of 3 hours, followed by withdrawal from medication for at least 3 weeks. This is set as one course of administration, which is repeated. The dose may be appropriately increased or decreased.

The therapeutic unit for cisplatin is such that, for example, in the case of intravenous injection, 50 to 70 mg/m$^2$ (body surface area) is administered once a day, followed by withdrawal from medication for 3 weeks or longer (the dose may be appropriately increased or decreased). This is set as one course of administration, which is repeated.

The therapeutic unit for carboplatin is such that, for example, 300 to 400 mg/m² is administered once a day by intravenous drip infusion over a period of 30 minutes or longer, followed by withdrawal from medication for at least 4 weeks (the dose may be appropriately increased or decreased). This is set as one course of administration, which is repeated.

The therapeutic unit for oxaliplatin is such that 85 mg/m² is administered once a day by intravenous injection, followed by withdrawal from medication for two weeks. This is set as one course of administration, which is repeated.

The therapeutic unit for irinotecan (e.g., irinotecan hydrochloride) is such that, for example, 100 mg/m² is administered once a day by intravenous drip infusion for 3 or 4 times at an interval of one week, followed by withdrawal from medication for at least two weeks.

The therapeutic unit for topotecan is such that, for example, 1.5 mg/m² is administered once a day by intravenous drip infusion for 5 days, followed by withdrawal from medication for at least 3 weeks.

The therapeutic unit for cyclophosphamide is such that, for example, in the case of intravenous injection, 100 mg is administered once a day by intravenous injection for consecutive days. If the patient can tolerate, the daily dose may be increased to 200 mg. The total dose is 3,000 to 8,000 mg, which may be appropriately increased or decreased. If necessary, it may be injected or infused intramuscularly, intrathoracically or intratumorally. On the other hand, in the case of oral administration, for example, 100 to 200 mg is administered a day.

The therapeutic unit for gefitinib is such that 250 mg is orally administered once a day.

The therapeutic unit for cetuximab is such that, for example, 400 mg/m² is administered on the first day by intravenous drip infusion, and then 250 mg/m² is administered every week by intravenous drip infusion.

The therapeutic unit for bevacizumab is such that, for example, 3 mg/kg is administered every week by intravenous drip infusion.

The therapeutic unit for trastuzumab is such that, for example, typically for an adult, once a day, 4 mg as trastuzumab/kg (body weight) is administered initially, followed by intravenous drip infusion of 2 mg/kg over a period of 90 minutes or longer every week from the second administration.

The therapeutic unit for exemestane is such that, for example, typically for an adult, 25 mg is orally administered once a day after meal.

The therapeutic unit for leuprorelin (e.g., leuprorelin acetate) is such that, for example, typically for an adult, 11.25 mg is subcutaneously administered once in 12 weeks.

The therapeutic unit for imatinib is such that, for example, typically for an adult in the chronic phase of chronic myelogenous leukemia, 400 mg is orally administered once a day after meal.

The therapeutic unit for a combination of 5-FU and leucovorin is such that, for example, 425 mg/m² of 5-FU and 200 mg/m² of leucovorin are administered from the first day to the fifth day by intravenous drip infusion, and this course is repeated at an interval of 4 weeks.

The compounds of the invention have an excellent Wee1 kinase inhibitory effect, and therefore are useful in the field of medicine, especially in the field of treatment of various cancers.

The present invention is described below in more detail based on examples and production examples. It should be noted, however, that the invention is in no way limited by the following descriptions.

EXAMPLES

In the thin-layer chromatography of the following examples and production examples, a Silica Gel$_{60}$F$_{254}$ (Merck) was used as the plate, and the detection was made using a UV detector. As the column silica gel, Wakogel™ C-300 or C-200 (Wako Pure Chemical Industries, Ltd.), or NH (Fuji Silysia Chemical) was used. MS spectra were measured using JMS-SX102A (JEOL) or QUATTRO II (Micromass). In the measurement of NMR spectra, dimethyl sulfoxide was used as the internal reference when using a deuterated dimethyl sulfoxide solution, and measurements were made using a JNM-AL 400 (400 MHz; JEOL), Mercury 400 (400 MHz; Varian), or Inova 400 (400 MHz; Varian) spectrometer. All δ values are given in ppm.

The meaning of the abbreviations used in the examples and production examples are as follows.

s: Singlet
d: Doublet
dd: Double doublet
ddd: Double double doublet
t: Triplet
dt: Double triplet
ddt: Double double triplet
q: Quartet
m: Multiplet
br: Broad
J: Coupling constant
Hz: Hertz
DMSO-d$_6$: Deuterated dimethyl sulfoxide
CDCl$_3$: Deuterated chloroform
CD$_3$OD: Deuterated methanol
mCPBA: 3-chlorobenzoic acid
DIPEA: N,N-diisopropylethylamine
TsOH: p-toluenesulfonic acid Production Example 1

Production of 7-Chloro-3-(2,6-dichlorophenyl)-4-imino-3,4-dihydropyrimido[4,5-d]pyrimidin-2(1H)-one

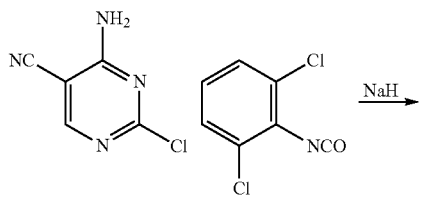

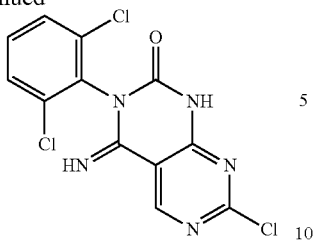

1.12 g of sodium hydride was added to an N,N-dimethylformamide (35 mL) solution containing 3.0 g of 4-amino-2-chloropyrimidin-5-carbonitrile, and the mixture was stirred for 5 minutes at room temperature. Then, 4.38 g of 2,6-dichlorophenyl isocyanate was added to the reaction mixture, which was then stirred for 1 hour at room temperature. Thereafter, ethyl acetate and a 1 N hydrochloric acid aqueous solution were added to the reaction mixture to separate the organic layer. After washing with saturated saline, the solution was dried with anhydrous magnesium sulfate, and the solvent was distilled away. The deposited solid was solidified using a methanol-ethyl acetate mixed solvent. After leaching, 3.8 g of a white solid was obtained as a subject compound.

$^1$H-NMR (400 MHz, DMSO-$d_6$) δ: 9.33 (1H, s), 7.66 (2H, d, J=8.2 Hz), 7.53 (1H, t, J=8.2 Hz).

ESI-MS Found: m/z[M+H] 342

Production Example 2

Production of 7-Chloro-3-(2,6-dichlorophenyl)-4-imino-1-methyl-3,4-dihydropyrimido[4,5-d]pyrimidin-2(1H)-one

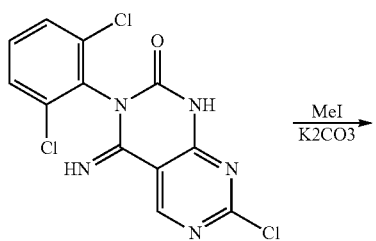

484 mg of potassium carbonate and 456 mg of methyl iodide were added to a 5-mL N,N-dimethylformamide solution containing 1.00 g of the 7-chloro-3-(2,6-dichlorophenyl)-4-imino-3,4-dihydropyrimido[4,5-d]pyrimidin-2(1H)-one obtained in Production Example 1, and the mixture was stirred for 1 hour at room temperature. The reaction mixture was added to ethyl acetate and a 0.5 N hydrochloric acid aqueous solution with stirring to separate the organic layer. After washing with saturated saline, the solution was dried with anhydrous sodium sulfate, and the solvent was distilled away. The crude product was solidified using chloroform-methanol-hexane, and 700 mg of a yellow solid was obtained as a subject compound.

$^1$H-NMR (400 MHz, DMSO-$d_6$) δ: 9.78 (1H, s), 9.44 (1H, s), 7.67 (2H, d, J=8.0 Hz), 7.54 (1H, t, J=8.0 Hz) 3.48 (1H, s).

ESI-MS Found: m/z[M+H]$^+$ 356

Example 1

Production of 3-(2,6-Dichlorophenyl)-7-({4-[4-(2-hydroxyethyl)piperazin-1-yl]phenyl}amino)-4-imino-1-methyl-3,4-dihydropyrimido[4,5-d]pyrimidin-2(1H)-one

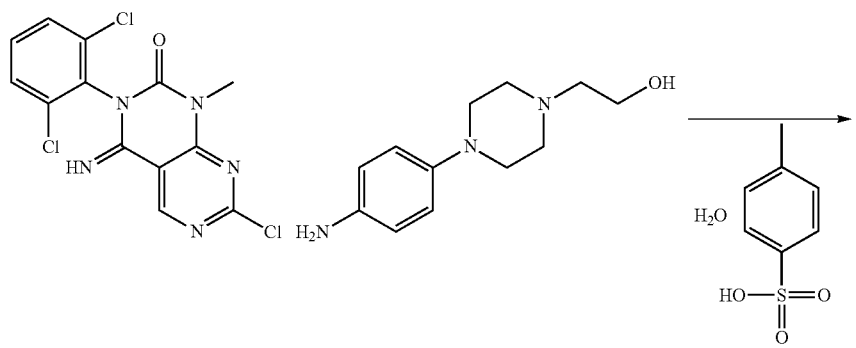

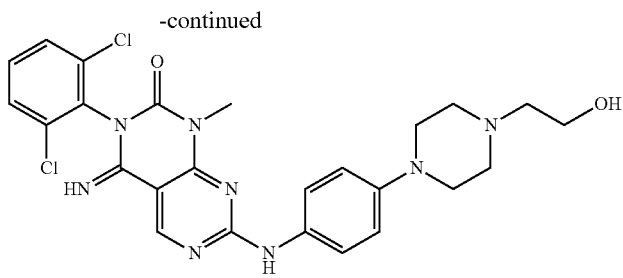

30 mg of the 7-chloro-3-(2,4-dichloropyridin-3-yl)-4-imino-1-methyl-3,4-dihydropyrimido[4,5-d]pyrimidin-2(1H)-one obtained in Production Example 2, and 16 mg of TsOH monohydrate were added to a 5-ml n-butanol solution containing 18.6 mg of 2-[4-(4-aminophenyl)piperazin-1-yl]ethanol, and the mixture was heat stirred for 15 minutes at 100° C. The reaction mixture was concentrated under reduced pressure, and purified by basic column chromatography. As a result, 21 mg of a white solid was obtained as a subject compound.

$^1$H-NMR (400 MHz, CD$_3$OD) δ: 8.97 (1H, s), 7.60-7.46 (5H, m), 7.00 (2H, d, J=8.8 Hz), 3.76 (2H, br s), 3.61 (3H, s), 3.24 (4H, br), 2.76 (4H, br s), 2.64 (2H, br).
ESI-MS Found: m/z[M+H] 542

Example 2

Production of 3-(2,6-Dichlorophenyl)-7-({4-[2-(hydroxymethyl)morpholin-4-yl]phenyl}amino)-4-imino-1-methyl-3,4-dihydropyrimido[4,5-d]pyrimidin-2(1H)-one

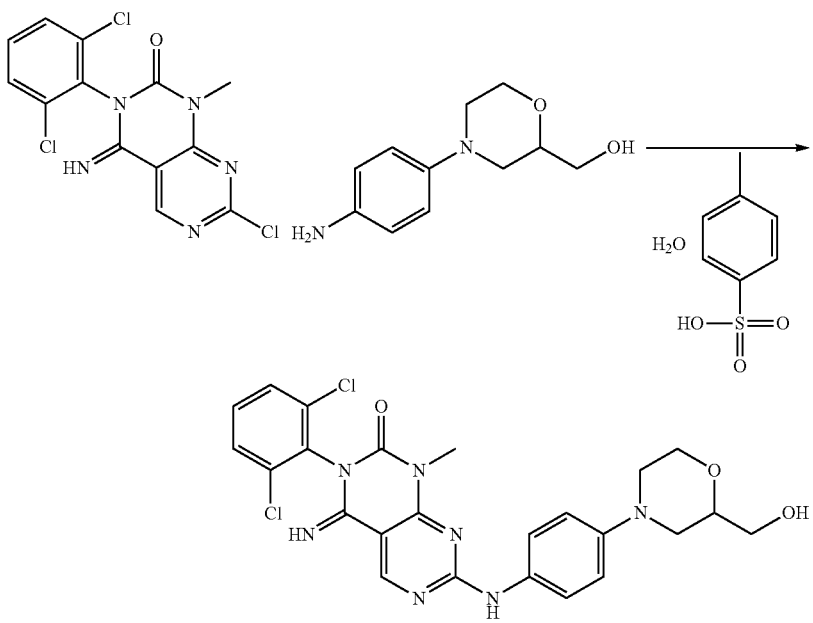

30 mg of the 7-chloro-3-(2,4-dichloropyridin-3-yl)-4-imino-1-methyl-3,4-dihydropyrimido[4,5-d]pyrimidin-2(1H)-one obtained in Production Example 2, and 16 mg of TsOH monohydrate were added to a 5-ml n-butanol solution containing 17.5 mg of 4-[4-(aminophenyl)morpholin-2-yl]methanol, and the mixture was heat stirred for 15 minutes at 100° C. The reaction mixture was concentrated under reduced pressure, and purified by basic column chromatography. As a result, 11 mg of a white solid was obtained as a subject compound.

$^1$H-NMR (400 MHz, CD$_3$OD) δ: 9.00 (1H, s), 7.58-7.47 (5H, m), 6.97 (2H, d, J=8.8 Hz), 4.04-4.01 (1H, m), 3.83-3.72 (2H, m), 3.67-3.60 (2H, m), 3.50 (3H, s), 3.47-3.39 (1H, m), 3.38-3.30 (1H, m), 2.85-3.79 (1H, m), 2.60-2.54 (1H, m).
ESI-MS Found: m/z[M+H] 529

Example 3

Production of 3-(2,6-Dichlorophenyl)-7-[(4-{4-[(dimethylamino)acetyl]piperazin-1-yl}phenyl)amino]-4-imino-1-methyl-3,4-dihydropyrimido[4,5-d]pyrimidin-2(1H)-one

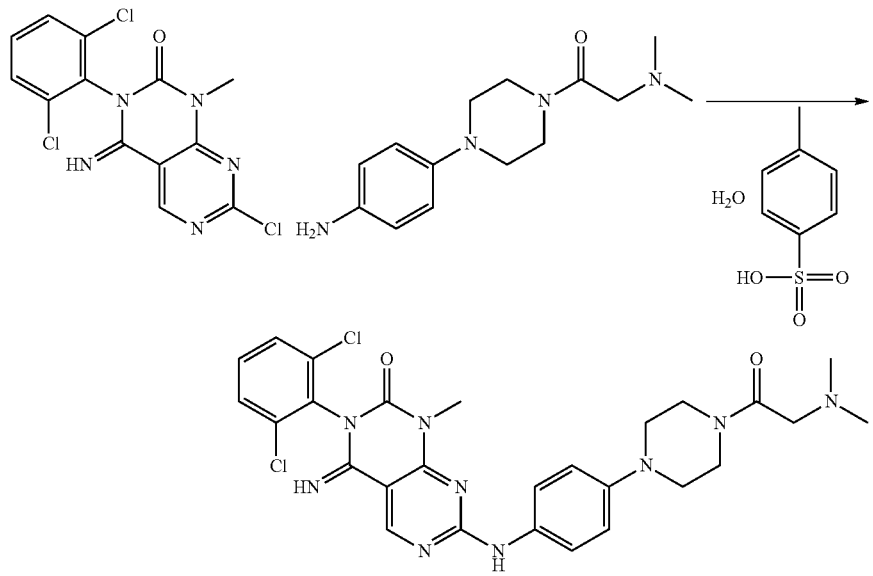

30 mg of the 7-chloro-3-(2,4-dichloropyridin-3-yl)-4-imino-1-methyl-3,4-dihydropyrimido[4,5-d]pyrimidin-2(1H)-one obtained in Production Example 2, and 16 mg of TsOH monohydrate were added to a 5-ml n-butanol solution containing 22.1 mg of 1-[4-(4-aminophenyl)piperazin-1-yl]-2-(dimethylamino)ethanone, and the mixture was heat stirred for 15 minutes at 100° C. The reaction mixture was concentrated under reduced pressure, and purified by basic column chromatography. As a result, 37 mg of a white solid was obtained as a subject compound.

$^1$H-NMR (400 MHz, CD$_3$OD) δ: 8.97 (1H, s), 7.63-7.56 (3H, m), 7.51-7.47 (2H, m), 7.00 (2H, d, J=8.8 Hz), 3.77 (4H, br), 3.61 (3H, s), 3.23 (2H, s), 3.21-3.18 (4H, br), 2.34 (6H, s).
ESI-MS Found: m/z[M+H] 583

Example 4

Production of 3-(2,6-Dichlorophenyl)-7-[(4-{2-[(dimethylamino)methyl]morpholin-4-yl}phenyl)amino]-4-imino-1-methyl-3,4-dihydropyrimido[4,5-d]pyrimidin-2(1H)-one

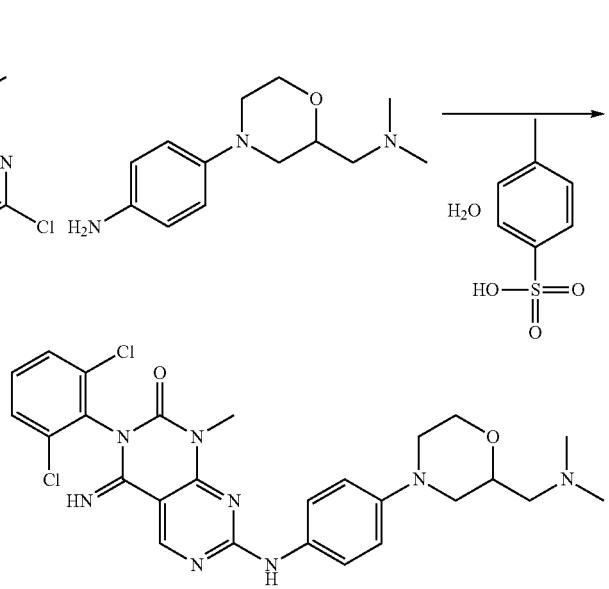

30 mg of the 7-chloro-3-(2,4-dichloropyridin-3-yl)-4-imino-1-methyl-3,4-dihydropyrimido[4,5-d]pyrimidin-2(1H)-one obtained in Production Example 2, and 16 mg of TSOH monohydrate were added to a 5-ml n-butanol solution containing 20 mg of 4-{2-[(dimethylamino)methyl]morpholin-4-yl}aniline, and the mixture was heat stirred for 15 minutes at 100° C. The reaction mixture was concentrated under reduced pressure, and purified by basic column chromatography. As a result, 27 mg of a white solid was obtained as a subject compound.

1H-NMR (400 MHz, CD$_3$OD) δ: 9.05 (1H, s), 7.60-7.50 (5H, m), 7.00 (2H, d, J=8.8 Hz), 4.07-4.03 (1H, m), 3.86-3.61 (2H, m), 3.52 (3H, s), 3.46-3.35 (2H, m), 2.86-2.80 (1H, m), 2.60-2.48 (2H, m), 2.42-2.37 (1H, m), 2.33 (6H, s).

ESI-MS Found: m/z[M+H] 556

Example 5

Production of 3-(2,6-Dichlorophenyl)-4-imino-7-{[4-(4-methylpiperazin-1-yl)phenyl]amino}-3,4-dihydropyrimido[4,5-d]pyrimidin-2(1H)-one (1) Production of 4-Amino-2-{[4-(4-methylpiperazin-1-yl)phenyl]amino}pyrimidine-5-carbonitrile

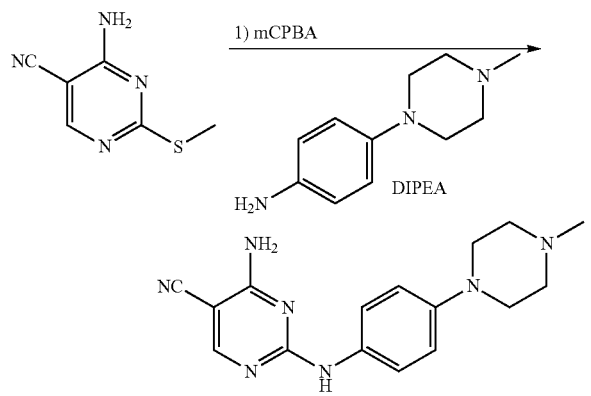

1.91 g of mCPBA was added to a tetrahydrofuran (100 mL) solution containing 1 g of 4-amino-2-(methylsulfanyl)pyrimidine-5-carbonitrile. The mixture was stirred at room temperature for 10 minutes, and the solvent was distilled away. The resulting crude product was dissolved in toluene/N,N-dimethylformamide (80 ml/20 ml), and 1.15 g of 4-(4-methylpiperazin-1-yl)aniline, and 2.3 g of DIPEA were added to the mixture, which was then stirred at 80° C. for 4 hours. The solvent was distilled away after cooling the reaction mixture. Then, water was added, and the mixture was extracted with ethyl acetate. After washing the organic layer with saturated saline, the solution was dried with anhydrous magnesium sulfate and concentrated. The resulting crude product was purified by basic silica gel column chromatography, and 720 mg of a white solid was obtained as a subject compound.

$^1$H-NMR (400 MHz, CD$_3$OD) δ: 8.19 (1H, s), 7.48 (2H, d, J=8.0 Hz), 6.96 (2H, d, J=8.0 Hz), 3.19 (4H, br), 2.65 (4H, br), 2.37 (3H, s).

ESI-MS Found: m/z[M+H] 310

(2) Production of 3-(2,6-Dichlorophenyl)-4-imino-7-{[4-(4-methylpiperazin-1-yl)phenyl]amino}-3,4-dihydropyrimido[4,5-d]pyrimidin-2(1H)-one

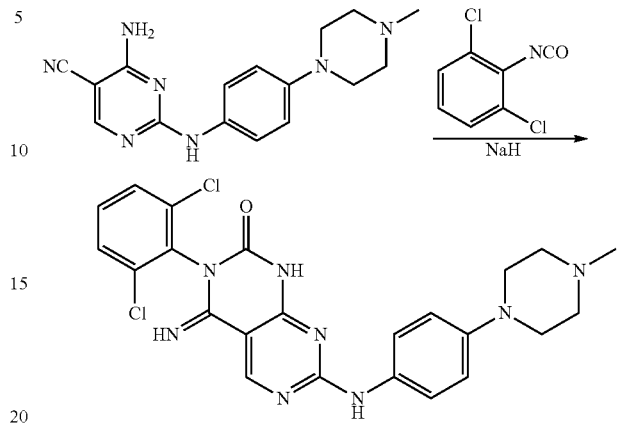

643 mg of sodium hydride was added to an N,N-dimethylformamide (25 mL) solution containing 1.38 g of the compound obtained in (1), and the mixture was stirred at room temperature for 5 minutes. Then, 1.01 g of 2,6-dichlorophenyl isocyanate was added to the reaction mixture, which was then stirred at room temperature for 90 minutes. The reaction mixture was neutralized by adding water, and subsequently chloroform and a 5 N hydrochloric acid aqueous solution to separate the organic layer. After washing with saturated saline, the solution was dried with anhydrous magnesium sulfate, and the solvent was distilled away. The resulting crude product was purified by basic silica gel column chromatography, and solidified using ethyl acetate-hexane-chloroform. As a result, 1 g of a white solid was obtained as a subject compound.

$^1$H-NMR (400 MHz, CD$_3$OD) δ: 8.93 (1H, s), 7.56 (2H, d, J=8.8 Hz), 7.55-7.53 (2H, m), 7.46 (1H, t, J=8.8 Hz), 6.97 (2H, d, J=8.8 Hz), 3.20 (4H, br s), 2.65 (4H, br s), 2.38 (3H, s).

ESI-MS Found: m/z[M+H] 497.

Example 6

Production of 3-(2,6-Dichlorophenyl)-4-imino-7-{[3-methyl-4-(4-methylpiperazin-1-yl)phenyl]amino}-3,4-dihydropyrimido[4,5-d]pyrimidin-2(1H)-one (1) Production of 4-Amino-2-{[3-methyl-4-(4-methylpiperazin-1-yl)phenyl]amino}pyrimidine-5-carbonitrile

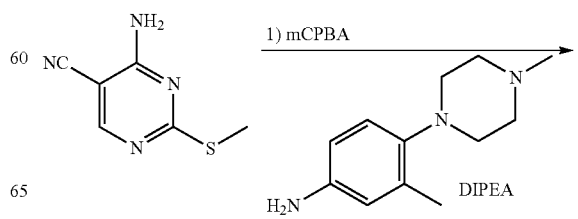

-continued

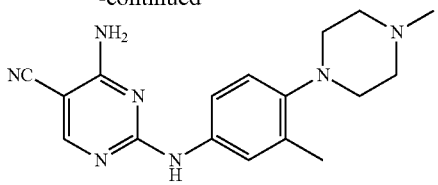

145 mg of mCPBA was added to a chloroform (20 mL) solution containing 70 mg of 4-amino-2-(methylsulfanyl)pyrimidine-5-carbonitrile. The mixture was stirred at room temperature for 10 minutes, and the solvent was distilled away. The resulting crude product was dissolved in toluene/N,N-dimethylformamide (10 ml/1 ml), and 86 mg of 3-methyl-4-(4-methylpiperazin-1-yl)aniline, and 163 mg of DIPEA were added to the mixture, which was then stirred at 80° C. for 4 hours. The solvent was distilled away after cooling the reaction mixture. Then, water was added, and the mixture was extracted with ethyl acetate. After washing the organic layer with saturated saline, the solution was dried with anhydrous magnesium sulfate and concentrated. The resulting crude product was purified by basic silica gel column chromatography, and 65 mg of a white solid was obtained as a subject compound.

ESI-MS Found: m/z[M+H] 324

(2) Production of 3-(2,6-Dichlorophenyl)-4-imino-7-{[3-methyl-4-(4-methylpiperazin-1-yl)phenyl]amino}-3,4-dihydropyrimido[4,5-d]pyrimidin-2(1H)-one

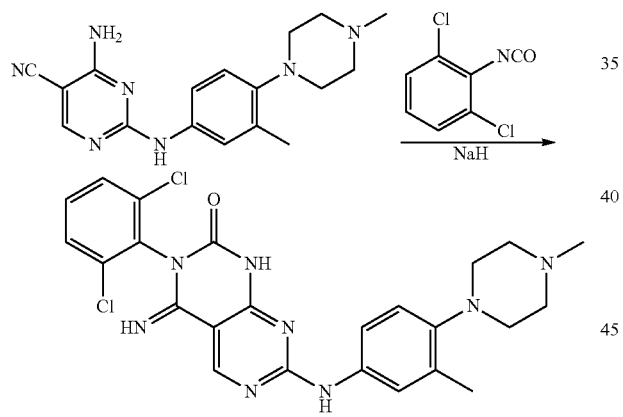

24 mg of sodium hydride was added to an N,N-dimethylformamide (3 mL) solution containing 65 mg of the compound obtained in (1), and the mixture was stirred at room temperature for 5 minutes. Then, 49 mg of 2,6-dichlorophenyl isocyanate was added to the reaction mixture, which was then stirred at room temperature for 30 minutes. The reaction mixture was neutralized by adding water, and subsequently chloroform and a 1 N hydrochloric acid aqueous solution to separate the organic layer. After washing with saturated saline, the solution was dried with anhydrous magnesium sulfate, and the solvent was distilled away. The resulting crude product was purified by basic silica gel column chromatography, and solidified using methanol. As a result, 72 mg of a white solid was obtained as a subject compound.

$^1$H-NMR (400 MHz, CD$_3$OD) δ: 8.93 (1H, s), 7.56 (2H, d, J=8.8 Hz), 7.55-7.53 (2H, m), 7.46 (1H, t, J=8.8 Hz), 6.97 (2H, d, J=8.8 Hz), 3.20 (4H, br s), 2.65 (4H, br s), 2.38 (3H, s).

ESI-MS Found: m/z[M+H] 512.

Example 7

Production of 3-(2,6-Dichlorophenyl)-4-imino-1-methyl-7-{[4-(4-methylpiperazin-1-yl)phenyl]amino}-3,4-dihydropyrimido[4,5-d]pyrimidin-2(1H)-one

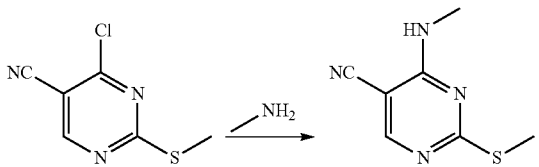

(1) Production of 4-(Methylamino)-2-(methylsulfanyl)pyrimidine-5-carbonitrile 3 ml of a methylamine-methanol solution, and 246 mg of triethylamine were added to a tetrahydrofuran (10 mL) solution containing 150 mg of 4-chloro-2-(methylsulfanyl)pyrimidine-5-carbonitrile, and the mixture was stirred for 30 minutes at room temperature. After adding water, the solution was extracted with ethyl acetate, and dried with anhydrous magnesium sulfate. After concentration, 134 mg of a white solid was obtained as a subject compound.

ESI-MS Found: m/z[M+H] 181

(2) Production of 4-(Methylamino)-2-{[4-(4-methylpiperazin-1-yl)phenyl]amino}pyrimidine-5-carbonitrile

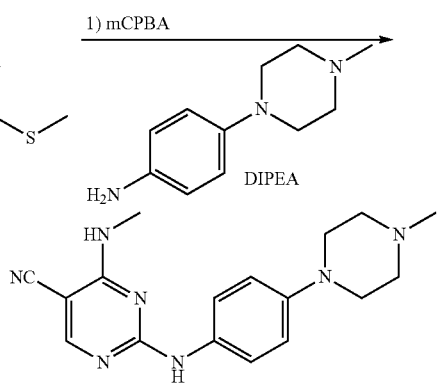

248 mg of mCPBA was added to a 3:1 toluene-tetrahydrofuran (30 mL) solution containing 130 mg of 4-(methylamino)-2-(methylsulfanyl)pyrimidine-5-carbonitrile, and the mixture was stirred at room temperature for 15 minutes. Then, 138 mg of 4-(4-methylpiperazin-1-yl)aniline, and 280 mg of DIPEA were added to the mixture, which was then stirred at 80° C. for 8 hours. The solvent was distilled away after cooling the reaction mixture. Then, water was added, and the solution was extracted with ethyl acetate. The organic layer was washed with saturated saline, and the solution was concentrated after drying with anhydrous magnesium sulfate. The resulting crude product was purified by basic silica gel column chromatography, and 170 mg of a white solid was obtained as a subject compound.

ESI-MS Found: m/z[M+H] 324

(3) Production of 3-(2,6-Dichlorophenyl)-4-imino-1-methyl-7-{[4-(4-methylpiperazin-1-yl)phenyl]amino}-3,4-dihydropyrimido[4,5-d]pyrimidin-2(1H)-one

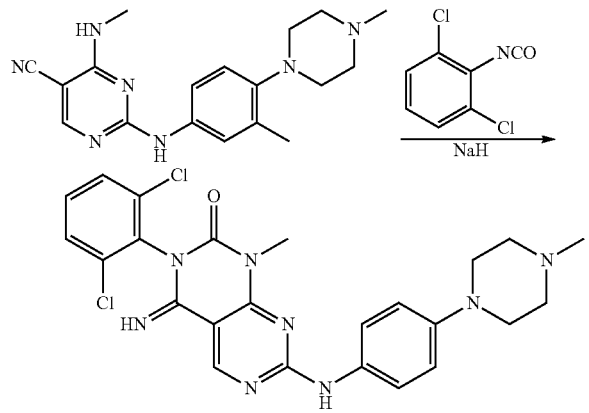

22 mg of sodium hydride was added to an N,N-dimethylformamide (5 mL) solution containing 50 mg of the compound obtained in (1), and the mixture was stirred at room temperature for 5 minutes. Then, 35 mg of 2,6-dichlorophenyl isocyanate was added to the reaction mixture, which was then stirred at room temperature for 60 minutes. The reaction mixture was neutralized by adding water, and subsequently chloroform and a 1 N hydrochloric acid aqueous solution to separate the organic layer. After washing with saturated saline, the solution was dried with anhydrous magnesium sulfate, and the solvent was distilled away. The resulting crude product was purified by basic silica gel column chromatography, and solidified using ethyl acetate-hexane-chloroform. As a result, 35 mg of a white solid was obtained as a subject compound.

$^1$H-NMR (400 MHz, CD$_3$OD) δ: 9.05 (1H, s), 7.65-7.51 (5H, m), 7.00 (2H, d, J=8.8 Hz), 3.61 (3H, s), 3.24 (4H, br s), 2.66 (4H, br s), 2.38 (3H, s).

ESI-MS Found: m/z[M+H] 511

Example 8

Production of 3-(2,6-Dichlorophenyl)-7-({4-[(3R)-3-dimethylaminopyrrolidin-1-yl]phenyl}amino)-4-imino-3,4-dihydropyrimido[4,5-d]pyrimidin-2(1H)-one

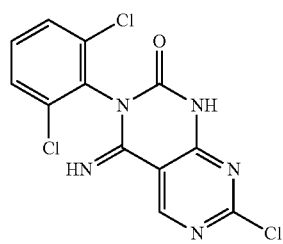

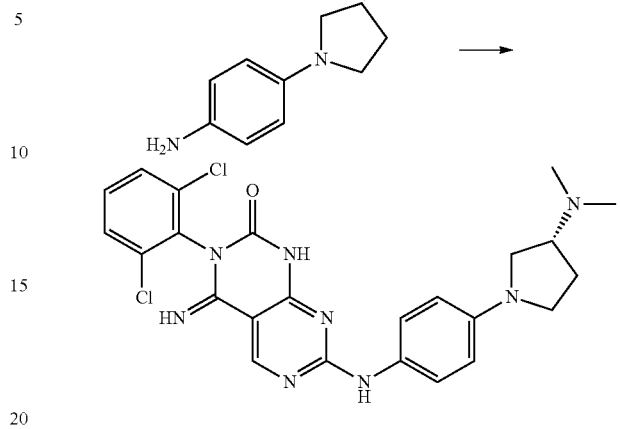

18.8 mg of a yellow solid was obtained as a subject compound as in Example 4, except that the 7-chloro-3-(2,6-dichlorophenyl)-4-imino-3,4-dihydropyrimido[4,5-d]pyrimidin-2(1H)-one obtained in Production Example 1 was used instead of the 7-chloro-3-(2,4-dichloropyridin-3-yl)-4-imino-1-methyl-3,4-dihydropyrimido[4,5-d]pyrimidin-2(1H)-one used in Example 4, and that (3R)-1-(4-aminophenyl)-N,N-dimethylpyrrolidin-3-amine was used instead of the 4-{2-[(dimethylamino)methyl]morpholin-4-yl}aniline used in Example 4.

$^1$H-NMR (400 MHz, DMSO-d6) δ: 11.62 (1H, s), 9.02 (1H, s), 8.76 (1H, s), 7.73-7.58 (3H, m), 7.46 (1H, t, J=8.0 Hz), 6.50 (2H, d, J=9.3 Hz), 3.41 (1H, t, J=8.3 Hz), 3.21 (1H, dd, J=16.1, 9.3 Hz), 3.02 (1H, t, J=8.5 Hz), 2.80 (1H, br s), 2.20 (6H, s), 2.16-2.11 (1H, m), 1.80 (1H, t, J=10.5 Hz).

ESI-MS Found: m/z[M+H] 511

Compounds of Examples 9 to 28, and 1a to 82a below were obtained as in the foregoing examples, using appropriately corresponding raw materials. (Note that, in the structural formulae above and below, the symbol for the hydrogen atoms of the groups —NH— and —NH$_2$ may be omitted for simplicity, and such groups are also represented by —N— and —N, respectively.)

Example 9

3-(2,6-Dichlorophenyl)-4-imino-7-{[4-(5-methyl-hexahydropyrrolo[3,4-b]pyrrol-1(2H)-yl)phenyl]amino)-3,4-dihydropyrimido[4,5-d]pyrimidin-2(1H)-one

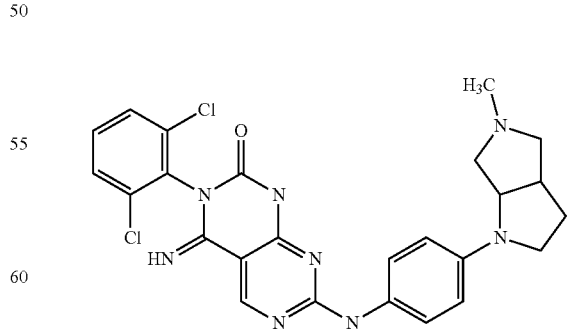

$^1$H-NMR (400 MHz, CD$_3$OD) δ: 8.91 (1H, s), 7.57-7.46 (5H, m), 6.60 (2H, d, J=8.5 Hz), 4.13-3.50 (1H, m), 3.10-2.53 (6H, m), 2.30 (3H, s), 2.28-1.73 (3H, m).

ESI-MS Found: m/z[M+H] 523

Example 10

3-(2,6-Dichlorophenyl)-4-imino-7-{[4-(2-methyl-2,7-diazaspiro[4,5]dec-7-yl)phenyl]amino)-3,4-dihydropyrimido[4,5-d]pyrimidin-2(1H)-one

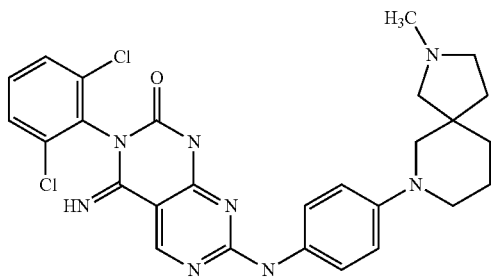 [SMILES: CN1CCC2(CCCN(c3ccc(Nc4ncc5c(=N)n(-c6c(Cl)cccc6Cl)c(=O)[nH]c5n4)cc3)C2)C1]

$^1$H-NMR (400 MHz, CD$_3$OD) δ: 8.90 (1H, s), 7.51-7.31 (5H, m), 6.85 (2H, d, J=8.0 Hz), 3.44-3.38 (2H, m), 3.04-2.64 (6H, m), 2.27 (3H, s), 1.73-1.24 (6H, m).

ESI-MS Found: m/z[M+H] 551

Example 11

3-(2,6-Dichlorophenyl)-4-imino-7-{[4-(1-methylhexahydropyrrolo[3,4-b]pyrrol-5(1H)-yl)phenyl]amino}-3,4-dihydropyrimido[4,5-d]pyrimidin-2(1H)-one

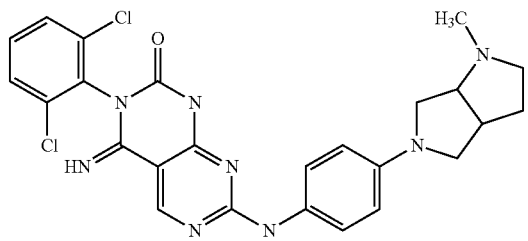 [SMILES: CN1CCC2CN(c3ccc(Nc4ncc5c(=N)n(-c6c(Cl)cccc6Cl)c(=O)[nH]c5n4)cc3)CC21]

$^1$H-NMR (400 MHz, CD$_3$OD) δ: 8.93 (1H, s), 7.60-7.44 (5H, m), 6.71 (2H, d, J=8.5 Hz), 3.53-3.31 (1H, m), 3.30-3.22 (1H, m), 3.09-2.99 (5H, m), 2.37 (3H, s), 2.37-2.34 (1H, m), 2.27-2.12 (1H, m), 1.79-1.63 (1H, m).

ESI-MS Found: m/z[M+H] 524

Example 12

3-(2,6-Dichlorophenyl)-4-imino-7-({4-[(2R)-2-(methoxymethyl)-4-methylpiperazin-1-yl]phenyl}amino)-3,4-dihydropyrimido[4,5-d]pyrimidin-2(1H)-one

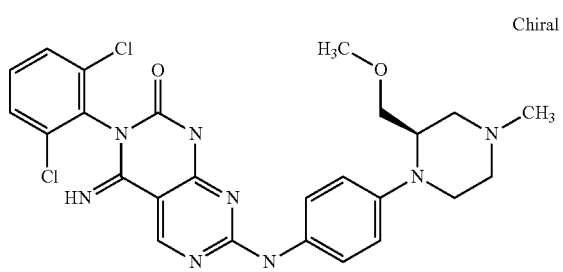 [SMILES: COC[C@H]1CN(C)CCN1c1ccc(Nc2ncc3c(=N)n(-c4c(Cl)cccc4Cl)c(=O)[nH]c3n2)cc1]

$^1$H-NMR (400 MHz, CDCl$_3$) δ: 9.16 (1H, s), 7.62-7.40 (5H, m), 6.87 (2H, d, J=9.0 Hz), 3.83-3.75 (1H, m), 3.69-3.60 (1H, m), 3.29 (3H, s), 3.28-3.25 (2H, m), 3.13-3.03 (1H, m), 2.97-2.89 (1H, m), 2.82-2.74 (1H, m), 2.37-2.19 (2H, m), 2.32 (3H, s).

ESI-MS Found: m/z[M+H] 541

Example 13

7-({4-[3-(tert-Butylamino)pyrrolidin-1-yl]phenyl}amino)-3-(2,6-dichlorophenyl)-4-imino-3,4-dihydropyrimido[4,5-d]pyrimidin-2(1H)-one

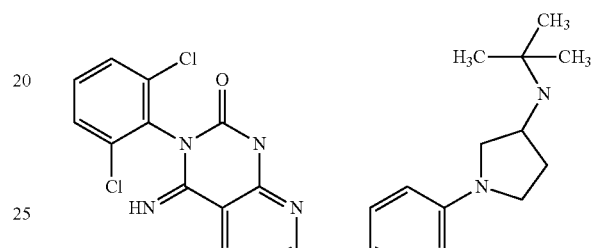

$^1$H-NMR (400 MHz, DMSO-d6) δ: 9.81 (1H, s), 9.00 (1H, s), 8.74 (1H, s), 7.66-7.44 (5H, br m), 6.45 (2H, d, J=8.8 Hz), 3.52-3.40 (2H, m), 3.32 (2H, s), 3.26 (1H, td, J=8.8, 3.4 Hz), 3.17 (1H, dd, J=16.1, 8.8 Hz), 2.82 (1H, t, J=7.6 Hz), 2.18-2.10 (1H, m), 1.74-1.64 (1H, m), 1.06 (9H, s).

ESI-MS Found: m/z[M+H] 539

Example 14

3-(2,6-Dichlorophenyl)-7-({4-[(3S)-3-(dimethylamino)pyrrolidin-1-yl]phenyl}amino)-4-imino-3,4-dihydropyrimido[4,5-d]pyrimidin-2(1H)-one

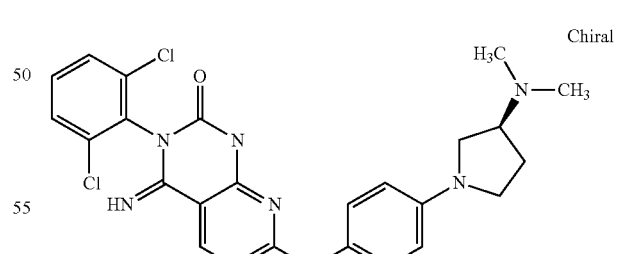

$^1$H-NMR (400 MHz, DMSO-d6) δ: 11.62 (1H, s), 9.02 (1H, s), 8.76 (1H, s), 7.73-7.58 (3H, m), 7.46 (1H, t, J=8.0 Hz), 6.50 (2H, d, J=9.3 Hz), 3.41 (1H, t, J=8.3 Hz), 3.21 (1H, dd, J=16.1, 9.3 Hz), 3.02 (1H, t, J=8.5 Hz), 2.80 (1H, br s), 2.20 (6H, s), 2.16-2.11 (1H, m), 1.80 (1H, t, J=10.5 Hz).

ESI-MS Found: m/z[M+H] 511

Example 15

7-{[4-(4-Acetylpiperazin-1-yl)-3-methylphenyl]amino}-3-(2,6-dichlorophenyl)-4-imino-3,4-dihydropyrimido[4,5-d]pyrimidin-2(1H)-one

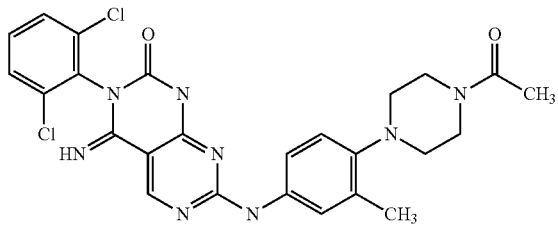 [SMILES: CC(=O)N1CCN(c2ccc(Nc3ncc4c(=N)n(-c5c(Cl)cccc5Cl)c(=O)[nH]c4n3)cc2C)CC1]

1H-NMR (400 MHz, CDCl₃) δ: 9.00 (1H, br s), 7.60-7.40 (5H, m), 7.00 (1H, d, J=8.8 Hz), 3.75 (2H, br), 3.63 (2H, br), 2.93-2.86 (4H, m), 2.35 (3H, s), 2.16 (3H, s).
ESI-MS Found: m/z[M+H] 539

Example 16

3-(2,6-Dichlorophenyl)-4-imino-7-{[4-(2-methyl-2,7-diazaspiro[3,5]non-7-yl)phenyl]amino}-3,4-dihydropyrimido[4,5-d]pyrimidin-2(1H)-one

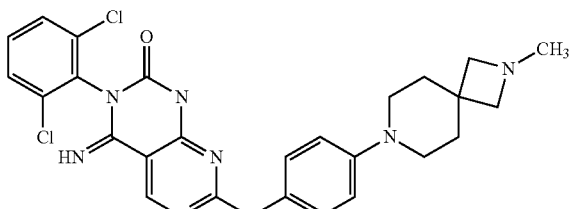

¹H-NMR (400 MHz, CD₃OD) δ: 8.95 (1H, s), 7.60-7.53 (4H, m), 7.51-7.45 (1H, m), 6.99 (2H, d, J=8.3 Hz), 3.19 (4H, s), 3.08-3.05 (4H, m), 2.41 (3H, s), 1.92-1.88 (4H, m)
ESI-MS Found: m/z[M+H] 537

Example 17

7-({4-[4-(1-Acetylazetidin-3-yl)piperazin-1-yl]phenyl}amino)-3-(2,6-dichlorophenyl)-4-imino-1-methyl-3,4-dihydropyrimido[4,5-d]pyrimidin-2(1l)-one

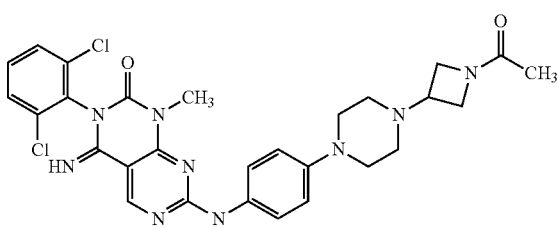 [SMILES: CC(=O)N1CC(N2CCN(c3ccc(Nc4ncc5c(=N)n(-c6c(Cl)cccc6Cl)c(=O)n(C)c5n4)cc3)CC2)C1]

¹H-NMR (400 MHz, CD₃OD) δ: 9.97 (1H, s), 7.61-7.46 (5H, m), 7.00 (2H, d, J=8.8 Hz), 4.29-4.24 (1H, m), 4.15-4.06 (3H, m), 3.93-3.89 (1H, m), 3.61 (3H, s), 3.34 (4H, br), 2.61 (4H, br), 1.91 (3H, s).
ESI-MS Found: m/z[M+H] 595

Example 18

3-(2,6-Dichlorophenyl)-4-imino-7-{[4-(morpholin-4-yl)phenyl]amino}-3,4-dihydropyrimido[4,5-d]pyrimidin-2(1H)-one

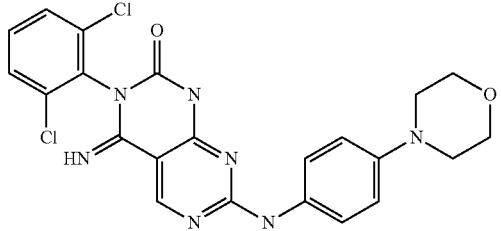 [SMILES: N=c1c2cnc(Nc3ccc(N4CCOCC4)cc3)nc2[nH]c(=O)n1-c1c(Cl)cccc1Cl]

¹H-NMR (400 MHz, DMSO-d6) δ: 11.70 (1H, s), 9.06 (1H, s), 8.82 (1H, s), 7.75-7.62 (2H, br m), 7.60 (2H, d, J=7.8 Hz), 7.46 (1H, t, J=8.0 Hz), 6.89 (2H, d, J=8.8 Hz), 3.73 (4H, t, J=4.9 Hz), 3.05 (4H, t, J=4.6 Hz).
ESI-MS Found: m/z[M+H] 484

Example 19

3-(2,6-Dichlorophenyl)-7-({4-[2-(dimethylamino)-1-methylethoxy]phenyl}amino)-4-imino-3,4-dihydropyrimido[4,5-d]pyrimidin-2(1H)-one

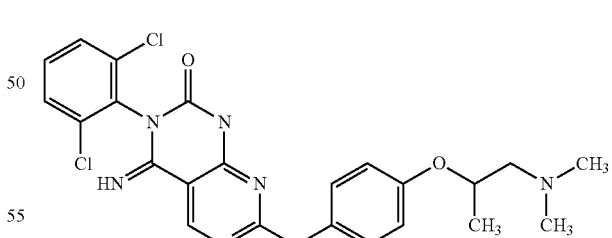

¹H-NMR (400 MHz, CDCl₃) δ: 9.16 (1H, br s), 7.54 (3H, br s), 7.44 (2H, d, J=5.0 Hz), 6.87 (2H, d, J=5.0 Hz), 4.46 (1H, q, J=5.5 Hz), 2.69-2.38 (2H, m), 2.30 (6H, s), 1.28 (3H, d, J=5.5 Hz).
ESI-MS Found: m/z[M+H] 519

Example 20

3-(2,6-Dichlorophenyl)-4-imino-7-({4-[methyl(pyridin-2-ylmethyl)amino]phenyl}amino)-3,4-dihydropyrimido[4,5-d]pyrimidin-2(1H)-one

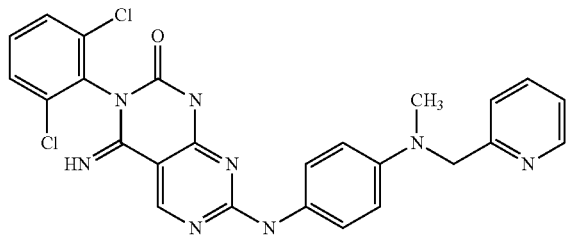 [SMILES: CN(Cc1ccccn1)c1ccc(Nc2ncc3c(=N)n(-c4c(Cl)cccc4Cl)c(=O)[nH]c3n2)cc1]

H-NMR (400 MHz, DMSO-d6) δ: 11.62 (0H, s), 9.01 (1H, s), 8.77 (1H, s), 8.52 (1H, d, J=3.9 Hz), 7.72-7.68 (1H, m), 7.64-7.42 (4H, m), 7.26-7.21 (1H, m), 7.16 (1H, d, J=7.8 Hz), 6.65 (2H, d, J=9.3 Hz), 4.61 (2H, s), 3.08 (3H, s).
ESI-MS Found: m/z[M+H] 519

Example 21

3-(2,6-Dichlorophenyl)-7-({4-[4-(2-hydroxyethyl)piperazin-1-yl]phenyl}amino)-4-imino-3,4-dihydropyrimido[4,5-d]pyrimidin-2(1H)-one

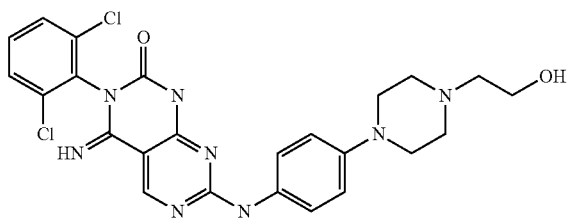 [SMILES: N=c1c2cnc(Nc3ccc(N4CCN(CCO)CC4)cc3)nc2[nH]c(=O)n1-c1c(Cl)cccc1Cl]

$^1$H-NMR (400 MHz, DMSO-d6) δ: 11.68 (1H, s), 9.94 (1H, s), 9.05 (1H, s), 8.81 (1H, s), 7.80-7.54 (4H, m), 7.46 (1H, t, J=8.2 Hz), 6.88 (2H, d, J=9.0 Hz), 4.42 (1H, t, J=5.4 Hz), 3.52 (2H, td, J=6.3, 5.4 Hz), 3.11-3.04 (4H, m), 2.58-2.52 (4H, m), 2.42 (2H, t, J=6.3 Hz).
ESI-MS Found: m/z[M+H] 527

Example 22

3-(2,6-Dichlorophenyl)-7-({4-[2-(dimethylamino)propoxy]phenyl}amino)-4-imino-3,4-dihydropyrimido[4,5-d]pyrimidin-2(1H)-one

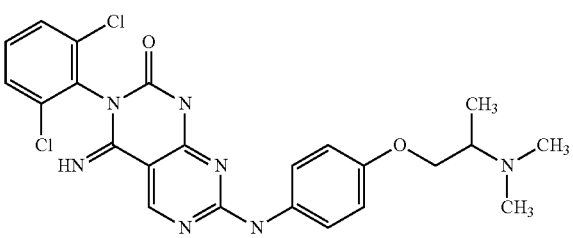 [SMILES: CC(COc1ccc(Nc2ncc3c(=N)n(-c4c(Cl)cccc4Cl)c(=O)[nH]c3n2)cc1)N(C)C]

$^1$H-NMR (400 MHz, CDCl$_3$) δ: 9.16 (1H, br s), 7.46 (3H, br s), 7.40 (2H, d, J=5.0 Hz), 6.86 (2H, d, J=5.0 Hz), 4.03-3.79 (2H, m), 2.94 (1H, q, J=3.8 Hz), 2.34 (6H, s), 1.12 (3H, d, J=3.8 Hz).
ESI-MS Found: m/z[M+H] 500

Example 23

3-(2,6-Dichlorophenyl)-7-[(4-{2-[(dimethylamino)methyl]morpholin-4-yl}phenyl)amino]-4-imino-3,4-dihydropyrimido[4,5-d]pyrimidin-2(1H)-one

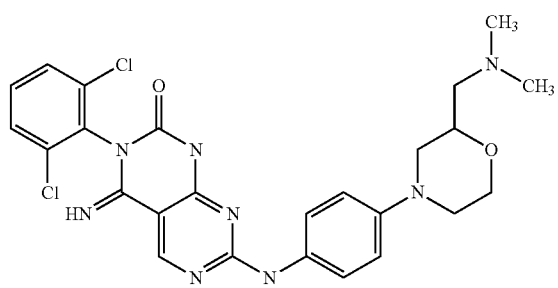 [SMILES: CN(C)CC1CN(c2ccc(Nc3ncc4c(=N)n(-c5c(Cl)cccc5Cl)c(=O)[nH]c4n3)cc2)CCO1]

$^1$H-NMR (400 MHz, CD$_3$OD) δ: 8.95 (1H, s), 7.59-7.40 (5H, m), 6.99 (2H, d, J=8.8 Hz), 4.06-4.03 (1H, m), 3.84-3.78 (2H, m), 3.51-3.42 (2H, m), 3.61 (3H, s), 2.84-2.77 (1H, m), 2.60-2.39 (3H, m), 2.34 (6H, s).
ESI-MS Found: m/z[M+H] 542

Example 24

3-(2,6-Dichlorophenyl)-7-({3-[3-(dimethylamino)propoxy]-4-methoxyphenyl}amino)-4-imino-3,4-dihydropyrimido[4,5-d]pyrimidin-2(1H)-one

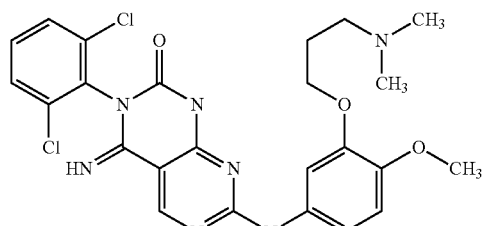

$^1$H-NMR (400 MHz, CDCl$_3$) δ: 9.18 (1H, br s), 7.60-7.05 (5H, m), 6.82 (1H, d, J=5.1 Hz), 4.00-3.82 (2H, m), 3.83 (3H, s), 2.59-2.40 (2H, m), 2.25 (6H, s), 2.05-1.95 (2H, m).
ESI-MS Found: m/z[M+H] 530

Example 25

3-(2,6-Dichlorophenyl)-7-({4-[(dimethylamino)methyl]phenyl}amino)-4-imino-3,4-dihydropyrimido[4,5-d]pyrimidin-2(1H)-one

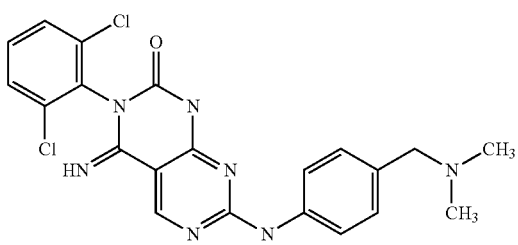 [SMILES: CN(C)Cc1ccc(Nc2ncc3c(=N)n(-c4c(Cl)cccc4Cl)c(=O)[nH]c3n2)cc1]

¹H-NMR (400 MHz, DMSO-d6) δ: 11.79 (1H, s), 10.13 (1H, s), 9.12 (1H, s), 8.90 (1H, s), 7.79-7.75 (2H, m), 7.64-7.58 (2H, m), 7.47 (1H, t, J=8.0 Hz), 7.23-7.19 (2H, m), 3.35 (2H, br s), 2.14 (6H, s).
ESI-MS Found: m/z[M+H] 456

Example 26

3-(2,6-Dichlorophenyl)-7-({4-[3-(dimethylamino)-3-(hydroxymethyl)pyrrolidin-1-yl]phenyl}amino)-4-imino-3,4-dihydropyrimido[4,5-d]pyrimidin-2(1H)-one

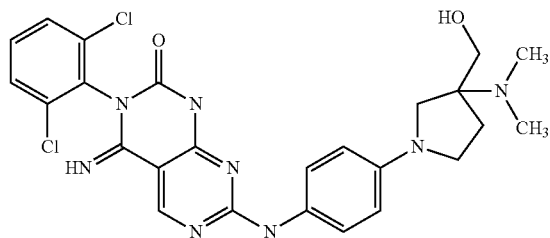 [SMILES: CN(C)C1(CO)CCN(c2ccc(Nc3ncc4c(=N)n(-c5c(Cl)cccc5Cl)c(=O)[nH]c4n3)cc2)C1]

¹H-NMR (400 MHz, CD₃OD) δ: 8.92 (1H, s), 7.58 (2H, d, J=8.0 Hz), 7.50-7.45 (3H, m), 6.58 (2H, d, J=8.0 Hz), 3.75 (1H, d, J=10.2 Hz), 3.66 (1H, d, J=10.2 Hz), 3.42-3.24 (4H, m), 2.45 (6H, s), 1.52-1.48 (1H, m), 1.40-1.36 (1H, m)
ESI-MS Found: m/z[M+H] 541

Example 27

3-(2,6-Dichlorophenyl)-7-[(4-{1-[2-(dimethylamino)ethyl]-1H-pyrazol-4-yl}phenyl)amino]-4-imino-3,4-dihydropyrimido[4,5-d]pyrimidin-2(1H)-one

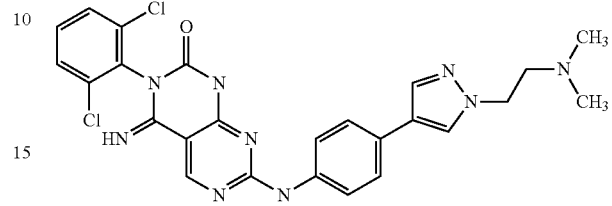

¹H-NMR (400 MHz, CD₃OD) δ: 8.96 (1H, br s), 7.80 (1H, s), 7.74 (1H, s), 7.69 (2H, d, J=8.8 Hz), 7.56-7.52 (2H, m), 7.47-7.45 (3H, m), 4.26 (2H, t, J=4.0 Hz), 2.83 (2H, t, J=4.0 Hz), 2.28 (6H, s).
ESI-MS Found: m/z[M+H] 537

Example 28

3-(2,6-Dichlorophenyl)-1-(2-hydroxyethyl)-4-imino-7-{[4-(4-methylpiperazin-1-yl)phenyl]amino}-3,4-dihydropyrimido[4,5-d]pyrimidin-2(1H)-one

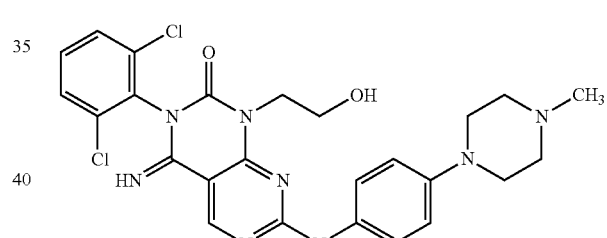

¹H-NMR (400 MHz, CD₃OD) δ: 8.98 (1H, br s), 7.61-7.56 (4H, m), 7.00 (1H, d, J=8.8 Hz), 4.41 (2H, t, J=5.4 Hz), 3.87 (2H, t, J=5.4 Hz), 3.23 (4H, br), 2.67 (4H, br), 2.39 (3H, s).
ESI-MS Found: m/z[M+H] 542

| Example No | Structure |
|---|---|
| 1a | 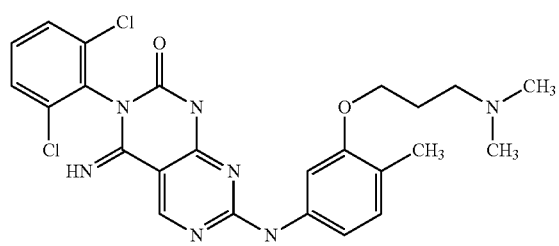 [SMILES: Cc1ccc(Nc2ncc3c(=N)n(-c4c(Cl)cccc4Cl)c(=O)[nH]c3n2)cc1OCCCN(C)C] |

-continued
| Example No | Structure |
|---|---|
| 2a | 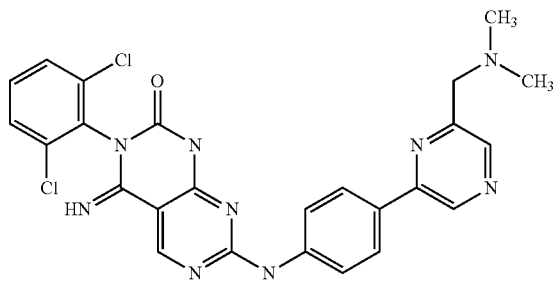 [SMILES: CN(C)Cc1cncc(-c2ccc(Nc3ncc4c(=N)n(-c5c(Cl)cccc5Cl)c(=O)[nH]c4n3)cc2)n1] |
| 3a | 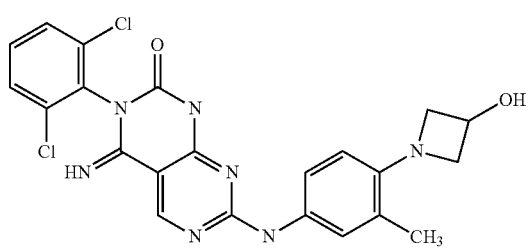 [SMILES: Cc1cc(Nc2ncc3c(=N)n(-c4c(Cl)cccc4Cl)c(=O)[nH]c3n2)ccc1N1CC(O)C1] |
| 4a | 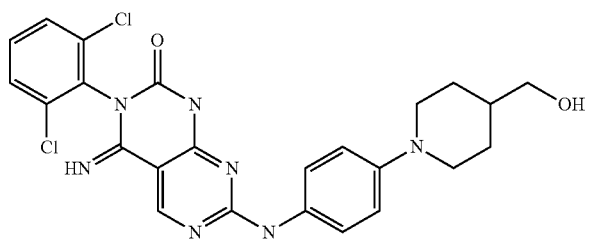 [SMILES: N=c1c2cnc(Nc3ccc(N4CCC(CO)CC4)cc3)nc2[nH]c(=O)n1-c1c(Cl)cccc1Cl] |
| 5a | 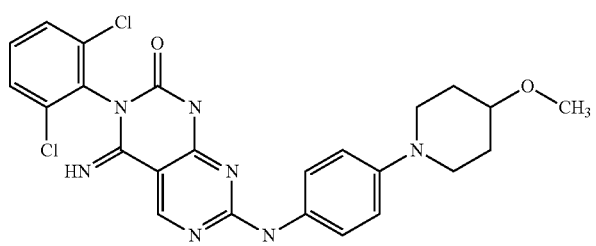 [SMILES: COC1CCN(c2ccc(Nc3ncc4c(=N)n(-c5c(Cl)cccc5Cl)c(=O)[nH]c4n3)cc2)CC1] |
| 6a | 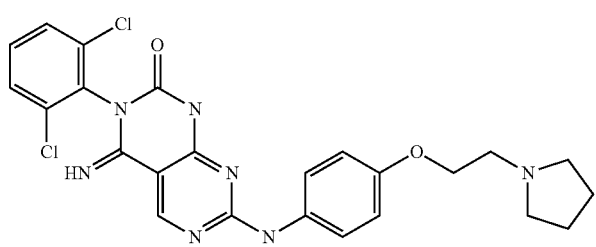 [SMILES: N=c1c2cnc(Nc3ccc(OCCN4CCCC4)cc3)nc2[nH]c(=O)n1-c1c(Cl)cccc1Cl] |
| 7a | 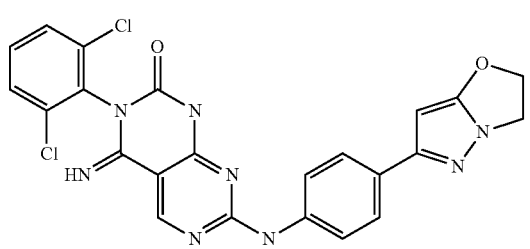 [SMILES: N=c1c2cnc(Nc3ccc(-c4cc5n(n4)CCO5)cc3)nc2[nH]c(=O)n1-c1c(Cl)cccc1Cl] |

| Example No | Structure |
|---|---|
| 8a | 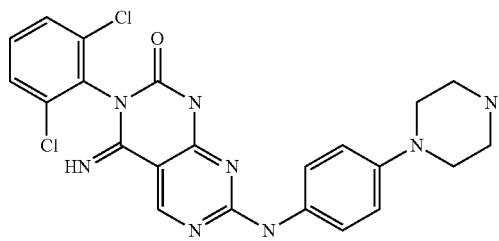 [SMILES: N=c1c2cnc(Nc3ccc(N4CCNCC4)cc3)nc2[nH]c(=O)n1-c1c(Cl)cccc1Cl] |
| 9a | 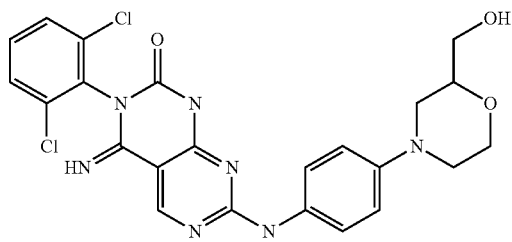 [SMILES: N=c1c2cnc(Nc3ccc(N4CCOC(CO)C4)cc3)nc2[nH]c(=O)n1-c1c(Cl)cccc1Cl] |
| 10a | 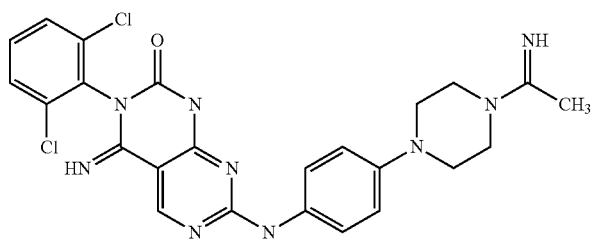 [SMILES: CC(=N)N1CCN(c2ccc(Nc3ncc4c(=N)n(-c5c(Cl)cccc5Cl)c(=O)[nH]c4n3)cc2)CC1] |
| 11a | 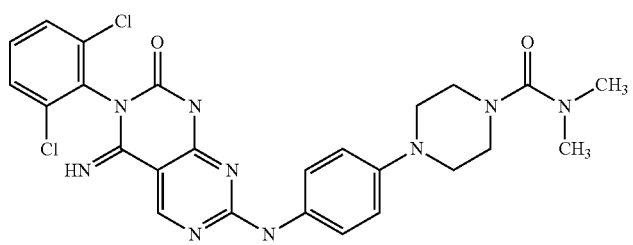 [SMILES: CN(C)C(=O)N1CCN(c2ccc(Nc3ncc4c(=N)n(-c5c(Cl)cccc5Cl)c(=O)[nH]c4n3)cc2)CC1] |
| 12a | 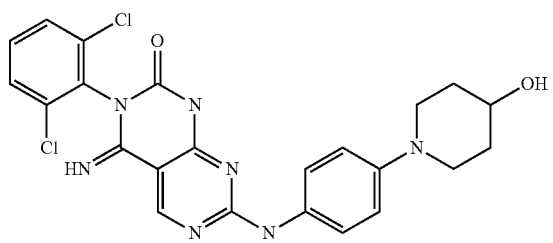 [SMILES: N=c1c2cnc(Nc3ccc(N4CCC(O)CC4)cc3)nc2[nH]c(=O)n1-c1c(Cl)cccc1Cl] |
| 13a | 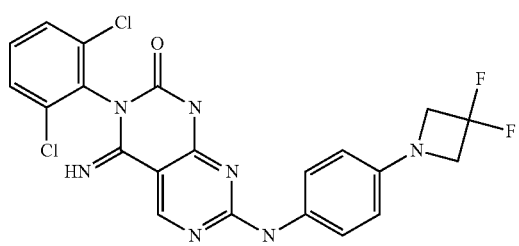 [SMILES: N=c1c2cnc(Nc3ccc(N4CC(F)(F)C4)cc3)nc2[nH]c(=O)n1-c1c(Cl)cccc1Cl] |

-continued
| Example No | Structure |
|---|---|
| 14a | 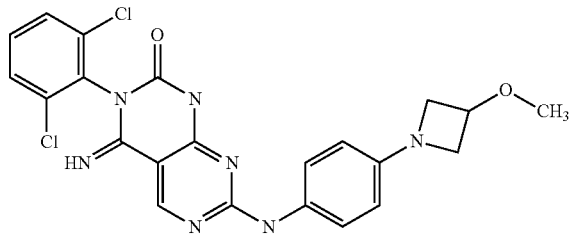 [SMILES: COC1CN(c2ccc(Nc3ncc4c(=N)n(-c5c(Cl)cccc5Cl)c(=O)[nH]c4n3)cc2)C1] |
| 15a | 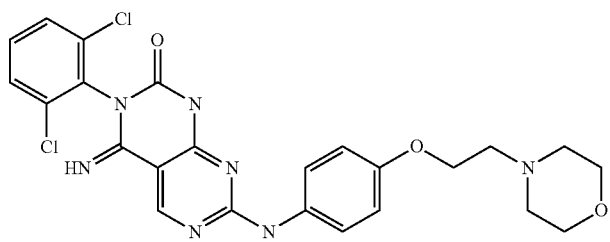 [SMILES: N=c1c2cnc(Nc3ccc(OCCN4CCOCC4)cc3)nc2[nH]c(=O)n1-c1c(Cl)cccc1Cl] |
| 16a | 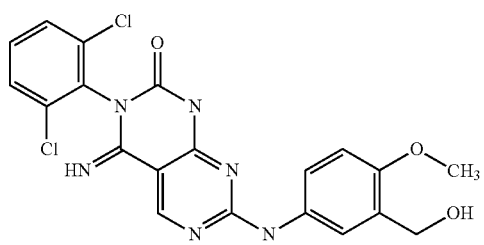 [SMILES: COc1ccc(Nc2ncc3c(=N)n(-c4c(Cl)cccc4Cl)c(=O)[nH]c3n2)cc1CO] |
| 17a | 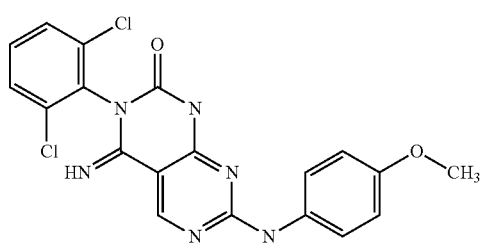 [SMILES: COc1ccc(Nc2ncc3c(=N)n(-c4c(Cl)cccc4Cl)c(=O)[nH]c3n2)cc1] |
| 18a | 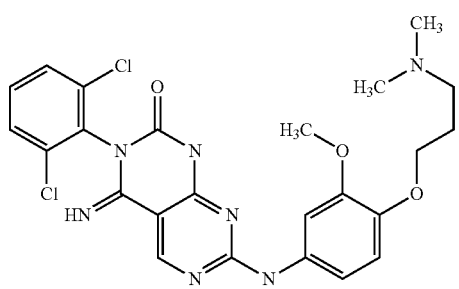 [SMILES: COc1cc(Nc2ncc3c(=N)n(-c4c(Cl)cccc4Cl)c(=O)[nH]c3n2)ccc1OCCCN(C)C] |
| 19a | 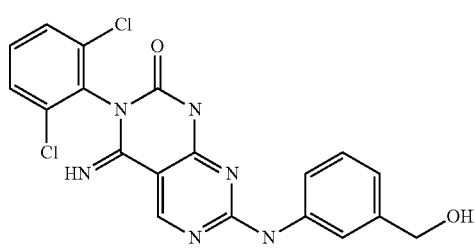 [SMILES: N=c1c2cnc(Nc3cccc(CO)c3)nc2[nH]c(=O)n1-c1c(Cl)cccc1Cl] |

| Example No | Structure |
|---|---|
| 20a | 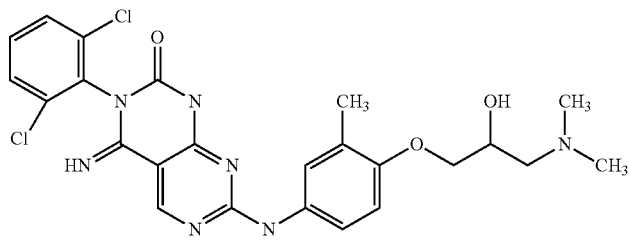 [SMILES: Cc1cc(Nc2ncc3c(=N)n(-c4c(Cl)cccc4Cl)c(=O)[nH]c3n2)ccc1OCC(O)CN(C)C] |
| 21a | 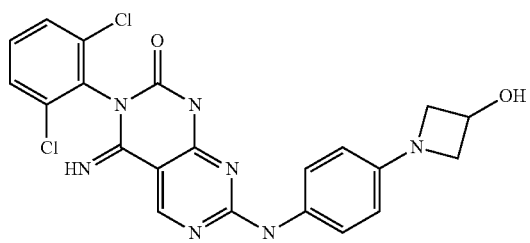 [SMILES: N=c1c2cnc(Nc3ccc(N4CC(O)C4)cc3)nc2[nH]c(=O)n1-c1c(Cl)cccc1Cl] |
| 22a | 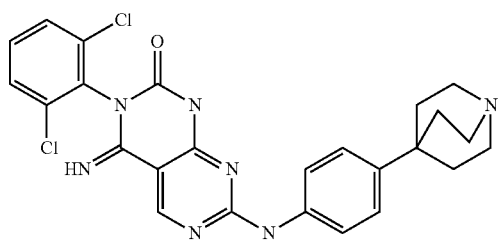 [SMILES: N=c1c2cnc(Nc3ccc(C45CCN(CC4)CC5)cc3)nc2[nH]c(=O)n1-c1c(Cl)cccc1Cl] |
| 23a | 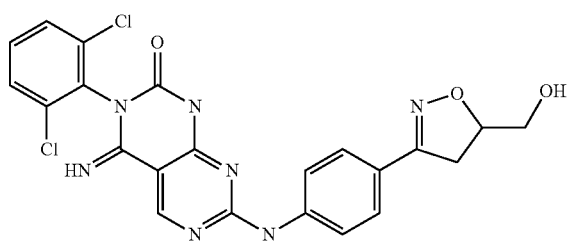 [SMILES: N=c1c2cnc(Nc3ccc(C4=NOC(CO)C4)cc3)nc2[nH]c(=O)n1-c1c(Cl)cccc1Cl] |
| 24a | 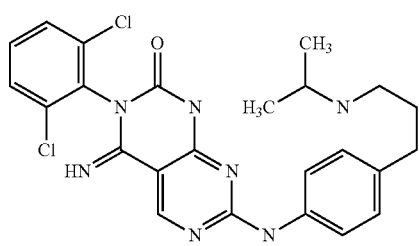 [SMILES: CC(C)NCCCc1ccc(Nc2ncc3c(=N)n(-c4c(Cl)cccc4Cl)c(=O)[nH]c3n2)cc1] |
| 25a | 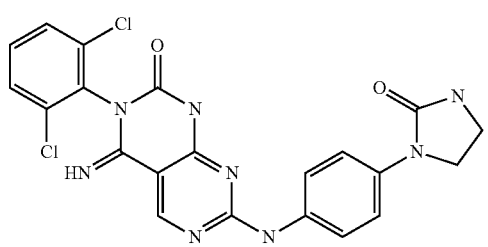 [SMILES: N=c1c2cnc(Nc3ccc(N4CCNC4=O)cc3)nc2[nH]c(=O)n1-c1c(Cl)cccc1Cl] |

-continued
| Example No | Structure |
|---|---|
| 26a | 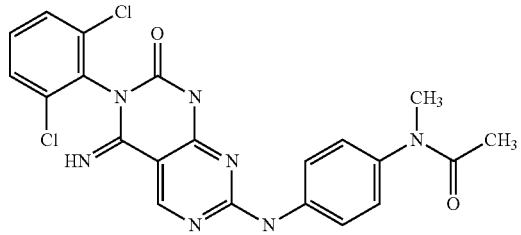 [SMILES: CC(=O)N(C)c1ccc(Nc2ncc3c(=N)n(-c4c(Cl)cccc4Cl)c(=O)[nH]c3n2)cc1] |
| 27a | 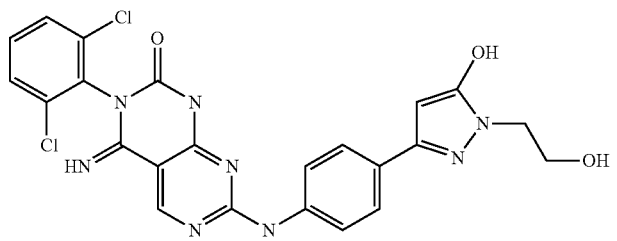<br>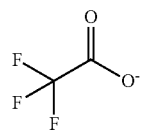 |
| 28a | 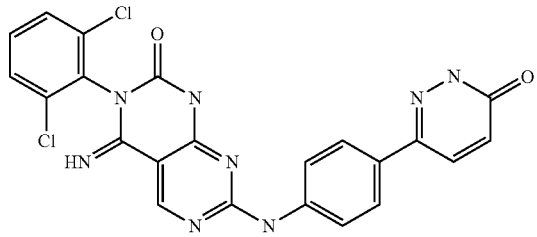 [SMILES: N=c1c2cnc(Nc3ccc(-c4ccc(=O)[nH]n4)cc3)nc2[nH]c(=O)n1-c1c(Cl)cccc1Cl] |
| 29a | 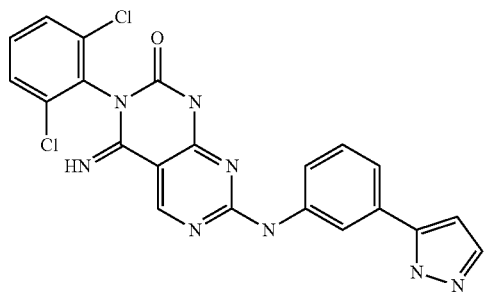 [SMILES: N=c1c2cnc(Nc3cccc(-c4ccn[nH]4)c3)nc2[nH]c(=O)n1-c1c(Cl)cccc1Cl] |
| 30a | 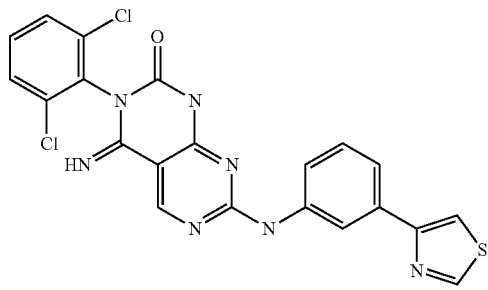 [SMILES: N=c1c2cnc(Nc3cccc(-c4cscn4)c3)nc2[nH]c(=O)n1-c1c(Cl)cccc1Cl] |

| Example No | Structure |
|---|---|
| 31a | 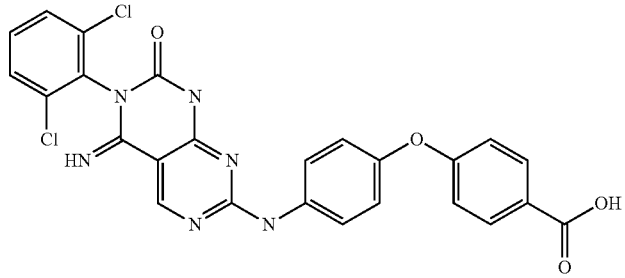 [SMILES: N=c1c2cnc(Nc3ccc(Oc4ccc(C(=O)O)cc4)cc3)nc2[nH]c(=O)n1-c1c(Cl)cccc1Cl] |
| 32a | 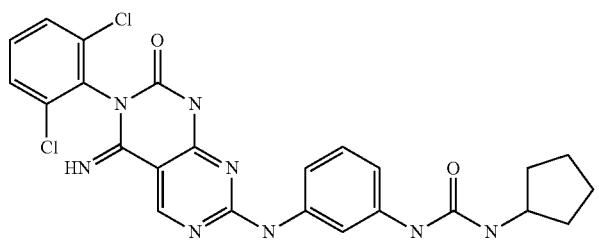 [SMILES: N=c1c2cnc(Nc3cccc(NC(=O)NC4CCCC4)c3)nc2[nH]c(=O)n1-c1c(Cl)cccc1Cl] |
| 33a | 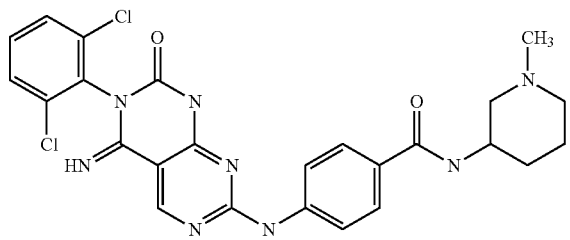 [SMILES: CN1CCCC(NC(=O)c2ccc(Nc3ncc4c(=N)n(-c5c(Cl)cccc5Cl)c(=O)[nH]c4n3)cc2)C1] |
| 34a | 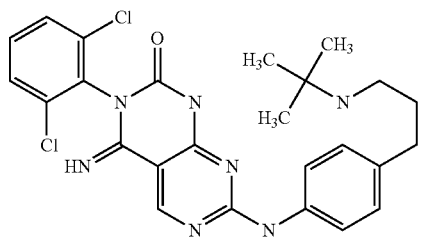 [SMILES: CC(C)(C)NCCCc1ccc(Nc2ncc3c(=N)n(-c4c(Cl)cccc4Cl)c(=O)[nH]c3n2)cc1] |
| 35a | 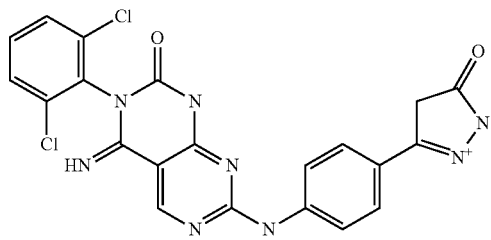<br>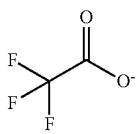 |

| Example No | Structure |
|---|---|
| 36a | 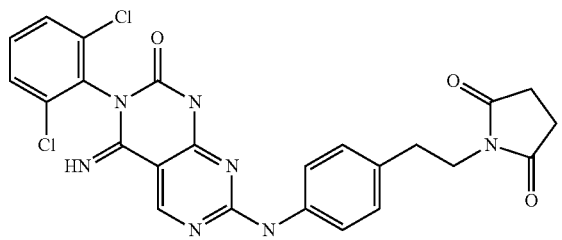 [SMILES: N=c1c2cnc(Nc3ccc(CCN4C(=O)CCC4=O)cc3)nc2[nH]c(=O)n1-c1c(Cl)cccc1Cl] |
| 37a | 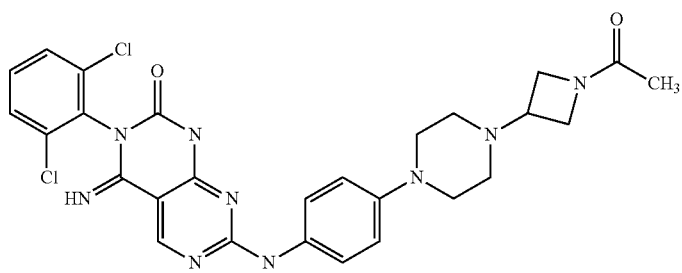 [SMILES: CC(=O)N1CC(N2CCN(c3ccc(Nc4ncc5c(=N)n(-c6c(Cl)cccc6Cl)c(=O)[nH]c5n4)cc3)CC2)C1] |
| 38a | 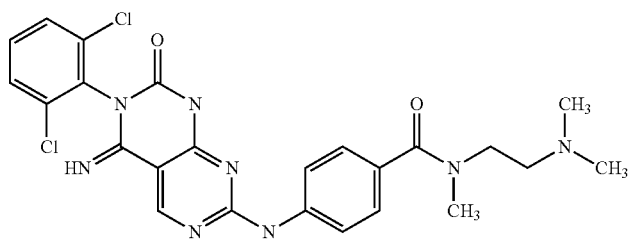 [SMILES: CN(C)CCN(C)C(=O)c1ccc(Nc2ncc3c(=N)n(-c4c(Cl)cccc4Cl)c(=O)[nH]c3n2)cc1] |
| 39a | 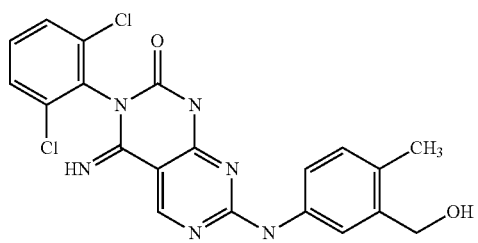 [SMILES: Cc1ccc(Nc2ncc3c(=N)n(-c4c(Cl)cccc4Cl)c(=O)[nH]c3n2)cc1CO] |
| 40a | 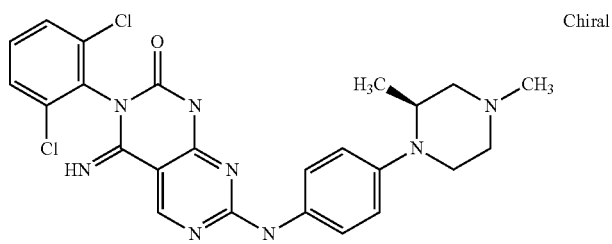 [SMILES: C[C@H]1CN(C)CCN1c1ccc(Nc2ncc3c(=N)n(-c4c(Cl)cccc4Cl)c(=O)[nH]c3n2)cc1 ; "Chiral"] Chiral |
| 41a | 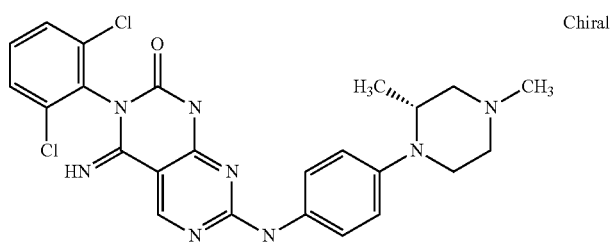 [SMILES: C[C@@H]1CN(C)CCN1c1ccc(Nc2ncc3c(=N)n(-c4c(Cl)cccc4Cl)c(=O)[nH]c3n2)cc1 ; "Chiral"] Chiral |

-continued
| Example No | Structure |
|---|---|
| 42a | 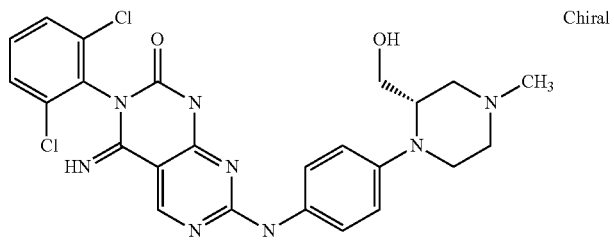 [SMILES: CN1CCN(c2ccc(Nc3ncc4c(=N)n(-c5c(Cl)cccc5Cl)c(=O)[nH]c4n3)cc2)[C@H](CO)C1 ; "Chiral"] Chiral |
| 43a | 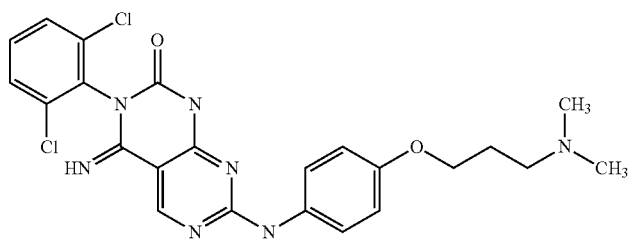 [SMILES: CN(C)CCCOc1ccc(Nc2ncc3c(=N)n(-c4c(Cl)cccc4Cl)c(=O)[nH]c3n2)cc1] |
| 44a | 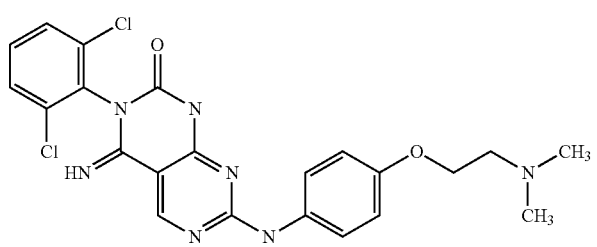 [SMILES: CN(C)CCOc1ccc(Nc2ncc3c(=N)n(-c4c(Cl)cccc4Cl)c(=O)[nH]c3n2)cc1] |
| 45a | 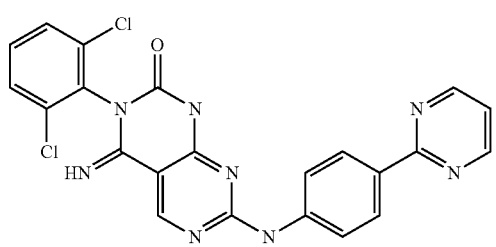 [SMILES: N=c1c2cnc(Nc3ccc(-c4ncccn4)cc3)nc2[nH]c(=O)n1-c1c(Cl)cccc1Cl] |
| 46a | 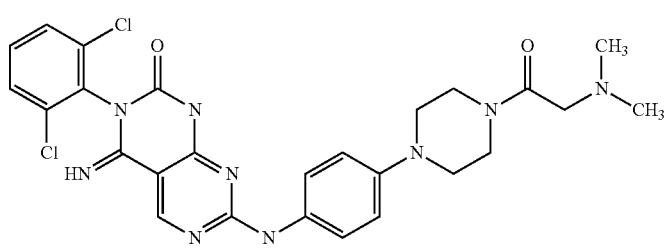 [SMILES: CN(C)CC(=O)N1CCN(c2ccc(Nc3ncc4c(=N)n(-c5c(Cl)cccc5Cl)c(=O)[nH]c4n3)cc2)CC1] |
| 47a | 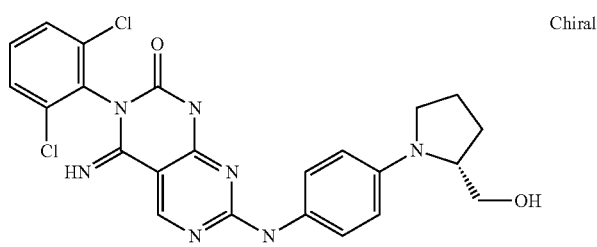 [SMILES: N=c1c2cnc(Nc3ccc(N4CCC[C@@H]4CO)cc3)nc2[nH]c(=O)n1-c1c(Cl)cccc1Cl ; "Chiral"] Chiral |

| Example No | Structure |
|---|---|
| 48a | 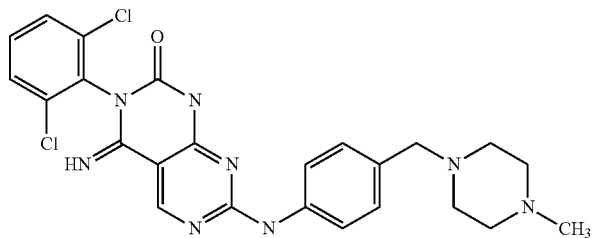 [SMILES: CN1CCN(Cc2ccc(Nc3ncc4c(=N)n(-c5c(Cl)cccc5Cl)c(=O)[nH]c4n3)cc2)CC1] |
| 49a | 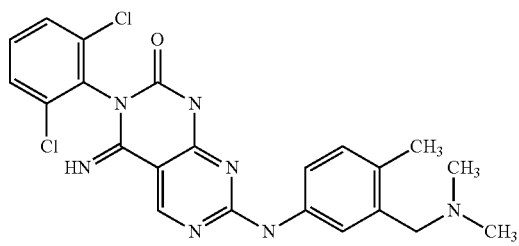 [SMILES: Cc1ccc(Nc2ncc3c(=N)n(-c4c(Cl)cccc4Cl)c(=O)[nH]c3n2)cc1CN(C)C] |
| 50a | 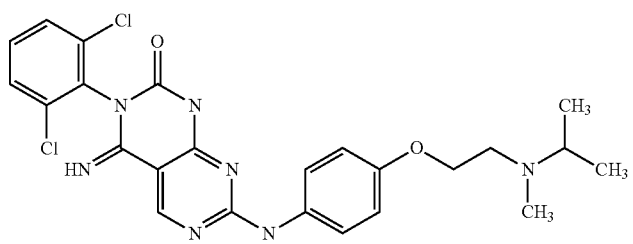 [SMILES: CC(C)N(C)CCOc1ccc(Nc2ncc3c(=N)n(-c4c(Cl)cccc4Cl)c(=O)[nH]c3n2)cc1] |
| 51a | 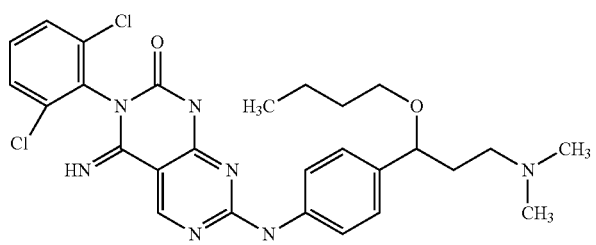 [SMILES: CCCCOC(CCN(C)C)c1ccc(Nc2ncc3c(=N)n(-c4c(Cl)cccc4Cl)c(=O)[nH]c3n2)cc1] |
| 52a | 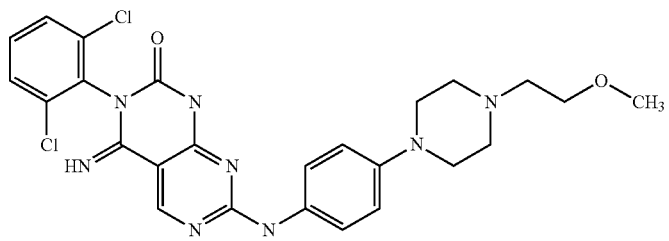 [SMILES: COCCN1CCN(c2ccc(Nc3ncc4c(=N)n(-c5c(Cl)cccc5Cl)c(=O)[nH]c4n3)cc2)CC1] |
| 53a | 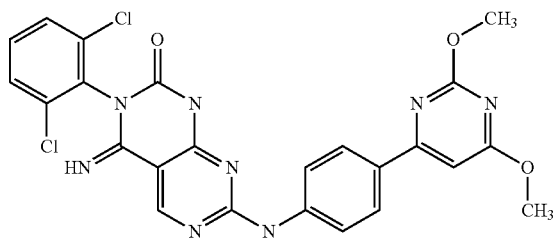 [SMILES: COc1cc(-c2ccc(Nc3ncc4c(=N)n(-c5c(Cl)cccc5Cl)c(=O)[nH]c4n3)cc2)nc(OC)n1] |

| Example No | Structure |
|---|---|
| 54a | 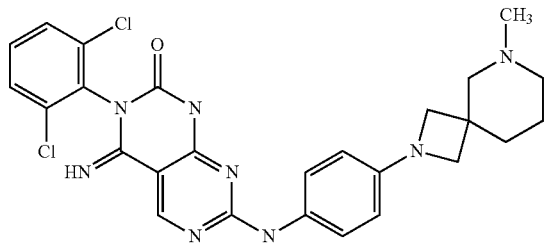 [SMILES: CN1CCCC2(C1)CN(c1ccc(Nc3ncc4c(=N)n(-c5c(Cl)cccc5Cl)c(=O)[nH]c4n3)cc1)C2] |
| 55a | 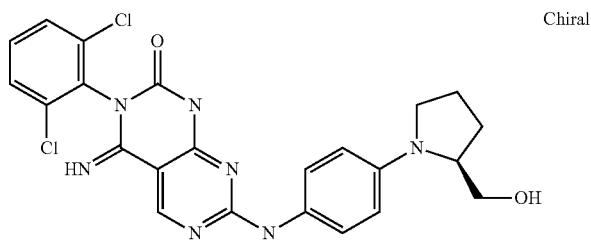 [SMILES: "Chiral" ; N=c1c2cnc(Nc3ccc(N4CCC[C@H]4CO)cc3)nc2[nH]c(=O)n1-c1c(Cl)cccc1Cl] Chiral |
| 56a | 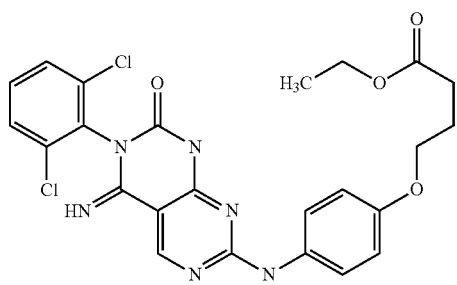 [SMILES: CCOC(=O)CCCOc1ccc(Nc2ncc3c(=N)n(-c4c(Cl)cccc4Cl)c(=O)[nH]c3n2)cc1] |
| 57a | 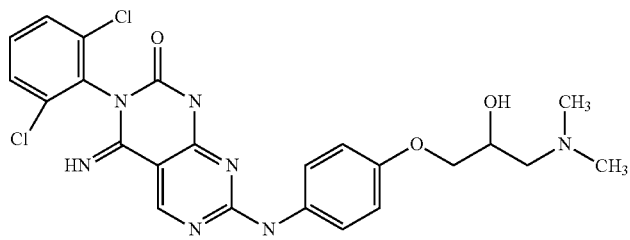 [SMILES: CN(C)CC(O)COc1ccc(Nc2ncc3c(=N)n(-c4c(Cl)cccc4Cl)c(=O)[nH]c3n2)cc1] |
| 58a | 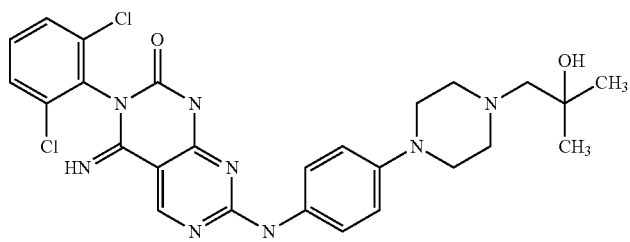 [SMILES: CC(C)(O)CN1CCN(c2ccc(Nc3ncc4c(=N)n(-c5c(Cl)cccc5Cl)c(=O)[nH]c4n3)cc2)CC1] |

| Example No | Structure |
|---|---|
| 59a | 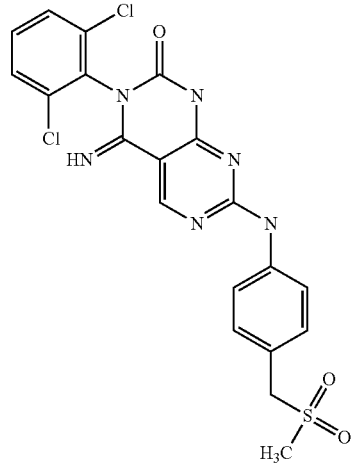 [SMILES: CS(=O)(=O)Cc1ccc(Nc2ncc3c(=N)n(-c4c(Cl)cccc4Cl)c(=O)[nH]c3n2)cc1] |
| 60a | 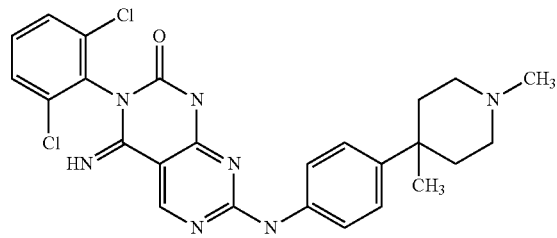 [SMILES: CN1CCC(C)(c2ccc(Nc3ncc4c(=N)n(-c5c(Cl)cccc5Cl)c(=O)[nH]c4n3)cc2)CC1] |
| 61a | 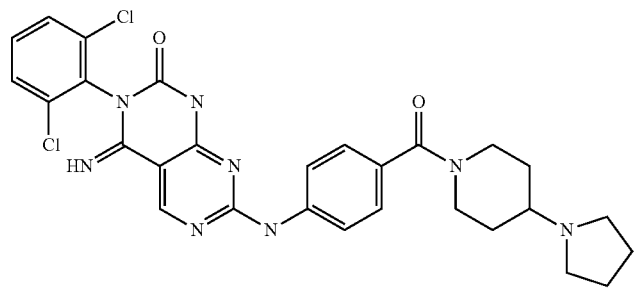 [SMILES: N=c1c2cnc(Nc3ccc(C(=O)N4CCC(N5CCCC5)CC4)cc3)nc2[nH]c(=O)n1-c1c(Cl)cccc1Cl] |
| 62a | 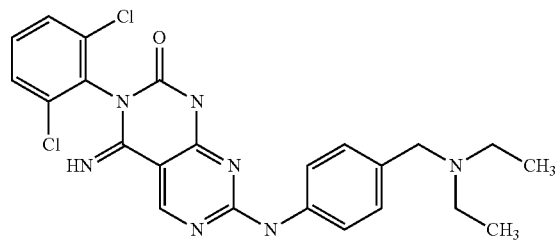 [SMILES: CCN(CC)Cc1ccc(Nc2ncc3c(=N)n(-c4c(Cl)cccc4Cl)c(=O)[nH]c3n2)cc1] |
| 63a | 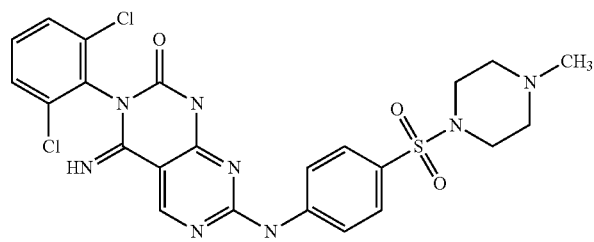 [SMILES: CN1CCN(S(=O)(=O)c2ccc(Nc3ncc4c(=N)n(-c5c(Cl)cccc5Cl)c(=O)[nH]c4n3)cc2)CC1] |

-continued
| Example No | Structure |
|---|---|
| 64a | 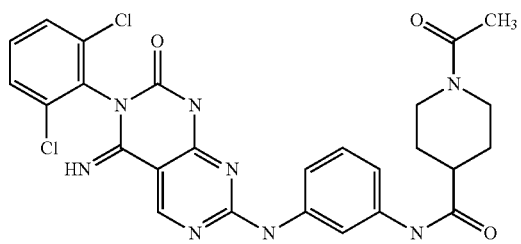 [SMILES: CC(=O)N1CCC(C(=O)Nc2cccc(Nc3ncc4c(=N)n(-c5c(Cl)cccc5Cl)c(=O)[nH]c4n3)c2)CC1] |
| 65a | 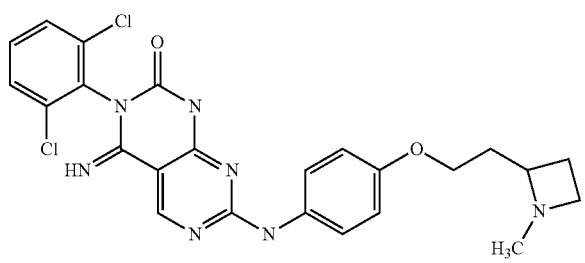 [SMILES: CN1CCC1CCOc1ccc(Nc2ncc3c(=N)n(-c4c(Cl)cccc4Cl)c(=O)[nH]c3n2)cc1] |
| 66a | 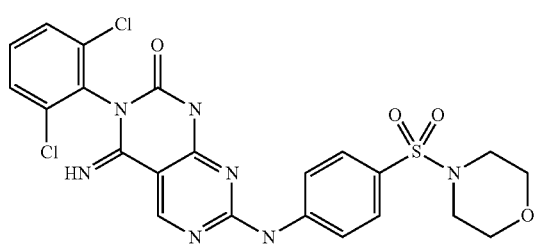 [SMILES: N=c1c2cnc(Nc3ccc(S(=O)(=O)N4CCOCC4)cc3)nc2[nH]c(=O)n1-c1c(Cl)cccc1Cl] |
| 67a | 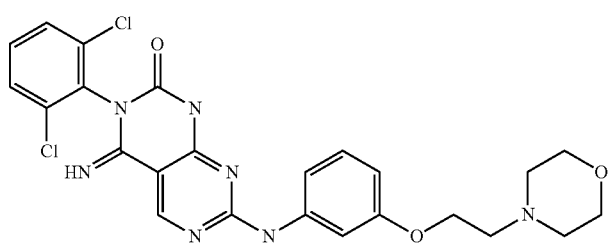 [SMILES: N=c1c2cnc(Nc3cccc(OCCN4CCOCC4)c3)nc2[nH]c(=O)n1-c1c(Cl)cccc1Cl] |
| 68a | 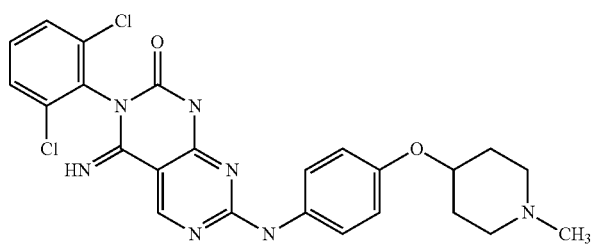 [SMILES: CN1CCC(Oc2ccc(Nc3ncc4c(=N)n(-c5c(Cl)cccc5Cl)c(=O)[nH]c4n3)cc2)CC1] |
| 69a | 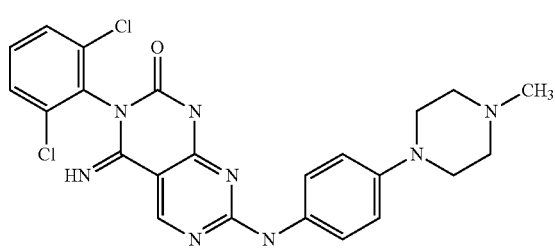 [SMILES: CN1CCN(c2ccc(Nc3ncc4c(=N)n(-c5c(Cl)cccc5Cl)c(=O)[nH]c4n3)cc2)CC1] |

-continued
| Example No | Structure |
|---|---|
| 70a | 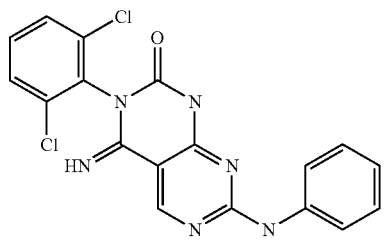 [SMILES: N=c1c2cnc(Nc3ccccc3)nc2[nH]c(=O)n1-c1c(Cl)cccc1Cl] |
| 71a | 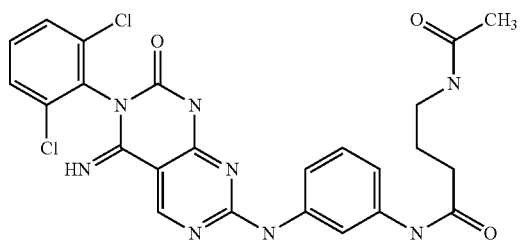 [SMILES: CC(=O)NCCCC(=O)Nc1cccc(Nc2ncc3c(=N)n(-c4c(Cl)cccc4Cl)c(=O)[nH]c3n2)c1] |
| 72a | 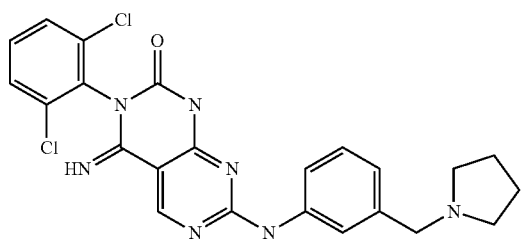 [SMILES: N=c1c2cnc(Nc3cccc(CN4CCCC4)c3)nc2[nH]c(=O)n1-c1c(Cl)cccc1Cl] |
| 73a | 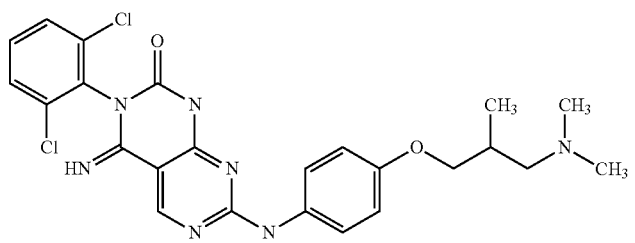 [SMILES: CC(COc1ccc(Nc2ncc3c(=N)n(-c4c(Cl)cccc4Cl)c(=O)[nH]c3n2)cc1)CN(C)C] |
| 74a | 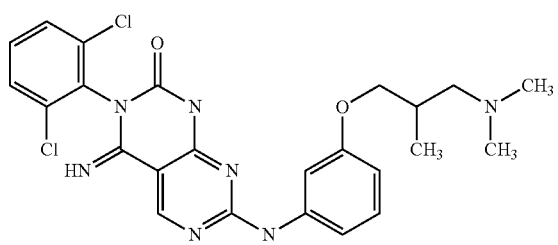 [SMILES: CC(COc1cccc(Nc2ncc3c(=N)n(-c4c(Cl)cccc4Cl)c(=O)[nH]c3n2)c1)CN(C)C] |
| 75a | 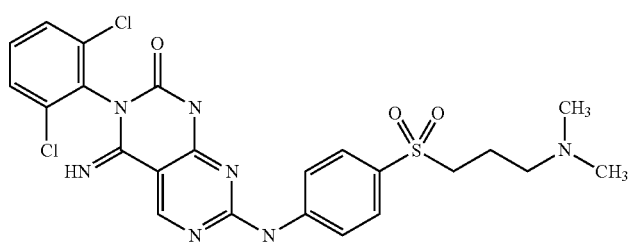 [SMILES: CN(C)CCCS(=O)(=O)c1ccc(Nc2ncc3c(=N)n(-c4c(Cl)cccc4Cl)c(=O)[nH]c3n2)cc1] |

-continued

| Example No | Structure |
|---|---|
| 76a | (structure) |
| 77a | (structure) |
| 78a | (structure) |
| 79a | (structure) |
| 80a | (structure) |
| 81a | (structure) |

-continued

| Example No | Structure |
|---|---|
| 82a | 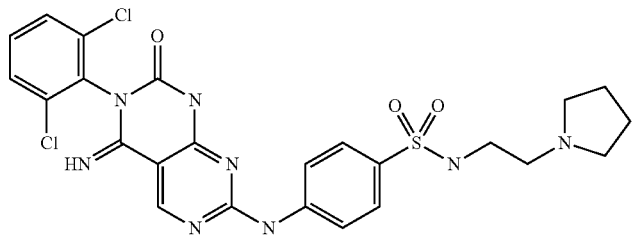 [SMILES: N=c1c2cnc(Nc3ccc(S(=O)(=O)NCCN4CCCC4)cc3)nc2[nH]c(=O)n1-c1c(Cl)cccc1Cl] |

Tables below represent ¹H-NMR data and MS data of the foregoing compounds.

| Example No | ¹H NMR (400 MHz) | MS |
|---|---|---|
| 1a | (CDCl3) δ: 9.10 (1H, brs), 7.58-7.40 (5H, m), 7.05 (1H, d, J = 5.0 Hz), 2.57-2.43 (2H, m), 2.32 (6H, s), 2.30-2.23 (2H, m), 2.17 (3H, s), 2.05-1.92 (2H, m). | 514 |
| 2a | (DMSO) δ: 11.9 (1H, brs), 10.4 (1H, brs), 9.18 (1H, s), 9.14 (1H, d, J = 2.0 Hz), 8.98 (1H, s), 8.66 (1H, d, J = 2.0 Hz), 8.10-8.02 (4H, m), 7.63-7.61 (2H, m), 7.50-7.48 (1H, m), 3.60 (2H, s), 2.19 (6H, s) | 534 |
| 3a | (DMSO) δ: 8.93 (1H, brs), 7.53-7.35 (5H, m), 6.93 (1H, d, J = 8.8 Hz), 4.80-4.76 (1H, m), 4.44-4.35 (2H, m), 3.75-3.70 (2H, m), 1.00 (3H, s). | 485 |
| 4a | (DMSO) δ: 9.04 (1H, brs), 7.59-7.46 (5H, m), 6.87 (2H, d, J = 8.8 Hz), 3.63-3.60 (2H, m), 3.32-3.26 (2H, m), 2.60-2.54 (2H, m), 1.75-1.71 (2H, m), 1.47 (1H, br), 1.27-1.21 (2H, m). | 513 |
| 5a | (CD3OD) δ: 8.93 (1H, brs), 7.53-7.35 (5H, m), 6.93 (2H, d, J = 8.8 Hz), 3.58-3.42 (2H, m), 3.43 (3H, s), 3.34-3.30 (1H, m), 2.91-2.85 (2H, m), 2.02-2.00 (2H, m), 1.73-1.65 (2H, m). | 513 |
| 6a | (CDCl3) δ: 9.15 (1H, brs), 7.60-7.40 (3H, m), 7.45 (2H, d, J = 5.5 Hz), 6.86 (2H, d, J = 5.5 Hz), 4.08 (2H, t, J = 5.2 Hz), 2.89 (2H, t, J = 5.2 Hz), 2.67-2.59 (2H, m), 1.83-1.78 (4H, m). | 512 |
| 7a | (DMSO-d6) δ: 11.83 (1H, brs), 10.22 (1H, brs), 9.14 (1H, s), 8.92 (1H, s), 7.87-7.83 (2H, m), 7.67-7.60 (4H, m), 7.47 (1H, t, J = 8.0 Hz), 5.88 (1H, s), 5.06 (2H, t, J = 7.9 Hz), 4.28 (2H, t, J = 7.9 Hz). | 507 |
| 8a | (CD3OD) δ: 8.91 (1H, brs), 7.54-7.40 (5H, m), 6.93 (2H, d, J = 8.8 Hz), 3.12 (4H, br), 3.01 (4H, br). | 484 |
| 9a | (CD3OD) δ: 8.93 (1H, brs), 7.53-7.34 (5H, m), 6.92 (2H, d, J = 8.8 Hz), 4.10-4.00 (1H, m), 3.83-3.58 (4H, m), 3.50-3.47 (1H, m), 3.40-3.37 (1H, m), 2.84-2.77 (1H, m), 2.59-2.54 (1H, m). | 515 |
| 10a | (CD3OD) δ: 8.83 (1H, brs), 7.63-7.57 (2H, m), 7.51 (2H, d, J = 8.8 Hz), 7.40 (1H, t, J = 7.6 Hz), 6.95 (2H, d, J = 8.8 Hz), 3.75-3.63 (4H, m), 3.16-3.08 (4H, m), 2.14 (3H, s). | 525 |
| 11a | (CD3OD) δ: 8.93 (1H, brs), 7.60-7.45 (5H, m), 6.93 (2H, d, J = 8.8 Hz), 3.38 (4H, br), 3.13 (4H, br), 2.86 (3H, s). | 555 |
| 12a | (CD3OD) δ: 8.93 (1H, brs), 7.52-7.34 (5H, m), 6.92 (2H, d, J = 8.8 Hz), 3.75 (1H, br), 3.51-3.48 (2H, m), 2.87-2.81 (2H, m), 1.98-1.96 (2H, m), 1.68-1.66 (2H, m). | 499 |
| 13a | (DMSO) δ: 9.05 (1H, s), 7.60-7.40 (5H, br), 6.52 (2H, d, J = 8.4 Hz), 6.98 (1H, d, J = 8.0 Hz), 4.22 (4H, m). | 491 |
| 14a | (CD3OD) δ: 8.93 (1H, brs), 7.54-7.40 (5H, m), 6.49 (2H, d, J = 8.8 Hz), 4.36-4.32 (1H, m), 4.11-4.07 (2H, m), 3.69-3.66 (2H, m), 3.33 (3H, s). | 485 |
| 15a | (DMSO-d6) δ: 11.73 (1H, s), 10.06-9.92 (1H, m), 9.07 (1H, s), 8.84 (1H, s), 7.75-7.65 (2H, m), 7.62-7.59 (2H, m), 7.46 (1H, dd, J = 8.8, 7.3 Hz), 6.91-6.87 (2H, m), 4.06 (2H, t, J = 5.9 Hz), 3.59-3.55 (4H, m), 2.67 (2H, t, J = 5.9 Hz), 2.48-2.44 (4H, m). | 528 |
| 16a | (DMSO-d6) δ: 11.66 (1H, brs), 9.95 (1H, brs), 9.07 (1H, s), 8.83 (1H, s), 7.76-7.57 (4H, m), 7.46 (1H, t, J = 8.0 Hz), 6.87 (1H, d, J = 9.0 Hz), 4.99-4.88 (1H, brm), 4.48 (2H, d, J = 5.4 Hz), 3.75 (3H, s). | 459 |
| 17a | (DMSO-d6) δ: 11.72 (1H, s), 9.99 (1H, s), 9.08 (1H, s), 8.84 (1H, s), 7.75-7.58 (4H, m), 7.46 (1H, dd, J = 8.8, 7.6 Hz), 6.88 (2H, d, J = 9.3 Hz), 3.73 (3H, s). | 429 |
| 18a | (CDCl3) δ: 9.20 (1H, brs), 7.69-7.28 (5H, m), 6.84 (1H, d, J = 5.0 Hz), 4.04 (1H, t, J = 5.0 Hz), 3.66 (3H, s), 2.44 (2H, t, J = 4.8 Hz), 2.17 (6H, s), 2.03-1.95 (2H, m). | 530 |
| 19a | (DMSO) δ: 9.03 (1H, s), 7.80 (1H, br), 7.70 (1H, d, J = 8.0 Hz), 7.62 (2H, d, J = 8.0 Hz), 7.45 (1H, br), 7.22 (1H, t, J = 7.2 Hz), 6.98 (1H, d, J = 8.0 Hz), 4.49 (1H, brs). | 430 |

| Example No | ¹H NMR (400 MHz) | MS |
|---|---|---|
| 20a | (CDCl3) δ: 9.13 (1H, brs), 7.60-7.25 (5H, m), 6.78 (1H, d, J = 5.0 Hz), 4.07-3.91 (3H, m), 2.58-2.39 (2H, m), 2.32 (6H, s), 2.20 (3H, s). | 530 |
| 21a | (CD3OD) δ: 8.86 (1H, brs), 7.52-7.37 (5H, m), 6.47 (2H, d, J = 8.8 Hz), 4.67-4.64 (1H, m), 4.15-4.10 (2H, m), 3.61-3.58 (2H, m). | 471 |
| 22a | (DMSO-d6) δ: 10.02 (1H, brs), 9.07 (1H, brs), 8.84 (1H, brs), 7.80-7.59 (5H, m), 7.52-7.44 (1H, m), 7.24-7.19 (2H, m), 2.90-2.83 (6H, m), 1.70-1.64 (6H, m). | 508 |
| 23a | (CD3OD) δ: 8.98 (1H, brs), 7.80 (2H, d, J = 8.8 Hz), 7.64-7.61 (2H, m), 7.56-7.50 (2H, m), 7.47-7.43 (2H, m), 4.83-4.78 (1H, m), 3.75-3.64 (2H, m), 3.43-3.24 (2H, m). | 499 |
| 24a | (DMSO) δ: 10.02 (1H, s), 9.07 (1H, s), 7.75 (2H, d, J = 8.0 Hz), 7.65 (2H, d, J = 8.0 Hz), 7.51 (1H, t, J = 8.0 Hz), 7.15 (2H, d, J = 8.0 Hz), 2.61 (2H, t, J = 7.6 Hz), 2.55-2.52 (2H), 1.71 (2H, m), 1.01 (6H, s). | 498 |
| 25a | (DMSO) δ: 11.9 (1H, s), 10.2 (1H, s), 9.22 (1H, s), 9.20 (1H, d, J = 1.5 Hz), 8.95 (1H, s), 8.42 (1H, s), 8.21 (1H, s), 7.79-7.37 (5H, m), 3.32-3.29 (4H, m). | 483 |
| 26a | (DMSO-d6) δ: 11.85 (1H, s), 10.29 (1H, brs), 9.15 (1H, s), 8.95 (1H, s), 7.95-7.87 (2H, m), 7.62-7.60 (2H, m), 7.47 (1H, t, J = 8.0 Hz), 7.28-7.24 (2H, m), 3.12 (3H, s), 1.77 (3H, s). | 470 |
| 27a | (CD3OD) δ: 9.27 (1H, s), 7.96-7.91 (2H, m), 7.77-7.73 (5H, m), 7.68 (1H, dd, J = 9.4, 6.7 Hz), 4.14 (2H, t, J = 5.8 Hz), 3.88 (2H, t, J = 5.8 Hz). | 525 |
| 28a | (DMSO) δ: 9.20 (1H, brs), 8.05-7.97 (4H, m), 7.84-7.80 (2H, m), 7.70-7.65 (2H, m), 7.55-7.33 (4H, m), 6.99-6.96 (1H, m). | 493 |
| 29a | (DMSO) δ: 12.8 (1H, s), 11.9 (1H, brs), 10.2 (1H, brs), 9.10 (1H, s), 8.93-8.90 (1H, m), 8.11-7.30 (8H, m), 6.70 (1H, s). | 465 |
| 30a | (DMSO) δ: 11.9 (1H, s), 10.2 (1H, brs), 9.20 (1H, s), 9.18 (1H, s), 9.16 (1H, s), 8.42 (1H, s), 8.21 (1H, s), 7.79-7.37 (6H, m). | 482 |
| 31a | (DMSO) δ: 12.8 (1H, brs), 10.4 (1H, brs), 9.18 (1H, brs), 8.43 (1H, brs), 7.94-7.90 (4H, m), 7.68-7.50 (4H, m), 7.31-6.99 (4H, m). | 535 |
| 32a | (DMSO-d6) δ: 11.78 (1H, brs), 10.05 (1H, brs), 9.09 (1H, brs), 8.92 (1H, brs), 8.18 (1H, s), 7.69-7.59 (2H, m), 7.57-7.41 (3H, m), 7.13 (1H, t, J = 8.0 Hz), 6.17 (1H, d, J = 6.8 Hz), 3.97-3.88 (1H, m), 1.86-1.78 (2H, m), 1.67-1.48 (4H, m), 1.38-1.30 (2H, m). | 525 |
| 33a | (CD3OD) δ: 9.04 (1H, s), 7.90 (2H, d, J = 8.6 Hz), 7.83 (2H, d, J = 8.6 Hz), 7.79 (1H, s), 7.58 (2H, d, J = 7.8 Hz), 7.48 (1H, t, J = 7.8 Hz), 4.24-4.13 (1H, m), 2.97-2.84 (1H, m), 2.71-2.57 (1H, m), 2.31 (3H, s), 2.24-2.07 (2H, m), 1.94-1.59 (3H, m), 1.54-1.38 (1H, m). | 539 |
| 34a | (DMSO) δ: 9.97 (1H, s), 9.05 (1H, s), 7.75 (2H, d, J = 8.0 Hz), 7.64 (2H, d, J = 8.0 Hz), 7.50 (1H, t, J = 8.0 Hz), 7.15 (2H, d, J = 8.0 Hz), 2.61 (2H, t, J = 7.6 Hz), 2.55-2.52 (2H), 1.68 (2H, m), 1.06 (9H, s). | 512 |
| 35a | (CD3OD) δ: 9.28 (1H, brs), 8.02-7.80 (2H, m), 7.77-7.71 (4H, m), 7.68 (1H, dd, J = 9.4, 6.7 Hz), 3.34 (3H, s). | 481 |
| 36a | (CDCl3) δ: 7.55-7.50 (5H), 7.14 (2H, d, J = 8.0 Hz), 3.68 (2H, dd, J = 8.0 Hz), 2.80 (2H, dd, J = 8.0 Hz), 2.63 (4H, s). | 524 |
| 37a | (CD3OD) δ: 8.92 (1H, brs), 7.56-7.44 (5H, m), 6.94 (2H, d, J = 8.8 Hz), 4.25-4.20 (1H, m), 4.10-4.02 (3H, m), 3.89-3.85 (1H, m), 3.19 (4H, br), 2.57 (4H, br), 3.47 (3H, s). | 581 |
| 38a | (CD3OD) δ: 9.05 (1H, s), 7.88 (2H, br), 7.58 (2H, d, J = 8.8 Hz), 7.51-7.44 (3H, m), 3.67-3.66 (1H, m), 3.55-3.46 (1H, m), 3.09 (3H, s), 2.67-2.53 (2H, br), 2.37 (6H, s). | 527 |
| 39a | (DMSO) δ: 9.10 (1H, s), 8.87 (1H, s), 7.74-7.60 (4H, m), 7.50-7.40 (1H, m), 7.04 (2H, d, J = 8.4 Hz), 4.47 (2H, br), 2.21 (3H, s). | 444 |
| 40a | (CDCl3): 12.67-12.28 (1H × 1/2, brm), 10.03-9.69 (1H × 1/2, brm), 9.16 (1H, brs), 8.82-8.62 (1H × 1/2, brm), 8.02-7.83 (1H × 1/2, brm), 7.61-7.35 (3H, m), 7.47 (2H, d, J = 8.3 Hz), 6.89 (2H, d, J = 8.3 Hz), 6.42 (1H, brs), 3.76-3.65 (1H, m), 3.21-3.06 (2H, m), 2.75-2.66 (1H, m), 2.55-2.44 (2H, m), 2.39-2.27 (1H, m), 2.30 (3H, s), 1.05 (3H, d, J = 6.3 Hz). | 511 |
| 41a | (CDCl3) δ: 9.88 (1H, brs), 9.16 (1H, brs), 7.62-7.36 (3H, m), 7.47 (2H, d, J = 8.8 Hz), 6.89 (2H, d, J = 8.8 Hz), 6.42 (1H, brs), 3.76-3.66 (1H, m), 3.19-3.04 (2H, m), 2.75-2.66 (1H, m), 2.54-2.46 (2H, m), 2.39-2.28 (1H, m), 2.30 (3H, s), 1.05 (3H, d, J = 6.6 Hz). | 511 |
| 42a | (CDCl3) δ: 9.81 (1H, s), 9.15 (1H, s), 7.60-7.50 (2H, m), 7.48-7.40 (1H, m), 7.45 (2H, d, J = 9.0 Hz), 6.86 (2H, d, J = 9.0 Hz), 6.43 (1H, s), 3.94-3.85 (1H, m), 3.83-3.72 (2H, m), 3.55-3.43 (1H, m), 3.34-3.26 (1H, m), 3.08-2.99 (1H, m), 2.91-2.82 (1H, m), 2.59-2.49 (1H, m), 2.36-2.26 (1H, m), 2.32 (3H, s). | 527 |
| 43a | (DMSO-d6) δ: 9.07 (1H, s), 7.72-7.40 (5H, m), 6.86 (1H, d, J = 5.0 Hz), 3.96 (2H, t, J = 5.5 Hz), 2.34 (2H, t, J = 5.5 Hz), 2.14 (6H, s), 1.86-1.79 (2H, m). | 500 |
| 44a | (DMSO-d6) δ: 9.04 (1H, s), 7.73-7.41 (5H, m), 6.86 (1H, d, J = 5.0 Hz), 3.97 (2H, t, J = 5.5 Hz), 2.35 (2H, t, J = 5.5 Hz), 2.14 (6H, s). | 486 |
| 45a | (DMSO) δ: 11.9 (1H, brs), 10.4 (1H, brs), 9.19 (1H, s), 8.99 (1H, s), 8.86 (2H, d, J = 6.0 Hz), 8.35 8.33 (2H, m), 8.04-8.02 (2H, m), 7.63-7.60 (2H, m), 7.50-7.48 (1H, m), 7.37 (1H, t, J = 6.0 Hz). | 477 |

-continued

| Example No | ¹H NMR (400 MHz) | MS |
|---|---|---|
| 46a | (CD3OD) δ: 8.93 (1H, brs), 7.63-7.56 (5H, m), 6.98 (2H, d, J = 8.8 Hz), 3.76 (4H, br), 3.23 (2H, s), 3.19-3.13 (4H, m), 2.33 (6H, s). | 568 |
| 47a | (DMSO-d6) δ: 11.61 (1H, s), 9.01 (1H, s), 8.77 (1H, s), 7.66-7.43 (5H, m), 6.55 (2H, d, J = 9.3 Hz), 4.74 (1H, t, J = 5.6 Hz), 3.65-3.59 (1H, m), 3.51-3.45 (1H, m), 3.36 (1H, t, J = 7.6 Hz), 3.20-3.13 (1H, m), 3.02-2.96 (1H, m), 2.02-1.83 (4H, m). | 498 |
| 48a | (CD3OD) δ: 9.00 (1H, s), 7.67 (2H, d, J = 8.4 Hz), 7.59-7.56 (2H, m), 7.48 (1H, t, J = 8.4 Hz), 7.29 (2H, d, J = 8.4 Hz), 3.52 (2H, s), 2.65-2.35 (8H, br), 2.30 (3H, s). | 510 |
| 49a | (CD3OD) δ: 8.97 (1H, s), 7.60-7.54 (3H, m), 7.49-7.45 (1H, m), 7.34 (1H, br), 7.15 (1H, d, J = 8.4 Hz), 3.53 (2H, s), 2.33 (6H, s). | 471 |
| 50a | (CDCl3) δ: 9.17 (1H, brs), 7.60-7.30 (3H, m), 7.43 (2H, d, J = 5.0 Hz), 6.83 (2H, d, J = 5.0 Hz), 4.02 (2H, t, J = 5.2 Hz), 2.92-2.85 (1H, m), 2.78 (2H, t, J-5.2 Hz), 2.32 (3H, s), 1.02 (3H, d, J = 4.8 Hz). | 514 |
| 51a | (CDCl3) δ: 9.20 (1H, brs), 7.62-7.52 (5H, m), 7.23 (2H, d, J = 5.1 Hz), 4.25-4.22 (1H, m), 3.34-3.28 (1H, m), 3.24-3.18 (1H, m), 2.32-2.29 (2H, m), 2.20 (6H, s), 1.98-1.93 (1H, m), 1.76-1.72 (1H, m), 1.51-1.47 (2H, m), 1.33-1.28 (2H, m), 0.88 (3H, t, J = 5.2 Hz). | 556 |
| 52a | (CDCl3) δ: 9.17 (1H, brs), 7.57 (2H, d, J = 5.2 Hz), 7.43 (3H, d, J = 5.2 Hz), 6.84 (2H, d, J = 5.2 Hz), 3.57 (2H, t, J = 5.6 Hz), 3.38 (3H, s), 3.21-3.17 (4H, m), 2.68-2.63 (6H, m). | 541 |
| 53a | (DMSO) δ: 11.9 (1H, brs), 10.4 (1H, brs), 9.18 (1H, s), 8.99 (1H, s), 8.14-8.00 (3H, m), 7.62 (2H, d, J = 7.0 Hz), 7.52-7.45 (2H, m), 7.08 (1H, s), 3.97 (3H, s), 3.92 (3H, s). | 537 |
| 54a | (CD3OD) δ: 8.94 (1H, s), 7.60-7.49 (5H, m), 6.50 (2H, d, J = 7.3 Hz), 3.62-3.54 (4H, m), 2.68-2.32 (m, 4H), 2.31 (3H, s), 1.69-1.66 (4H, m). | 537 |
| 55a | (DMSO-d6) δ: 11.61 (1H, s), 9.01 (1H, s), 8.77 (1H, s), 7.66-7.43 (5H, m), 6.55 (2H, d, J = 9.3 Hz), 4.74 (1H, t, J = 5.6 Hz), 3.65-3.59 (1H, m), 3.51-3.45 (1H, m), 3.36 (1H, t, J = 7.6 Hz), 3.20-3.13 (1H, m), 3.02-2.96 (1H, m), 2.02-1.83 (4H, m). | 498 |
| 56a | (DMSO-d6) δ: 9.12 (1H, s), 7.78-7.63 (2H, m), 7.62 (2H, d, J = 5.1 Hz), 7.55-7.45 (1H, m), 6.90 (2H, d, J = 5.5 Hz), 4.08 (2H, q, J = 5.5 Hz), 3.99 (2H, t, J = 5.0 Hz), 2.43 (2H, t, J = 5.0 Hz), 2.02-1.95 (2H, m), 1.21 (3H, t, J = 5.5 Hz). | 529 |
| 57a | (CDCl3) δ: 9.15 (1H, brs), 7.60-7.40 (3H, m), 7.42 (2H, d, J = 5.0 Hz), 6.88 (2H, d, J = 5.0 Hz), 4.07-4.00 (1H, m), 3.99-3.93 (2H, m), 2.53 (1H, t, J = 5.2 Hz), 2.37 (1H, dd, J = 5.2, 1.3 Hz), 2.37 (6H, s). | 516 |
| 58a | (CD3OD) δ: 8.95 (1H, s), 7.54-7.37 (5H, m), 7.48 (1H, t, J = 8.4 Hz), 6.91 (2H, d, J = 8.8 Hz), 4.04 (2H, s), 3.14 (4H, br), 2.78 (4H, br), 1.21 (6H, s). | 556 |
| 59a | (DMSO-d6) δ: 9.14 (1H, s), 7.90-7.85 (2H, m), 7.63-7.57 (2H, m), 7.45-7.42 (1H, m), 7.33 (2H, d, J = 5.3 Hz), 4.42 (2H, s), 2.88 (3H, s). | 491 |
| 60a | (DMSO-d6) δ: 10.07 (1H, brs), 9.10 (1H, brs), 8.88 (1H, brs), 7.77-7.70 (3H, m), 7.65-7.59 (2H, m), 7.51-7.43 (1H, m), 7.30-7.26 (2H, m), 2.41-2.23 (4H, m), 2.13 (3H, s), 2.05-1.96 (2H, m), 1.72-1.65 (2H, m), 1.14 (3H, s). | 510 |
| 61a | (DMSO-d6) δ: 10.32 (1H, s), 7.94 (2H, d, J = 8.4 Hz), 7.66 (2H, d, J = 6.8 Hz), 7.52 (1H, m), 7.36 (2H, d, J = 8.4 Hz), 3.35 (4H, m), 3.03 (2H, m), 2.26 (1H, m), 1.86 (2H, m), 1.69 (5H, m), 1.39 (5H, m). | 579 |
| 62a | (CD3OD) δ: 9.01 (1H, s), 7.90 (0H, s), 7.75 (2H, d, J = 8.3 Hz), 7.59 (2H, d, J = 7.8 Hz), 7.49 (1H, t, J = 8.0 Hz), 7.32 (2H, d, J = 8.8 Hz), 3.63 (2H, s), 2.60 (4H, q, J = 7.2 Hz), 1.10 (6H, t, J = 7.3 Hz). | 484 |
| 63a | (DMSO-d6) δ: 11.95 (1H, brs), 10.64 (1H, brs), 9.21 (1H, s), 9.07 (1H, brs), 8.12 (2H, d, J = 8.8 Hz), 7.66-7.59 (4H, m), 7.48 (1H, t, J = 8.2 Hz), 2.91-2.81 (4H, brm), 2.39-2.31 (4H, brm), 2.13 (3H, s). | 561 |
| 64a | (CD3OD) δ: 8.98 (1H, s), 8.13 (1H, s), 7.55-7.38 (4H, m), 7.24 (2H, d, J = 8.0z), 4.53 (1H, m), 3.96 (1H, m), 3.17 (2H, m), 2.63 (2H, m), 2.09 (3H, s), 1.90 (2H, m), 1.66-1.61 (2H). | 567 |
| 65a | (CDCl3) δ: 9.12 (1H, brs), 7.57-7.40 (3H, m), 7.42 (2H, d, J = 5.5 Hz), 6.80 (2H, d, J = 5.5 Hz), 3.85-3.82 (2H, m), 2.70-2.31 (4H, m), 2.17 (3H, s), 2.09-2.02 (2H, m), 1.61-1.55 (1H, m). | 512 |
| 66a | (DMSO-d6) δ: 11.96 (1H, brs), 10.66 (1H, brs), 9.22 (1H, s), 9.08 (1H, s), 8.18-8.12 (2H, m), 7.67-7.60 (4H, m), 7.48 (1H, t, J = 8.0 Hz), 3.65-3.60 (4H, m), 2.87-2.82 (4H, m). | 548 |
| 67a | (DMSO-d6) δ: 11.86 (1H, s), 10.10 (1H, s), 9.14 (1H, s), 8.92 (1H, s), 7.63-7.59 (2H, m), 7.49-7.44 (2H, m), 7.38 (1H, d, J = 8.3 Hz), 7.18 (1H, t, J = 8.0 Hz), 6.61 (1H, dd, J = 8.0, 1.7 Hz), 4.09 (2H, t, J = 5.8 Hz), 3.59-3.55 (4H, m), 2.69 (2H, t, J = 5.8 Hz), 2.47-2.44 (4H, m). | 528 |
| 68a | (DMSO-d6) δ: 11.71 (1H, brs), 9.97 (1H, brs), 9.07 (1H, brs), 8.84 (1H, brs), 7.75-7.56 (4H, m), 7.50-7.43 (1H, m), 6.91-6.87 (2H, m), 4.33-4.25 (1H, m), 2.66-2.57 (2H, m), 2.20-2.12 (2H, m), 2.17 (3H, s), 1.95-1.86 (2H, m), 1.66-1.55 (2H, m). | 512 |
| 69a | (DMSO) δ: 9.03 (1H, s), 7.66 (2H, br), 7.50-7.30 (3H, br), 6.90 (2H, d, J = 8.4 Hz), 3.11 (4H, br), 2.53 (4H, br), 2.44 (3H, s), 2.15 (3H, s). | 477 |

-continued

| Example No | ¹H NMR (400 MHz) | MS |
|---|---|---|
| 70a | (DMSO) δ: 9.08 (1H, s), 7.84 (2H, d, J = 8.0 Hz), 7.60-7.56 (2H, m), 7.50-7.45 (1H, m), 7.31 (2H, t, J = 8.0 Hz), 7.04 (1H, t, J = 7.2 Hz). | 399 |
| 71a | (CD3OD) δ: 8.99 (1H, s), 8.10 (1H, s), 7.56 (2H, d, J = 8.0 Hz), 7.47-7.40 (2H), 7.23 (2H, d, J = 8.0 Hz), 3.22 (2H, t, J = 8.0 Hz), 2.38 (2H, t, J = 8.0 Hz), 1.90 (3H, m) 1.85 (2H, m). | 541 |
| 72a | (DMSO-d6) δ: 10.10 (1H, s), 9.12 (1H, s), 8.91 (1H, s), 7.75 (2H, brs), 7.61 (2H, d, J = 7.8 Hz), 7.47 (1H, t, J = 7.6 Hz), 7.24 (1H, t, J = 7.8 Hz), 6.98 (1H, d, J = 7.3 Hz), 3.57 (2H, s), 3.32 (2H, s), 2.45 (4H, s), 1.69 (4H, s). | 482 |
| 73a | (CDCl3) δ: 9.17 (1H, brs), 7.58 (2H, d, J = 7.4 Hz), 7.42 (3H, d, J = 7.4 Hz), 6.83 (2H, d, J = 7.4 Hz), 3.95 (1H, dd, J = 7.4, 3.5 Hz), 3.78-3.70 (1H, m), 2.39-2.30 (1H, m), 2.21 (6H, s), 2.16-2.10 (2H, m), 1.04 (3H, d, J = 7.4 Hz). | 514 |
| 74a | (DMSO-d6) δ: 9.15 (1H, s), 7.70-7.60 (2H, m), 7.58-7.42 (3H, m), 7.20 (1H, d, J = 5.3 Hz), 6.62 (1H, d, J = 3.2 Hz), 4.00-3.77 (2H, m), 2.27-2.33 (1H, m), 2.18 (6H, s), 2.13-2.06 (2H, m), 1.02 (3H, d, J = 4.7 Hz). | 514 |
| 75a | (CD3OD) δ: 9.07 (1H, s), 8.09 (2H, d, J = 8.8 Hz), 7.69 (2H, d, J = 8.8 Hz), 7.60 (2H, d, J = 8.0 Hz), 7.50 (1H, t, J = 8.0 Hz), 3.43-3.36 (2H, m), 3.15 (3H, s), 3.13 (3H, s), 3.12-2.95 (2H, m), 2.32-2.12 (2H, m). | 548 |
| 76a | (CD3OD) δ: 8.96 (1H, s), 7.58-7.53 (3H, m), 7.46-7.42 (1H, m), 7.28 (1H, t, J = 8.4 Hz), 7.20 (2H, d, J = 8.4 Hz), 3.54 (2H, s), 2.70-2.35 (8H, br), 2.26 (3H, s). | 510 |
| 77a | (400 MHz, CD3OD) δ: 9.03 (1H, s), 7.63 (4H, d, J = 5.5 Hz), 7.55 (1H, t, J = 5.5 Hz), 6.95 (2H, d, J = 5.5 Hz), 4.05 (2H, t, J = 4.3 Hz), 2.50 (2H, t, J = 4.3 Hz), 2.15-2.08 (2H, m). | 501 |
| 78a | (CD3OD) δ: 9.02 (1H, s), 8.10 (1H, s), 7.62-7.57 (2H, m), 7.52-7.45 (2H, m), 7.29-7.21 (2H, m), 2.14 (3H, s). | 456 |
| 79a | (CD3OD and a few drops of CDCl3) δ: 9.06 (1H, s), 8.07-8.03 (2H, m), 8.01-7.97 (2H, m), 7.62-7.56 (2H, m), 7.52-7.47 (1H, m), 3.91 (2H, s), 2.42 (6H, s). | 524 |
| 80a | (CD3OD) δ: 8.97 (1H, s), 7.58-7.55 (4H, m), 7.47 (1H, t, J = 8.8 Hz), 6.96 (2H, d, J = 8.8 Hz), 3.93-3.67 (4H, m), 3.55-3.50 (1H, m), 3.20-3.07 (4H, m), 2.29 (6H, s), 1.22 (3H, d, J = 6.4 Hz). | 582 |
| 81a | (CD3OD) δ: 8.93 (1H, s), 7.89 (1H, d, J = 8.0 Hz), 7.82 (1H, d, J = 8.0 Hz), 7.68 (1H, t, J = 8.0 Hz), 7.58 (2H, br), 6.98 (2H, d, J = 8.8 Hz), 3.21-3.18 (4H, m), 2.64-2.67 (4H, m), 2.37 (3H, s). | 530 |
| 82a | (DMSO-d6) δ: 11.93 (1H, brs), 10.55 (1H, brs), 9.20 (1H, s), 9.03 (1H, brs), 8.06 (2H, d, J = 9.0 Hz), 7.71 (2H, d, J = 9.0 Hz), 7.62 (2H, d, J = 7.8 Hz), 7.52-7.39 (2H, m), 2.85-2.76 (2H, m), 2.44-2.39 (2H, m), 2.37-2.29 (4H, m), 1.65-1.58 (4H, m). | 575 |

INDUSTRIAL APPLICABILITY

A compound of the present invention has an excellent Wee1 kinase inhibiting effect, and is therefore useful in the field of medicine, particularly in various types of cancer therapy.

The invention claimed is:
1. A compound of Formula (I-1):

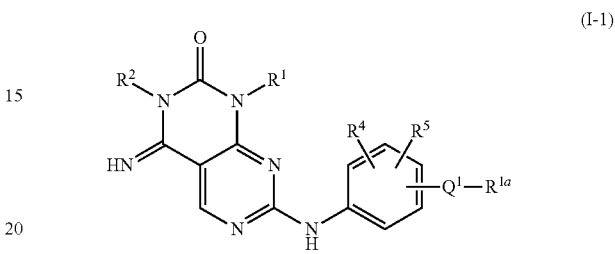

(I-1)

or a pharmaceutically acceptable salt,
wherein
Q1 is a single bond, or a C1-C6 alkylene group, in which one or two or more methylene groups constituting the C1-C6 alkylene group may be independently replaced with an oxygen atom, a sulfur atom, a carbonyl group, an imino group, a sulfinyl group or a sulfonyl group, and may be substituted with a halogen atom, a cyano group, a hydroxyl group, a C1-C6 alkyl group or a C1-C6 alkoxy group;
R1a is a hydrogen atom, a hydroxyl group, a formyl group, a C1-C6 alkyl group, a di-C1-C6 alkylamino group, a hydroxy-C1-C6 alkyl group or a carboxyphenyl group, or a heterocyclic group, wherein said heterocyclic group means a monocyclic or bicyclic heterocyclic group formed of 3 to 7 carbon atoms in each ring and containing one or two nitrogen atoms, wherein said heterocyclic group may be aromatic or aliphatic, and which may have a substituent selected from the group consisting of a halogen atom, a hydroxyl group, an oxo group, a C1-C6 alkyl group, a C1-C6 alkoxy group, a hydroxy-C1-C6 alkyl group, a C1-C6 alkoxy-C1-C6 alkyl group, and a group represented by —R1b;
R1b is a group represented by -Q2-A1 (R1c)R1d;
Q2 is a single bond, or a C1-C6 alkylene group, in which one or two or more methylene groups constituting the C1-C6 alkylene group may be independently replaced with an oxygen atom, a sulfur atom, a carbonyl group, an imino group, a sulfinyl group or a sulfonyl group, and may be substituted with a halogen atom, a cyano group, a hydroxyl group, an imino group, a C1-C6 alkyl group or a C1-C6 alkoxy group;
A1 is a nitrogen atom, or a methine group which may be substituted with a hydroxyl group, a C1-C6 alkyl group or a hydroxy-C1-C6 alkyl group;
R1c and R1d are independently a hydrogen atom, a carboxyl group, a C1-C6 alkyl group, or a hydroxy-C1-C6 alkyl group, or together represent a C1-C6 alkylene group, in which one or two or more methylene groups constituting the C1-C6 alkylene group may be independently replaced with an oxygen atom, a sulfur atom, a sulfonyl group, a sulfonyl group, a carbonyl group, a vinylene group or a group represented by —N(R1e)-, and may be substituted with a hydroxyl group, a C1-C6 alkyl group or a hydroxy-C1-C6 alkyl group;

R1e is a hydrogen atom, a formyl group, an acetyl group or a C1-C6 alkyl group;

R1 is a hydrogen atom; a C1-C6 alkyl group which may have a substituent selected from the group consisting of a halogen atom, a hydroxyl group, a cyano group, a C1-C6 alkoxy group, a C3-C6 cycloalkyl group, a C2-C7 alkanoyl group and a C1-C6 alkylsulfonyl group; or an aryl, aralkyl, or heteroaryl group which may have a substituent selected from the group consisting of a halogen atom, a hydroxyl group, a cyano group, an amino group, a C1-C6 alkyl group, a C1-C6 alkoxy group, a halo-C1-C6 alkyl group and a hydroxy-C1-C6 alkyl group;

R2 is an aryl, aralkyl or heteroaryl group, wherein said heteroaryl group means a 5 or 6 membered monocyclic heteroaryl group having one to three heteroatoms selected from the group consisting of an oxygen atom, a nitrogen atom, and a sulfur atom, or a condensed-ring heteroaryl group formed by the condensation of the monocyclic heteroaryl group and the aryl group or by the condensation of the monocyclic heteroaryl groups, which may be the same or different, and which may have a substituent selected from the group consisting of a halogen atom, a hydroxyl group, a cyano group, an amino group, a nitro group, a carbamoyl group, a C1-C6 alkyl group, a C1-C6 alkoxy group, a C1-C6 alkylsulfonyl group, a halo-C1-C6 alkyl group, a hydroxy-C1-C6 alkyl group and a C1-C6 alkoxy-C1-C6 alkyl group; and R4 and R5 are independently a hydrogen atom, a halogen atom, a C1-C6 alkyl group, a halo-C1-C6 alkyl group, a hydroxy-C1-C6 alkyl group, a C1-C6 alkoxy group, a C2-C7 alkanoyl group, a hydroxy-C1-C6 alkylamino group, a carbamoyl group, or a hydroxy-C1-C6 alkyl-carbamoyl group.

2. The compound of claim 1, or a pharmaceutically acceptable salt, wherein
R2 is a group represented by the Formula (a)

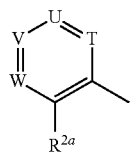

(a)

wherein
R2a is a halogen atom, a hydroxyl group, a cyano group, an amino group, a nitro group, a carbamoyl group, a C1-C6 alkyl group, a C1-C6 alkylsulfonyl group, a C1-C6 alkoxy group, a halo-C1-C6 alkyl group, a hydroxy-C1-C6 alkyl group or a C1-C6 alkoxy-C1-C6 alkyl group; and T, U, V and W are a nitrogen atom, or a methine group which may be substituted with a halogen atom, a hydroxyl group, a cyano group, an amino group, a nitro group, a carbamoyl group, a C1-C6 alkyl group, a C1-C6 alkylsulfonyl group, a C1-C6 alkoxy group, a halo-C1-C6 alkyl group, a hydroxy-C1-C6 alkyl group and a C1-C6 alkoxy-C1-C6 alkyl group, wherein at least two of them are the methine groups.

3. The compound of claim 2, or a pharmaceutically acceptable salt, wherein
R2 is a group represented by the Formula (a),
R2a is a halogen atom, and
T is a methine group substituted with a halogen atom or a C1-C6 alkyl group.

4. The compound of claim 3, or a pharmaceutically acceptable salt, wherein R2 is a 2,6-dichlorophenyl group.

5. The compound of claim 1, or a pharmaceutically acceptable salt, wherein R1 is a hydrogen atom, or a C1-C6 alkyl group which may be substituted with a halogen atom or a hydroxyl group.

6. The compound of claim 1, or a pharmaceutically acceptable salt, wherein
R1 is a hydrogen atom, or a C1-C6 alkyl group which may be substituted with a hydroxyl group; and
the group represented by -Q1-R1a is a group selected from the groups represented by the Formulae (a1):

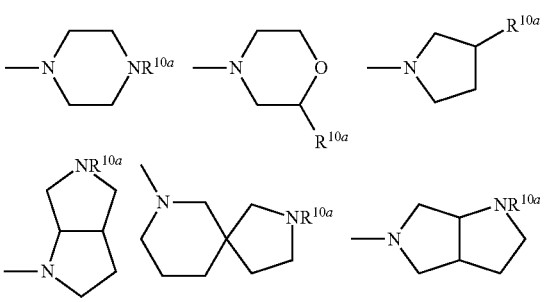

(a1)

wherein
one or two or more methylene groups constituting said group may be independently substituted with a substituent selected from the group consisting of a halogen atom, a hydroxyl group, an oxo group, a C1-C6 alkyl group, a C1-C6 alkoxy group, a hydroxy-C1-C6 alkyl group, a C1-C6 alkoxy-C1-C6 alkyl group and a group represented by —R1b;
R10a is a hydrogen atom, a C1-C6 alkyl group, a hydroxy-C1-C6 alkyl group or a group represented by —R1b.

7. The compound of claim 6, or a pharmaceutically acceptable salt,
wherein R1b is a group represented by -Q2-A1(R1c)R1d, in which:
(i) Q2 is a single bond, A1 is a nitrogen atom, and R1c and R1d are independently a hydrogen atom or a C1-C6 alkyl group;
(ii) Q2 is a single bond, or a C1-C6 alkylene group, in which one of the methylene groups constituting the C1-C6 alkylene group may be replaced with a carbonyl group, A1 is a methine group, and R1c and R1d are hydrogen atoms;
(iii) Q2 is a C1-C6 alkylene group, in which one of the methylene groups constituting the C1-C6 alkylene group may be replaced with an oxygen atom or a carbonyl group, or may be substituted with a C1-C6 alkyl group, A1 is a nitrogen atom, and R1c and R1d are independently C1-C6 alkyl groups; or
(iv) Q2 is a single bond, A1 is a methine group, and R1c and R1d together represent a C1-C6 alkylene group, in which one of the methylene groups constituting the C1-C6 alkylene group may be replaced with a group represented by —N(R1e)-.

8. The compound of claim 1, which is:
(1) 3-(2,6-dichlorophenyl)-7-({4-[4-(2-hydroxyethyl)piperazin-1-yl]phenyl}amino)-4-imino-1-methyl-3,4-dihydropyrimido[4,5-d]pyrimidin-2(1H)-one;

(2) 3-(2,6-dichlorophenyl)-7-({4-[2-(hydroxymethyl)morpholin-4-yl]phenyl}amino)-4-imino-1-methyl-3,4-dihydropyrimido[4,5-d]pyrimidin-2(1H)-one;
(3) 3-(2,6-dichlorophenyl)-7-[(4-{4-[(dimethylamino)acetyl]piperazin-1-yl}phenyl)amino]-4-imino-1-methyl-3,4-dihydropyrimido[4,5-d]pyrimidin-2(1H)-one;
(4) 3-(2,6-dichlorophenyl)-7-[(4-{2-[(dimethylamino)methyl]morpholin-4-yl}phenyl)amino]-4-imino-1-methyl-3,4-dihydropyrimido[4,5-d]pyrimidin-2(1H)-one;
(5) 3-(2,6-dichlorophenyl)-4-imino-7-{[4-(4-methylpiperazin-1-yl)phenyl]amino}-3,4-dihydropyrimido[4,5-d]pyrimidin-2(1H)-one;
(6) 3-(2,6-dichlorophenyl)-4-imino-7-{[3-methyl-4-(4-methylpiperazin-1-yl)phenyl]amino}-3,4-dihydropyrimido[4,5-d]pyrimidin-2(1H)-one;
(7) 3-(2,6-dichlorophenyl)-4-imino-1-methyl-7-{[4-(4-methylpiperazin-1-yl)phenyl]amino}-3,4-dihydropyrimido[4,5-d]pyrimidin-2(1H)-one;
(8) 3-(2,6-dichlorophenyl)-7-({4-[(3R)-3-dimethylaminopyrrolidin-1-yl]phenyl}amino)-4-imino-3,4-dihydropyrimido[4,5-d]pyrimidin-2(1H)-one;
(9) 3-(2,6-dichlorophenyl)-4-imino-7-{[4-(5-methylhexahydropyrrolo[3,4-b]pyrrol-1(2H)-yl)phenyl}amino)-3,4-dihydropyrimido[4,5-d]pyrimidin-2(1H)-one;
(10) 3-(2,6-dichlorophenyl)-4-imino-7-{[4-(2-methyl-2,7-diazaspiro[4,5]dec-7-yl)phenyl}amino)-3,4-dihydropyrimido[4,5-d]pyrimidin-2(1H)-one;
(11) 3-(2,6-dichlorophenyl)-4-imino-7-{[4-(1-methylhexahydropyrrolo[3,4-b]pyrrol-5(1H)-yl)phenyl]amino}-3,4-dihydropyrimido[4,5-d]pyrimidin-2(1H)-one;
(12) 3-(2,6-dichlorophenyl)-4-imino-7-({4-[(2R)-2-(methoxymethyl)-4-methylpiperazin-1-yl]phenyl}amino)-3,4-dihydropyrimido[4,5-d]pyrimidin-2(1H)-one;
(13) 7-({4-[3-(tert-butylamino)pyrrolidin-1-yl]phenyl}amino)-3-(2,6-dichlorophenyl)-4-imino-3,4-dihydropyrimido[4,5-d]pyrimidin-2(1H)-one;
(14) 3-(2,6-dichlorophenyl)-7-({4-[(3S)-3-(dimethylamino)pyrrolidin-1-yl]phenyl}amino)-4-imino-3,4-dihydropyrimido[4,5-d]pyrimidin-2(1H)-one;
(15) 7-{[4-(4-acetylpiperazin-1-yl)-3-methylphenyl]amino}-3-(2,6-dichlorophenyl)-4-imino-3,4-dihydropyrimido[4,5-d]pyrimidin-2(1H)-one;
(16) 3-(2,6-dichlorophenyl)-4-imino-7-{[4-(2-methyl-2,7-diazaspiro[3,5]non-7-yl)phenyl]amino}-3,4-dihydropyrimido[4,5-d]pyrimidin-2(1H)-one;
(17) 7-({4-[4-(1-acetylazetidin-3-yl)piperazin-1-yl]phenyl}amino)-3-(2,6-dichlorophenyl)-4-imino-1-methyl-3,4-dihydropyrimido[4,5-d]pyrimidin-2(1H)-one;
(18) 3-(2,6-dichlorophenyl)-4-imino-7-{[4-(morpholin-4-yl)phenyl]amino}-3,4-dihydropyrimido[4,5-d]pyrimidin-2(1H)-one;
(19) 3-(2,6-dichlorophenyl)-7-({4-[2-(dimethylamino)-1-methylethoxy]phenyl}amino)-4-imino-3,4-dihydropyrimido[4,5-d]pyrimidin-2(1H)-one;
(20) 3-(2,6-dichlorophenyl)-4-imino-7-({4-[methyl(pyridin-2-ylmethyl)amino]phenyl}amino)-3,4-dihydropyrimido[4,5-d]pyrimidin-2(1H)-one;
(21) 3-(2,6-dichlorophenyl)-7-({4-[4-(2-hydroxyethyl)piperazin-1-yl]phenyl}amino)-4-imino-3,4-dihydropyrimido[4,5-d]pyrimidin-2(1H)-one;
(22) 3-(2,6-dichlorophenyl)-7-({4-[2-(dimethylamino)propoxy]phenyl}amino)-4-imino-3,4-dihydropyrimido[4,5-d]pyrimidin-2(1H)-one;
(23) 3-(2,6-dichlorophenyl)-7-[(4-{2-[(dimethylamino)methyl]morpholin-4-yl}phenyl)amino]-4-imino-3,4-dihydropyrimido[4,5-d]pyrimidin-2(1H)-one;
(24) 3-(2,6-dichlorophenyl)-7-({3-[3-(dimethylamino)propoxy]-4-methoxyphenyl}amino)-4-imino-3,4-dihydropyrimido[4,5-d]pyrimidin-2(1H)-one;
(25) 3-(2,6-dichlorophenyl)-7-({4-[(dimethylamino)methyl]phenyl}amino)-4-imino-3,4-dihydropyrimido[4,5-d]pyrimidin-2(1H)-one;
(26) 3-(2,6-dichlorophenyl)-7-({4-[3-(dimethylamino)-3-(hydroxymethyl)pyrrolidin-1-yl]phenyl}amino)-4-imino-3,4-dihydropyrimido[4,5-d]pyrimidin-2(1H)-one;
(27) 3-(2,6-dichlorophenyl)-7-[(4-{1-[2-(dimethylamino)ethyl]-1H-pyrazol-4-yl}phenyl)amino]-4-imino-3,4-dihydropyrimido[4,5-d]pyrimidin-2(1H)-one; or
(28) 3-(2,6-dichlorophenyl)-1-(2-hydroxyethyl)-4-imino-7-{[4-(4-methylpiperazin-1-yl)phenyl]amino}-3,4-dihydropyrimido[4,5-d]pyrimidin-2(1H)-one, or a pharmaceutically acceptable salt thereof.

9. A pharmaceutical composition which comprises a therapeutically effective amount of the compound of claim 1, or a pharmaceutically acceptable salt, and a pharmaceutically acceptable carrier or diluent.

10. A method of treating a Wee1 kinase mediated cancer, wherein said cancer is selected from the group consisting of breast cancer, lung cancer, pancreatic cancer, colon cancer, ovarian cancer, acute leukemia, chronic lymphocytic leukemia, chronic myeloid leukemia, and Hodgkin's lymphoma, with a therapeutically effective amount of the pharmaceutical composition of claim 9 to a mammal in need thereof.

11. A combined preparation for simultaneous, separate or successive administration in cancer therapy, comprising the following two separate preparations (a) and (b):
(a) a preparation comprising a compound of claim 1, or a pharmaceutically acceptable salt, together with a pharmaceutically acceptable carrier or diluent; and
(b) a preparation comprising, together with a pharmaceutically acceptable carrier or diluent, an anticancer agent selected from the group consisting of anticancer alkylating agents, anticancer antimetabolites, anticancer antibiotics, plant-derived anticancer agents, anticancer platinum coordination compounds, anticancer camptothecin derivatives, anticancer tyrosine kinase inhibitors, monoclonal antibodies, interferons, biological response modifiers, and other anticancer agents, or a pharmaceutically acceptable salt, wherein the anticancer alkylating agents being nitrogen mustard N-oxide, cyclophosphamide, ifosfamide, melphalan, busulfan, mitobronitol, carboquone, thiotepa, ranimustine, nimustine, temozolomide, or carmustine, the anticancer antimetabolites being methotrexate, 6-mercaptopurine riboside, mercaptopurine, 5-fluorouracil, tegafur, doxifluridine, carmofur, cytarabine, cytarabine ocfosfate, enocitabine, S-1, gemcitabine, fludarabine, or pemetrexed disodium, the anticancer antibiotics being actinomycin D, doxorubicin, daunorubicin, neocarzinostatin, bleomycin, peplomycin, mitomycin C, aclarubicin, pirarubicin, epirubicin, zinostatin stimalamer, idarubicin, sirolimus, or valrubicin, the plant-derived anticancer agents being vincristine, vinblastine, vindeshine, etoposide, sobuzoxane, docetaxel, paclitaxel, or vinorelbine, the anticancer platinum coordination compounds being cisplatin, carboplatin, nedaplatin, or oxaliplatin, the anticancer camptothecin derivatives being irinotecan, topotecan, or camptothecin, the anticancer tyrosine kinase inhibitors being gefitinib, imatinib, or erlotinib, the monoclonal antibodies being cetuximab, bevacizumab, rituximab, alemtuzumab, or trastuzumab, the interferons being interferon α, interferon α-2a, interferon α-2b, interferon β, interferon γ-1a, or interferon γ-n1, the biological response modifiers being krestin, lentinan, sizofuran, picibanil, or ubenimex, and the other anticancer agents being mitoxantrone, L-asparaginase, procarbazine, dacarbazine, hydroxycarbamide, pentostatin, tretinoin, alefacept, darbepoetin alfa, anastrozole, exemestane, bicalutamide, leuprorelin, flutamide, fulvestrant, pegaptanib octasodium, denileukin diftitox, aldesleukin, thyrotropin alfa, arsenic trioxide, bortezomib, capecitabine, or goserelin.

12. A pharmaceutical composition which comprises, together with a pharmaceutically acceptable carrier or diluent, the compound of claim 1, or a pharmaceutically acceptable salt, and an anticancer agent selected from the group consisting of anticancer alkylating agents, anticancer antimetabolites, anticancer antibiotics, plant-derived anticancer agents, anticancer platinum coordination compounds, anticancer camptothecin derivatives, anticancer tyrosine kinase inhibitors, monoclonal antibodies, biological response modifiers, and other anticancer agents, wherein the anticancer alkylating agents being nitrogen mustard N-oxide, cyclophosphamide, ifosfamide, melphalan, busulfan, mitobronitol, carboquone, thiotepa, ranimustine, nimustine, temozolomide, or carmustine, the anticancer antimetabolites being methotrexate, 6-mercaptopurine riboside, mercaptopurine, 5-fluorouracil, tegafur, doxifluridine, carmofur, cytarabine, cytarabine ocfosfate, enocitabine, S-1, gemcitabine, fludarabine, or pemetrexed disodium, the anticancer antibiotics being actinomycin D, doxorubicin, daunorubicin, neocarzinostatin, bleomycin, peplomycin, mitomycin C, aclarubicin, pirarubicin, epirubicin, zinostatin stimalamer, idarubicin, sirolimus, or valrubicin, the plant-derived anticancer agents being vincristine, vinblastine, vindeshine, etoposide, sobuzoxane, docetaxel, paclitaxel, or vinorelbine, the anticancer platinum coordination compounds being cisplatin, carboplatin, nedaplatin, or oxaliplatin, the anticancer camptothecin derivatives being irinotecan, topotecan, or camptothecin, the anticancer tyrosine kinase inhibitors being gefitinib, imatinib, or erlotinib, the monoclonal antibodies being cetuximab, bevacizumab, rituximab, alemtuzumab, or trastuzumab, the interferons being interferon α, interferon α-2a, interferon α-2b, interferon β, interferon γ-1a, or interferon γ-n1, the biological response modifiers being krestin, lentinan, sizofuran, picibanil, or ubenimex, and the other anticancer agents being mitoxantrone, L-asparaginase, procarbazine, dacarbazine, hydroxycarbamide, pentostatin, tretinoin, alefacept, darbepoetin alfa, anastrozole, exemestane, bicalutamide, leuprorelin, flutamide, fulvestrant, pegaptanib octasodium, denileukin diftitox, aldesleukin, thyrotropin alfa, arsenic trioxide, bortezomib, capecitabine, or goserelin, or a pharmaceutically acceptable salt thereof.

13. A method of enhancing the effectiveness of radiation by administering the pharmaceutical composition of claim 9 in a mammal in need thereof.

14. The method of claim 13 which further comprises an anticancer agent wherein the anticancer agent is selected from the group consisting of anticancer alkylating agents, anticancer antimetabolites, anticancer antibiotics, plant-derived anticancer agents, anticancer platinum coordination compounds, anticancer camptothecin derivatives, anticancer tyrosine kinase inhibitors, monoclonal antibodies, biological response modifiers, and other anticancer agents, wherein the anticancer alkylating agents being nitrogen mustard N-oxide, cyclophosphamide, ifosfamide, melphalan, busulfan, mitobronitol, carboquone, thiotepa, ranimustine, nimustine, temozolomide, or carmustine, the anticancer antimetabolites being methotrexate, 6-mercaptopurine riboside, mercaptopurine, 5-fluorouracil, tegafur, doxifluridine, carmofur, cytarabine, cytarabine ocfosfate, enocitabine, S-1, gemcitabine, fludarabine, or pemetrexed disodium, the anticancer antibiotics being actinomycin D, doxorubicin, daunorubicin, neocarzinostatin, bleomycin, peplomycin, mitomycin C, aclarubicin, pirarubicin, epirubicin, zinostatin stimalamer, idarubicin, sirolimus, or valrubicin, the plant-derived anticancer agents being vincristine, vinblastine, vindeshine, etoposide, sobuzoxane, docetaxel, paclitaxel, or vinorelbine, the anticancer platinum coordination compounds being cisplatin, carboplatin, nedaplatin, or oxaliplatin, the anticancer camptothecin derivatives being irinotecan, topotecan, or camptothecin, the anticancer tyrosine kinase inhibitors being gefitinib, imatinib, or erlotinib, the monoclonal antibodies being cetuximab, bevacizumab, rituximab, alemtuzumab, or trastuzumab, the interferons being interferon α, interferon α-2a, interferon α-2b, interferon β, interferon γ-1a, or interferon γ-n1, the biological response modifiers being krestin, lentinan, sizofuran, picibanil, or ubenimex, and the other anticancer agents being mitoxantrone, L-asparaginase, procarbazine, dacarbazine, hydroxycarbamide, pentostatin, tretinoin, alefacept, darbepoetin alfa, anastrozole, exemestane, bicalutamide, leuprorelin, flutamide, fulvestrant, pegaptanib octasodium, denileukin diftitox, aldesleukin, thyrotropin alfa, arsenic trioxide, bortezomib, capecitabine, or goserelin or a pharmaceutically acceptable salt thereof.

* * * * *